(12) United States Patent
Shoseyov et al.

(10) Patent No.: US 9,095,569 B2
(45) Date of Patent: Aug. 4, 2015

(54) METHODS OF GENERATING AND USING PROCOLLAGEN

(75) Inventors: Oded Shoseyov, Karmei Yoseef (IL); Or Dgany, Ashdod (IL); Daniel L. Siegel, Rechovot (IL)

(73) Assignee: CollPlant Ltd., Nes Ziona (IL)

( * ) Notice: Subject to any disclaimer, the term of this patent is extended or adjusted under 35 U.S.C. 154(b) by 0 days.

(21) Appl. No.: 12/988,326

(22) PCT Filed: Apr. 16, 2009

(86) PCT No.: PCT/IL2009/000419
§ 371 (c)(1),
(2), (4) Date: Oct. 18, 2010

(87) PCT Pub. No.: WO2009/128076
PCT Pub. Date: Oct. 22, 2009

(65) Prior Publication Data
US 2011/0269667 A1    Nov. 3, 2011

Related U.S. Application Data

(60) Provisional application No. 61/071,267, filed on Apr. 18, 2008, provisional application No. 61/129,976, filed on Aug. 4, 2008.

(51) Int. Cl.
*A61K 38/00* (2006.01)
*C07K 14/78* (2006.01)
*A61K 38/39* (2006.01)

(52) U.S. Cl.
CPC ...................................... *A61K 38/39* (2013.01)

(58) Field of Classification Search
CPC ................................. A61K 38/00; C07K 14/78
See application file for complete search history.

(56) References Cited

U.S. PATENT DOCUMENTS

| | | | |
|---|---|---|---|
| 4,601,896 A | 7/1986 | Nugent | |
| 5,593,859 A | 1/1997 | Prockop et al. | |
| 5,962,648 A * | 10/1999 | Berg | 530/356 |
| 6,171,827 B1 * | 1/2001 | Bulleid et al. | 435/69.7 |
| 6,617,431 B1 | 9/2003 | Gruber et al. | |
| 2003/0199441 A1 | 10/2003 | Burchardt | |
| 2006/0217329 A1 * | 9/2006 | Feinstein | 514/44 |
| 2007/0031478 A1 * | 2/2007 | Kadler et al. | 424/445 |

FOREIGN PATENT DOCUMENTS

| | | |
|---|---|---|
| WO | WO 97/08311 | 3/1997 |
| WO | WO 2009/128076 | 10/2009 |

OTHER PUBLICATIONS

Rodero et al. Int J Clin Exp Pathol 2010.*
Barsh G.S., Roush C.L., Bonadio J., Byers P.H., Gelinas R.E. ( "Intron-mediated recombination may cause a deletion in an alpha 1 type I collagen chain in a lethal form of osteogenesis imperfecta." , RL Proc. Natl. Acad. Sci. U.S.A. 82:2870-2874(1985)).*
Meisler et al. "Dexamethasone Abrogates the Fibrogenic Effect of Transforming Growth Factor-β in Rat Granuloma and Granulation Tissue Fibroblasts", Journal of Investigative Dermatology, 108: 285-289, 1997.
Revlon® "Revlon® Renewist™ Lipcolor", product description, 1.P.
Wu et al. "Generation of Collagenase-Resistant Collagen by Site-Directed Mutagenesis of Murine Proα1 (I) Collagen Gene", Proc. Natl. Acad. Sci. USA, 87: 5888-5892, Aug. 1990.
Office Action Dated Apr. 4, 2012 From the Israel Patent Office Re. Application No. 208780 and Its Translation Into English.
International Search Report and the Written Opinion Dated Nov. 30, 2009 From the International Searching Authority Re.: Application No. PCT/IL2009/000419.
Adhirajan et al. "Functionally Modified Gelatin Microspheres Impregnated Collagen Scaffold as Novel Wound Dressing to Attenuate the Proteases and Bacterial Growth", European Journal of Phramaceutical Sciences, 36: 235-245, 2009.
Anonymus "APS Spa Pro-Collagen III: Anti-Aging, Firming, Rejuvenating, Reverse Aging Process", Epicuren Discovery Specialist, XP002554658, Retrieved From the Internet on Nov. 9, 2009. P.2, § 7-10.
Bulleid et al. "Recombinant Expresiion Systems for the Production of Collagen", Biochemical Society Transactions, 28(Pt.4): 350-353, 2000.
Cornwell et al. "Crosslinking of Discrete Self-Assembled Collagen Threads: Effects on Mechanical Strength and Cell-matrix Interactions", Journal of Biomedical Materials Research Part A, 80: 362-371, 2007.
Galeano et al. "Recombinant Human Erythropoietin Stimulates Angiogenesis and Wound Healing in the Genetically Diabetic Mouse", Diabetes, 53(9): 2509-2517, Sep. 2004.
Gallie et al. "The 5'-Leader Sequence of Tobacco Mosaic Virus RNA Enhances the Expression of Foreign Gene Transcripts In Vitro and In Vivo", Nucleic Acids Research, 15(8): 3257-3273, 1987.
Hulmes "Building Collagen Molecules, Fibrils, and Suprafibrillar Structures", Journal of Structural Biology, 137: 2-10, 2002.
Meaney Murray et al. "The Effect of Selected Growth Factors on Human Anterior Cruciate Ligament Cell Interactions With a Three-Dimensional Collagen-GAG Scaffold", Journal of Orthopaedic Research, 21: 238-244, 2003.
Outchkourov et al. "The Promoter-Terminator of Chrysanthemum RbcS1 Directs Very High Expression Levels in Plants", Planta, 216: 1003-1012, 2003.
Qian et al. "Natural Bone Collagen Scaffold Combined With OP-1 for Bone Formation Induction In Vivo", Journal of Biomedical Materials Research, Part B: Applied Biomaterials, 90(2): 778-788, Aug. 2009.
Ulrich et al. "Expression Profile of Proteins Involved in Scar Formation in the Healing Process of Full-Thickness Excisional Wounds in the Porcine Model", Wound Repair and Regeneration, 15: 482-490, 2007.
Wang et al. "The Third Activity for Lysyl Hydroxylase 3: Galactosylation of Hydroxylysyl Residues in Collagens In Vitro", Matrix Biology, 21: 559-566, 2002.

(Continued)

*Primary Examiner* — James H Alstrum Acevedo
*Assistant Examiner* — Li Lee

(57) ABSTRACT

A method of promoting wound healing, treating fibrosis and/or promoting angiogenesis is provided. The method comprises administering to a subject in need thereof a therapeutically effective amount of a procollagen, thereby promoting wound healing, treating fibrosis and/or promoting angiogenesis in the subject.

9 Claims, 8 Drawing Sheets
(8 of 8 Drawing Sheet(s) Filed in Color)

(56) References Cited

OTHER PUBLICATIONS

International Preliminary Report on Patentability Dated Oct. 28, 2010 From International Bureau of WIPO Re. Application No. PCT/IL2009/000419.
Translation of Office Action Dated Oct. 29, 2012 From the State Intellectual Property Office of the People's Republic of China Re. Application No. 200980121650.9.
Ruggiero et al. "Triple Helix Assembly and Processing of Human Collagen Produced in Transgenic Tobacco Plants", FEBS Letters, 469: 132-136, Dec. 31, 2000.
Communications Pursuant to Article 94(3) EPC Dated Jun. 17, 2014 From the European Patent Office Re. Application No. 09733363.7.
Office Action Dated Jul. 17, 2014 From the State Intellectual Property Office of the People's Republic of China Re. Application No. 200980121650.9 and Its Translation Into English.
De Wet et al. "RecName: Full=Collagen Alpha-2(I) Chain; AltName: Full=Alpha-2 Type I Collagen; Flags: Precursor [Homo Sapiens]", Database UniProtKB/Swiss-Prot [Online], GenBank UniProtKB/Swiss-Prot: P08123.7, Database Accession No. P08123, Sep. 3, 2014.
De Wet et al. "RecName: Full=Collagen Alpha-1(I) Chain; AltName: Full=Alpha-1 Type I Collagen; Flags: Precursor [Homo Sapiens] ", Database UniProtKB/Swiss-Prot [Online], GenBank UniProtKB/Swiss-Pro: P02452.5, Database Accession No. P02452, Sep. 3, 2014.
Communications Pursuant to Article 94(3) EPC Dated Dec. 5, 2014 From the European Patent Office Re. Application No. 09733363.7.
Translation of Office Action Dated Jul. 4, 2013 From the State Intellectual Property Office of the People's Republic of China Re. Application No. 200980121650.9.
Translation of Search Report Dated Jul. 4, 2013 From the State Intellectual Property Office of the People's Republic of China Re. Application No. 200980121650.9.
Requisition by the Examiner and Examination Search Report Dated Feb. 18, 2015 From the Canadian Intellectual Property Office Re. Application No. 2,721,507.
Office Action Dated Aug. 11, 2013 From the Israel Patent Office Re. Application No. 208780 and Its Translation Into English.
Merle et al. "Hydroxylated Human Homotrimeric Collagen I in Agrobacterium Tumefaciens-Mediated Transient Expression and in Transgenic Tobacco Plant", FEBS Letters, 515: 114-118, 2002.
Office Action Dated Dec. 23, 2013 From the State Intellectual Property Office of the People's Republic of China Re. Application No. 200980121650.9 and Its Translation Into English.
Search Report Dated Dec. 23, 2013 From the State Intellectual Property Office of the People's Republic of China Re. Application No. 200980121650.9 and Its Translation Into English.
Office Action Dated Aug. 17, 2014 From the Israel Patent Office Re. Application No. 208780 and Its Translation Into English.
Communications Pursuant to Article 94(3) EPC Dated Nov. 22, 2013 From the European Patent Office Re. Application No. 09733363.7.

\* cited by examiner

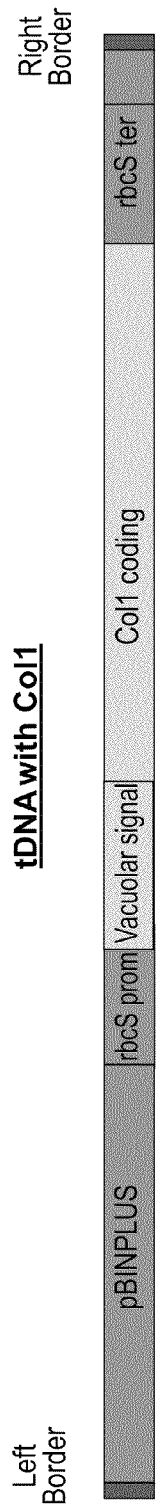
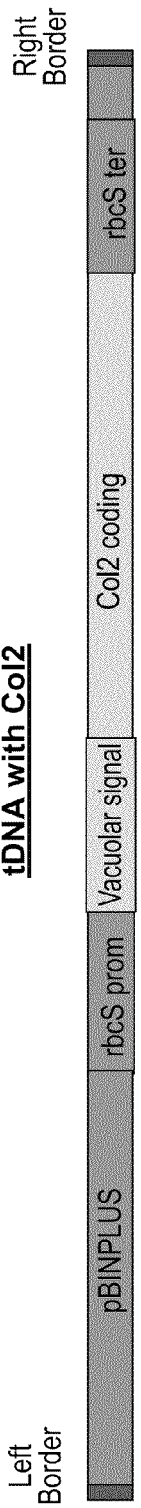
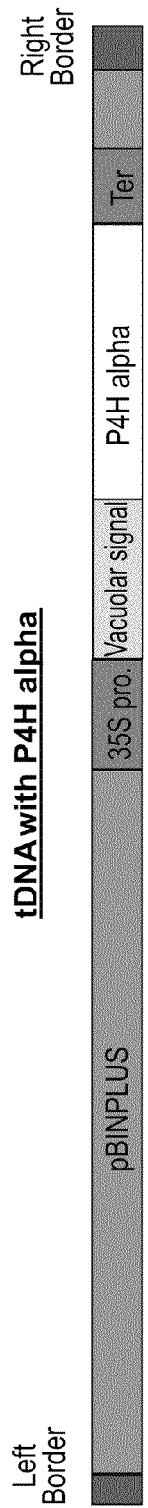
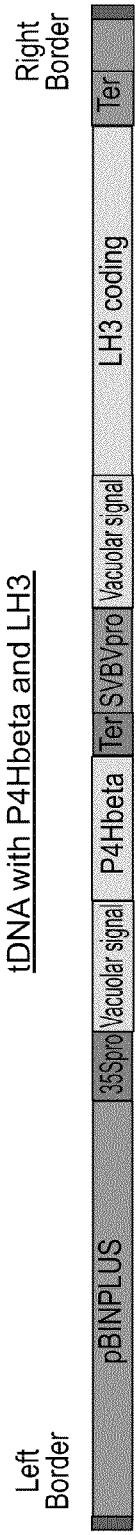
FIG. 1A  tDNA with Col1
FIG. 1B  tDNA with Col2
FIG. 1C  tDNA with P4H alpha
FIG. 1D  tDNA with P4Hbeta and LH3

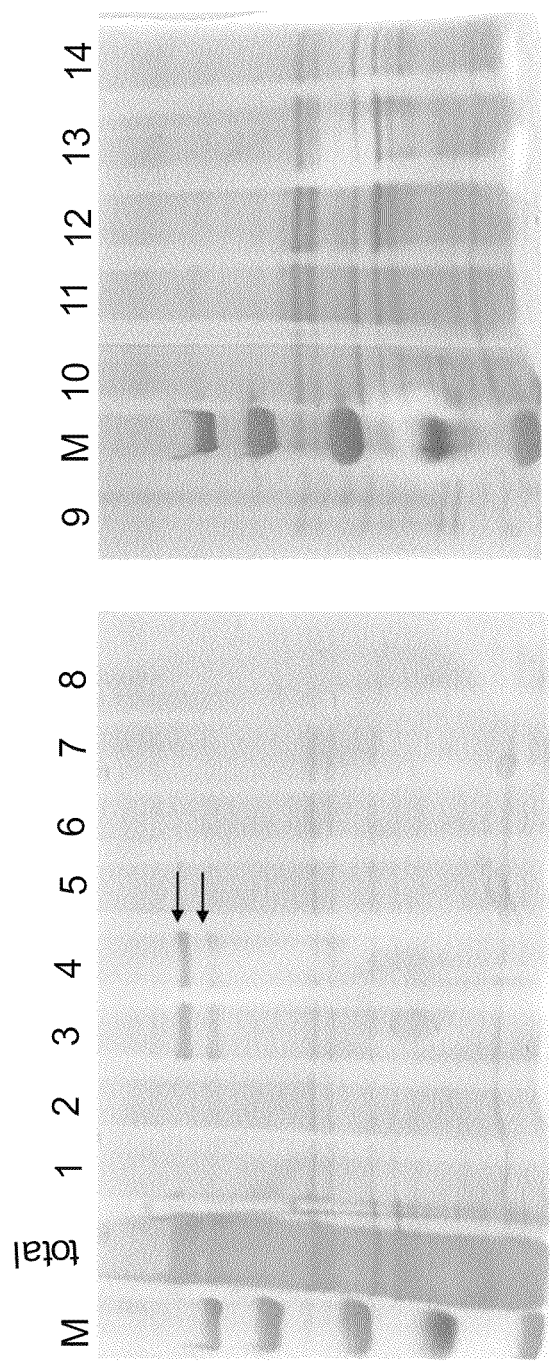

ated self-assembly in vitro, but the resulting fibers lack the natural crosslinks formed in the presence of telopeptides, which are essential for the biomechanical strength of collagen-based tissues.

SEQUENCE LISTING

```
<160> NUMBER OF SEQ ID NOS: 16

<210> SEQ ID NO 1
<211> LENGTH: 1464
<212> TYPE: PRT
<213> ORGANISM: Homo sapiens
<220> FEATURE:
<221> NAME/KEY: misc_feature
<223> OTHER INFORMATION: Alpha 1 type I collagen

<400> SEQUENCE: 1

Met Phe Ser Phe Val Asp Leu Arg Leu Leu Leu Leu Leu Ala Ala Thr
1               5                   10                  15

Ala Leu Leu Thr His Gly Gln Glu Glu Gly Gln Val Glu Gly Gln Asp
                20                  25                  30

Glu Asp Ile Pro Pro Ile Thr Cys Val Gln Asn Gly Leu Arg Tyr His
            35                  40                  45
```

```
Asp Arg Asp Val Trp Lys Pro Glu Pro Cys Arg Ile Cys Val Cys Asp
    50              55                  60
Asn Gly Lys Val Leu Cys Asp Asp Val Ile Cys Asp Glu Thr Lys Asn
65              70                  75                  80
Cys Pro Gly Ala Glu Val Pro Glu Gly Glu Cys Cys Pro Val Cys Pro
                85                  90                  95
Asp Gly Ser Glu Ser Pro Thr Asp Gln Glu Thr Thr Gly Val Glu Gly
            100                 105                 110
Pro Lys Gly Asp Thr Gly Pro Arg Gly Pro Arg Gly Pro Ala Gly Pro
        115                 120                 125
Pro Gly Arg Asp Gly Ile Pro Gly Gln Pro Gly Leu Pro Gly Pro Pro
    130                 135                 140
Gly Pro Pro Gly Pro Pro Gly Pro Pro Gly Leu Gly Gly Asn Phe Ala
145                 150                 155                 160
Pro Gln Leu Ser Tyr Gly Tyr Asp Glu Lys Ser Thr Gly Gly Ile Ser
                165                 170                 175
Val Pro Gly Pro Met Gly Pro Ser Gly Pro Arg Gly Leu Pro Gly Pro
            180                 185                 190
Pro Gly Ala Pro Gly Pro Gln Gly Phe Gln Gly Pro Pro Gly Glu Pro
        195                 200                 205
Gly Glu Pro Gly Ala Ser Gly Pro Met Gly Pro Arg Gly Pro Pro Gly
    210                 215                 220
Pro Pro Gly Lys Asn Gly Asp Asp Gly Glu Ala Gly Lys Pro Gly Arg
225                 230                 235                 240
Pro Gly Glu Arg Gly Pro Pro Gly Pro Gln Gly Ala Arg Gly Leu Pro
                245                 250                 255
Gly Thr Ala Gly Leu Pro Gly Met Lys Gly His Arg Gly Phe Ser Gly
            260                 265                 270
Leu Asp Gly Ala Lys Gly Asp Ala Gly Pro Ala Gly Pro Lys Gly Glu
        275                 280                 285
Pro Gly Ser Pro Gly Glu Asn Gly Ala Pro Gly Gln Met Gly Pro Arg
    290                 295                 300
Gly Leu Pro Gly Glu Arg Gly Arg Pro Gly Ala Pro Gly Pro Ala Gly
305                 310                 315                 320
Ala Arg Gly Asn Asp Gly Ala Thr Gly Ala Ala Gly Pro Pro Gly Pro
                325                 330                 335
Thr Gly Pro Ala Gly Pro Pro Gly Phe Pro Gly Ala Val Gly Ala Lys
            340                 345                 350
Gly Glu Ala Gly Pro Gln Gly Pro Arg Gly Ser Glu Gly Pro Gln Gly
        355                 360                 365
Val Arg Gly Glu Pro Gly Pro Pro Gly Pro Ala Gly Ala Ala Gly Pro
    370                 375                 380
Ala Gly Asn Pro Gly Ala Asp Gly Gln Pro Gly Ala Lys Gly Ala Asn
385                 390                 395                 400
Gly Ala Pro Gly Ile Ala Gly Ala Pro Gly Phe Pro Gly Ala Arg Gly
                405                 410                 415
Pro Ser Gly Pro Gln Gly Pro Gly Pro Gly Pro Lys Gly Asn
            420                 425                 430
Ser Gly Glu Pro Gly Ala Pro Gly Ser Lys Gly Asp Thr Gly Ala Lys
        435                 440                 445
Gly Glu Pro Gly Pro Val Gly Val Gln Gly Pro Pro Gly Pro Ala Gly
    450                 455                 460
```

-continued

```
Glu Gly Lys Arg Gly Ala Arg Gly Glu Pro Gly Thr Gly Leu
465                 470                 475                 480

Pro Gly Pro Pro Gly Glu Arg Gly Gly Pro Gly Ser Arg Gly Phe Pro
                485                 490                 495

Gly Ala Asp Gly Val Ala Gly Pro Lys Gly Pro Ala Gly Glu Arg Gly
            500                 505                 510

Ser Pro Gly Pro Ala Gly Pro Lys Gly Ser Pro Gly Glu Ala Gly Arg
        515                 520                 525

Pro Gly Glu Ala Gly Leu Pro Gly Ala Lys Gly Leu Thr Gly Ser Pro
    530                 535                 540

Gly Ser Pro Gly Pro Asp Gly Lys Thr Gly Pro Pro Gly Pro Ala Gly
545                 550                 555                 560

Gln Asp Gly Arg Pro Gly Pro Pro Gly Pro Pro Gly Ala Arg Gly Gln
                565                 570                 575

Ala Gly Val Met Gly Phe Pro Gly Pro Lys Gly Ala Ala Gly Glu Pro
            580                 585                 590

Gly Lys Ala Gly Glu Arg Gly Val Pro Gly Pro Pro Gly Ala Val Gly
        595                 600                 605

Pro Ala Gly Lys Asp Gly Glu Ala Gly Ala Gln Gly Pro Pro Gly Pro
    610                 615                 620

Ala Gly Pro Ala Gly Glu Arg Gly Glu Gln Gly Pro Ala Gly Ser Pro
625                 630                 635                 640

Gly Phe Gln Gly Leu Pro Gly Pro Ala Gly Pro Pro Gly Glu Ala Gly
                645                 650                 655

Lys Pro Gly Glu Gln Gly Val Pro Gly Asp Leu Gly Ala Pro Gly Pro
            660                 665                 670

Ser Gly Ala Arg Gly Glu Arg Gly Phe Pro Gly Glu Arg Gly Val Gln
        675                 680                 685

Gly Pro Pro Gly Pro Ala Gly Pro Arg Gly Ala Asn Gly Ala Pro Gly
    690                 695                 700

Asn Asp Gly Ala Lys Gly Asp Ala Gly Ala Pro Gly Ala Pro Gly Ser
705                 710                 715                 720

Gln Gly Ala Pro Gly Leu Gln Gly Met Pro Gly Glu Arg Gly Ala Ala
                725                 730                 735

Gly Leu Pro Gly Pro Lys Gly Asp Arg Gly Asp Ala Gly Pro Lys Gly
            740                 745                 750

Ala Asp Gly Ser Pro Gly Lys Asp Gly Val Arg Gly Leu Thr Gly Pro
        755                 760                 765

Ile Gly Pro Pro Gly Pro Ala Gly Ala Pro Gly Asp Lys Gly Glu Ser
    770                 775                 780

Gly Pro Ser Gly Pro Ala Gly Pro Thr Gly Ala Arg Gly Ala Pro Gly
785                 790                 795                 800

Asp Arg Gly Glu Pro Gly Pro Pro Gly Pro Ala Gly Phe Ala Gly Pro
                805                 810                 815

Pro Gly Ala Asp Gly Gln Pro Gly Ala Lys Gly Glu Pro Gly Asp Ala
            820                 825                 830

Gly Ala Lys Gly Asp Ala Gly Pro Pro Gly Pro Ala Gly Pro Ala Gly
        835                 840                 845

Pro Pro Gly Pro Ile Gly Asn Val Gly Ala Pro Gly Ala Lys Gly Ala
    850                 855                 860

Arg Gly Ser Ala Gly Pro Pro Gly Ala Thr Gly Phe Pro Gly Ala Ala
865                 870                 875                 880

Gly Arg Val Gly Pro Pro Gly Pro Ser Gly Asn Ala Gly Pro Pro Gly
```

```
                       885                 890                 895
          Pro Pro Gly Pro Ala Gly Lys Glu Gly Gly Lys Gly Pro Arg Gly Glu
                           900                 905                 910

Thr Gly Pro Ala Gly Arg Pro Gly Glu Val Gly Pro Pro Gly Pro Pro
                       915                 920                 925

Gly Pro Ala Gly Glu Lys Gly Ser Pro Gly Ala Asp Gly Pro Ala Gly
                       930                 935                 940

Ala Pro Gly Thr Pro Gly Pro Gln Gly Ile Ala Gly Gln Arg Gly Val
          945                 950                 955                 960

Val Gly Leu Pro Gly Gln Arg Gly Glu Arg Gly Phe Pro Gly Leu Pro
                           965                 970                 975

Gly Pro Ser Gly Glu Pro Gly Lys Gln Gly Pro Ser Gly Ala Ser Gly
                       980                 985                 990

Glu Arg Gly Pro Pro Gly Pro Met Gly Pro Pro Gly Leu Ala Gly Pro
                           995                1000                1005

Pro Gly Glu Ser Gly Arg Glu Gly Ala Pro Gly Ala Glu Gly Ser
                  1010                1015                1020

Pro Gly Arg Asp Gly Ser Pro Gly Ala Lys Gly Asp Arg Gly Glu
                  1025                1030                1035

Thr Gly Pro Ala Gly Pro Pro Gly Ala Pro Gly Ala Pro Gly Ala
                  1040                1045                1050

Pro Gly Pro Val Gly Pro Ala Gly Lys Ser Gly Asp Arg Gly Glu
                  1055                1060                1065

Thr Gly Pro Ala Gly Pro Ala Gly Pro Val Gly Pro Val Gly Ala
                  1070                1075                1080

Arg Gly Pro Ala Gly Pro Gln Gly Pro Arg Gly Asp Lys Gly Glu
                  1085                1090                1095

Thr Gly Glu Gln Gly Asp Arg Gly Ile Lys Gly His Arg Gly Phe
                  1100                1105                1110

Ser Gly Leu Gln Gly Pro Pro Gly Pro Pro Gly Ser Pro Gly Glu
                  1115                1120                1125

Gln Gly Pro Ser Gly Ala Ser Gly Pro Ala Gly Pro Arg Gly Pro
                  1130                1135                1140

Pro Gly Ser Ala Gly Ala Pro Gly Lys Asp Gly Leu Asn Gly Leu
                  1145                1150                1155

Pro Gly Pro Ile Gly Pro Pro Gly Pro Arg Gly Arg Thr Gly Asp
                  1160                1165                1170

Ala Gly Pro Val Gly Pro Pro Gly Pro Pro Gly Pro Pro Gly Pro
                  1175                1180                1185

Pro Gly Pro Pro Ser Ala Gly Phe Asp Phe Ser Phe Leu Pro Gln
                  1190                1195                1200

Pro Pro Gln Glu Lys Ala His Asp Gly Gly Arg Tyr Tyr Arg Ala
                  1205                1210                1215

Asp Asp Ala Asn Val Val Arg Asp Arg Asp Leu Glu Val Asp Thr
                  1220                1225                1230

Thr Leu Lys Ser Leu Ser Gln Gln Ile Glu Asn Ile Arg Ser Pro
                  1235                1240                1245

Glu Gly Ser Arg Lys Asn Pro Ala Arg Thr Cys Arg Asp Leu Lys
                  1250                1255                1260

Met Cys His Ser Asp Trp Lys Ser Gly Glu Tyr Trp Ile Asp Pro
                  1265                1270                1275

Asn Gln Gly Cys Asn Leu Asp Ala Ile Lys Val Phe Cys Asn Met
                  1280                1285                1290
```

```
Glu Thr Gly Glu Thr Cys Val Tyr Pro Thr Gln Pro Ser Val Ala
    1295                1300                1305

Gln Lys Asn Trp Tyr Ile Ser Lys Asn Pro Lys Asp Lys Arg His
    1310                1315                1320

Val Trp Phe Gly Glu Ser Met Thr Asp Gly Phe Gln Phe Glu Tyr
    1325                1330                1335

Gly Gly Gln Gly Ser Asp Pro Ala Asp Val Ala Ile Gln Leu Thr
    1340                1345                1350

Phe Leu Arg Leu Met Ser Thr Glu Ala Ser Gln Asn Ile Thr Tyr
    1355                1360                1365

His Cys Lys Asn Ser Val Ala Tyr Met Asp Gln Gln Thr Gly Asn
    1370                1375                1380

Leu Lys Lys Ala Leu Leu Leu Gln Gly Ser Asn Glu Ile Glu Ile
    1385                1390                1395

Arg Ala Glu Gly Asn Ser Arg Phe Thr Tyr Ser Val Thr Val Asp
    1400                1405                1410

Gly Cys Thr Ser His Thr Gly Ala Trp Gly Lys Thr Val Ile Glu
    1415                1420                1425

Tyr Lys Thr Thr Lys Thr Ser Arg Leu Pro Ile Ile Asp Val Ala
    1430                1435                1440

Pro Leu Asp Val Gly Ala Pro Asp Gln Glu Phe Gly Phe Asp Val
    1445                1450                1455

Gly Pro Val Cys Phe Leu
    1460

<210> SEQ ID NO 2
<211> LENGTH: 1366
<212> TYPE: PRT
<213> ORGANISM: Homo sapiens
<220> FEATURE:
<221> NAME/KEY: misc_feature
<223> OTHER INFORMATION: Alpha 2 type I collagen

<400> SEQUENCE: 2

Met Leu Ser Phe Val Asp Thr Arg Thr Leu Leu Leu Leu Ala Val Thr
1               5                   10                  15

Leu Cys Leu Ala Thr Cys Gln Ser Leu Gln Glu Glu Thr Val Arg Lys
                20                  25                  30

Gly Pro Ala Gly Asp Arg Gly Pro Arg Gly Glu Arg Gly Pro Pro Gly
            35                  40                  45

Pro Pro Gly Arg Asp Gly Glu Asp Gly Pro Thr Gly Pro Pro Gly Pro
        50                  55                  60

Pro Gly Pro Pro Gly Pro Pro Gly Leu Gly Gly Asn Phe Ala Ala Gln
65                  70                  75                  80

Tyr Asp Gly Lys Gly Val Gly Leu Gly Pro Gly Pro Met Gly Leu Met
                85                  90                  95

Gly Pro Arg Gly Pro Pro Gly Ala Ala Gly Ala Pro Gly Pro Gln Gly
            100                 105                 110

Phe Gln Gly Pro Ala Gly Glu Pro Gly Glu Pro Gly Gln Thr Gly Pro
        115                 120                 125

Ala Gly Ala Arg Gly Pro Ala Gly Pro Pro Gly Lys Ala Gly Glu Asp
    130                 135                 140

Gly His Pro Gly Lys Pro Gly Arg Pro Gly Glu Arg Gly Val Val Gly
145                 150                 155                 160

Pro Gln Gly Ala Arg Gly Phe Pro Gly Thr Pro Gly Leu Pro Gly Phe
```

```
                165                 170                 175
Lys Gly Ile Arg Gly His Asn Gly Leu Asp Gly Leu Lys Gly Gln Pro
            180                 185                 190
Gly Ala Pro Gly Val Lys Gly Glu Pro Gly Ala Pro Gly Glu Asn Gly
            195                 200                 205
Thr Pro Gly Gln Thr Gly Ala Arg Gly Leu Pro Gly Glu Arg Gly Arg
    210                 215                 220
Val Gly Ala Pro Gly Pro Ala Gly Ala Arg Gly Ser Asp Gly Ser Val
225                 230                 235                 240
Gly Pro Val Gly Pro Ala Gly Pro Ile Gly Ser Ala Gly Pro Pro Gly
            245                 250                 255
Phe Pro Gly Ala Pro Gly Pro Lys Gly Glu Ile Gly Ala Val Gly Asn
            260                 265                 270
Ala Gly Pro Ala Gly Pro Ala Gly Pro Arg Gly Glu Val Gly Leu Pro
            275                 280                 285
Gly Leu Ser Gly Pro Val Gly Pro Pro Gly Asn Pro Gly Ala Asn Gly
            290                 295                 300
Leu Thr Gly Ala Lys Gly Ala Ala Gly Leu Pro Gly Val Ala Gly Ala
305                 310                 315                 320
Pro Gly Leu Pro Gly Pro Arg Gly Ile Pro Gly Pro Val Gly Ala Ala
            325                 330                 335
Gly Ala Thr Gly Ala Arg Gly Leu Val Gly Glu Pro Gly Pro Ala Gly
            340                 345                 350
Ser Lys Gly Glu Ser Gly Asn Lys Gly Glu Pro Gly Ser Ala Gly Pro
            355                 360                 365
Gln Gly Pro Pro Gly Pro Ser Gly Glu Glu Gly Lys Arg Gly Pro Asn
    370                 375                 380
Gly Glu Ala Gly Ser Ala Gly Pro Pro Gly Pro Pro Gly Leu Arg Gly
385                 390                 395                 400
Ser Pro Gly Ser Arg Gly Leu Pro Gly Ala Asp Gly Arg Ala Gly Val
            405                 410                 415
Met Gly Pro Pro Gly Ser Arg Gly Ala Ser Gly Pro Ala Gly Val Arg
            420                 425                 430
Gly Pro Asn Gly Asp Ala Gly Arg Pro Gly Glu Pro Gly Leu Met Gly
            435                 440                 445
Pro Arg Gly Leu Pro Gly Ser Pro Gly Asn Ile Gly Pro Ala Gly Lys
    450                 455                 460
Glu Gly Pro Val Gly Leu Pro Gly Ile Asp Gly Arg Pro Gly Pro Ile
465                 470                 475                 480
Gly Pro Ala Gly Ala Arg Gly Glu Pro Gly Asn Ile Gly Phe Pro Gly
            485                 490                 495
Pro Lys Gly Pro Thr Gly Asp Pro Gly Lys Asn Gly Asp Lys Gly His
            500                 505                 510
Ala Gly Leu Ala Gly Ala Arg Gly Ala Pro Gly Pro Asp Gly Asn Asn
            515                 520                 525
Gly Ala Gln Gly Pro Pro Gly Pro Gln Gly Val Gln Gly Gly Lys Gly
            530                 535                 540
Glu Gln Gly Pro Ala Gly Pro Pro Gly Phe Gln Gly Leu Pro Gly Pro
545                 550                 555                 560
Ser Gly Pro Ala Gly Glu Val Gly Lys Pro Gly Glu Arg Gly Leu His
            565                 570                 575
Gly Glu Phe Gly Leu Pro Gly Pro Ala Gly Pro Arg Gly Glu Arg Gly
            580                 585                 590
```

```
Pro Pro Gly Glu Ser Gly Ala Ala Gly Pro Thr Gly Pro Ile Gly Ser
        595                 600                 605

Arg Gly Pro Ser Gly Pro Pro Gly Pro Asp Gly Asn Lys Gly Glu Pro
    610                 615                 620

Gly Val Val Gly Ala Val Gly Thr Ala Gly Pro Ser Gly Pro Ser Gly
625                 630                 635                 640

Leu Pro Gly Glu Arg Gly Ala Ala Gly Ile Pro Gly Gly Lys Gly Glu
                645                 650                 655

Lys Gly Glu Pro Gly Leu Arg Gly Glu Ile Gly Asn Pro Gly Arg Asp
            660                 665                 670

Gly Ala Arg Gly Ala Pro Gly Ala Val Gly Ala Pro Gly Pro Ala Gly
        675                 680                 685

Ala Thr Gly Asp Arg Gly Glu Ala Gly Ala Ala Gly Pro Ala Gly Pro
    690                 695                 700

Ala Gly Pro Arg Gly Ser Pro Gly Glu Arg Gly Glu Val Gly Pro Ala
705                 710                 715                 720

Gly Pro Asn Gly Phe Ala Gly Pro Ala Gly Ala Ala Gly Gln Pro Gly
                725                 730                 735

Ala Lys Gly Glu Arg Gly Ala Lys Gly Pro Lys Gly Glu Asn Gly Val
            740                 745                 750

Val Gly Pro Thr Gly Pro Val Gly Ala Ala Gly Pro Ala Gly Pro Asn
        755                 760                 765

Gly Pro Pro Gly Pro Ala Gly Ser Arg Gly Asp Gly Gly Pro Pro Gly
    770                 775                 780

Met Thr Gly Phe Pro Gly Ala Ala Gly Arg Thr Gly Pro Pro Gly Pro
785                 790                 795                 800

Ser Gly Ile Ser Gly Pro Pro Gly Pro Pro Gly Ala Gly Lys Glu
                805                 810                 815

Gly Leu Arg Gly Pro Arg Gly Asp Gln Gly Pro Val Gly Arg Thr Gly
            820                 825                 830

Glu Val Gly Ala Val Gly Pro Pro Gly Phe Ala Gly Glu Lys Gly Pro
        835                 840                 845

Ser Gly Glu Ala Gly Thr Ala Gly Pro Pro Gly Thr Pro Gly Pro Gln
    850                 855                 860

Gly Leu Leu Gly Ala Pro Gly Ile Leu Gly Leu Pro Gly Ser Arg Gly
865                 870                 875                 880

Glu Arg Gly Leu Pro Gly Val Ala Gly Ala Val Gly Glu Pro Gly Pro
                885                 890                 895

Leu Gly Ile Ala Gly Pro Pro Gly Ala Arg Gly Pro Pro Gly Ala Val
            900                 905                 910

Gly Ser Pro Gly Val Asn Gly Ala Pro Gly Glu Ala Gly Arg Asp Gly
        915                 920                 925

Asn Pro Gly Asn Asp Gly Pro Pro Gly Arg Asp Gly Gln Pro Gly His
    930                 935                 940

Lys Gly Glu Arg Gly Tyr Pro Gly Asn Ile Gly Pro Val Gly Ala Ala
945                 950                 955                 960

Gly Ala Pro Gly Pro His Gly Pro Val Gly Pro Ala Gly Lys His Gly
                965                 970                 975

Asn Arg Gly Glu Thr Gly Pro Ser Gly Pro Val Gly Pro Ala Gly Ala
            980                 985                 990

Val Gly Pro Arg Gly Pro Ser Gly  Pro Gln Gly Ile Arg  Gly Asp Lys
        995                 1000                1005
```

Gly Glu Pro Gly Glu Lys Gly Pro Arg Gly Leu Pro Gly Leu Lys
    1010                1015                1020

Gly His Asn Gly Leu Gln Gly Leu Pro Gly Ile Ala Gly His His
    1025                1030                1035

Gly Asp Gln Gly Ala Pro Gly Ser Val Gly Pro Ala Gly Pro Arg
    1040                1045                1050

Gly Pro Ala Gly Pro Ser Gly Pro Ala Gly Lys Asp Gly Arg Thr
    1055                1060                1065

Gly His Pro Gly Thr Val Gly Pro Ala Gly Ile Arg Gly Pro Gln
    1070                1075                1080

Gly His Gln Gly Pro Ala Gly Pro Pro Gly Pro Pro Gly Pro Pro
    1085                1090                1095

Gly Pro Pro Gly Val Ser Gly Gly Gly Tyr Asp Phe Gly Tyr Asp
    1100                1105                1110

Gly Asp Phe Tyr Arg Ala Asp Gln Pro Arg Ser Ala Pro Ser Leu
    1115                1120                1125

Arg Pro Lys Asp Tyr Glu Val Asp Ala Thr Leu Lys Ser Leu Asn
    1130                1135                1140

Asn Gln Ile Glu Thr Leu Leu Thr Pro Glu Gly Ser Arg Lys Asn
    1145                1150                1155

Pro Ala Arg Thr Cys Arg Asp Leu Arg Leu Ser His Pro Glu Trp
    1160                1165                1170

Ser Ser Gly Tyr Tyr Trp Ile Asp Pro Asn Gln Gly Cys Thr Met
    1175                1180                1185

Asp Ala Ile Lys Val Tyr Cys Asp Phe Ser Thr Gly Glu Thr Cys
    1190                1195                1200

Ile Arg Ala Gln Pro Glu Asn Ile Pro Ala Lys Asn Trp Tyr Arg
    1205                1210                1215

Ser Ser Lys Asp Lys Lys His Val Trp Leu Gly Glu Thr Ile Asn
    1220                1225                1230

Ala Gly Ser Gln Phe Glu Tyr Asn Val Glu Gly Val Thr Ser Lys
    1235                1240                1245

Glu Met Ala Thr Gln Leu Ala Phe Met Arg Leu Leu Ala Asn Tyr
    1250                1255                1260

Ala Ser Gln Asn Ile Thr Tyr His Cys Lys Asn Ser Ile Ala Tyr
    1265                1270                1275

Met Asp Glu Glu Thr Gly Asn Leu Lys Lys Ala Val Ile Leu Gln
    1280                1285                1290

Gly Ser Asn Asp Val Glu Leu Val Ala Glu Gly Asn Ser Arg Phe
    1295                1300                1305

Thr Tyr Thr Val Leu Val Asp Gly Cys Ser Lys Lys Thr Asn Glu
    1310                1315                1320

Trp Gly Lys Thr Ile Ile Glu Tyr Lys Thr Asn Lys Pro Ser Arg
    1325                1330                1335

Leu Pro Phe Leu Asp Ile Ala Pro Leu Asp Ile Gly Gly Ala Asp
    1340                1345                1350

Gln Glu Phe Phe Val Asp Ile Gly Pro Val Cys Phe Lys
    1355                1360                1365

<210> SEQ ID NO 3
<211> LENGTH: 5927
<212> TYPE: DNA
<213> ORGANISM: Homo sapiens
<220> FEATURE:
<221> NAME/KEY: misc_feature
<223> OTHER INFORMATION: Collagen, type I, alpha 1 (COL1A1), mRNA

<400> SEQUENCE: 3

| | |
|---|---|
| tcgtcggagc agacgggagt ttctcctcgg ggtcggagca ggaggcacgc ggagtgtgag | 60 |
| gccacgcatg agcggacgct aaccccctcc ccagccacaa agagtctaca tgtctagggt | 120 |
| ctagacatgt tcagctttgt ggacctccgg ctcctgctcc tcttagcggc caccgccctc | 180 |
| ctgacgcacg ccaagagga aggccaagtc gagggccaag acgaagacat cccaccaatc | 240 |
| acctgcgtac agaacggcct caggtaccat gaccgagacg tgtggaaacc cgagccctgc | 300 |
| cggatctgcg tctgcgacaa cggcaaggtg ttgtgcgatg acgtgatctg tgacgagacc | 360 |
| aagaactgcc ccggcgccga agtccccgag ggcgagtgct gtcccgtctg ccccgacggc | 420 |
| tcagagtcac ccaccgacca agaaaccacc ggcgtcgagg gacccaaggg agacactggc | 480 |
| ccccgaggcc caaggggacc cgcaggcccc cctggccgag atggcatccc tggacagcct | 540 |
| ggacttcccg acccccccgg accccccgga cctcccggac ccctggcct cggaggaaac | 600 |
| tttgctcccc agctgtctta tggctatgat gagaaatcaa ccggaggaat ttccgtgcct | 660 |
| ggccccatgg gtccctctgg tcctcgtggt ctccctggcc ccctggtgc acctggtccc | 720 |
| caaggcttcc aaggtccccc tggtgagcct ggcgagcctg gagcttcagg tcccatgggt | 780 |
| ccccgaggtc ccccaggtcc ccctggaaag aatggagatg atggggaagc tggaaaacct | 840 |
| ggtcgtcctg gtgagcgtgg ggcctcctgg cctcaggggt ctcgaggatt gcccggaaca | 900 |
| gctggcctcc ctggaatgaa gggacacaga ggtttcagtg gtttggatgg tgccaaggga | 960 |
| gatgctggtc ctgctggtcc taagggtgag cctggcagcc ctggtgaaaa tggagctcct | 1020 |
| ggtcagatgg gccccgtgg cctgcctggt gagagaggtc gccctggagc ccctggccct | 1080 |
| gctggtgctc gtgaaatga tggtgctact ggtgctgccg gccccctgg tcccaccggc | 1140 |
| cccgctggtc ctcctggctt cctggtgct gttggtgcta agggtgaagc tggtccccaa | 1200 |
| gggccccgag gctctgaagg tccccagggt gtgcgtggtg agcctggccc cctggcccct | 1260 |
| gctggtgctg ctggccctgc tggaaaccct ggtgctgatg gacagcctgg tgctaaaggt | 1320 |
| gccaatggtg ctcctggtat tgctggtgct cctggcttcc ctggtgcccg aggcccctct | 1380 |
| ggaccccagg ccccggcgg ccctcctggt cccaaggta acagcggtga acctggtgct | 1440 |
| cctggcagca aaggagacac tggtgctaag ggagagcctg gcctgttgg tgttcaagga | 1500 |
| ccccctggcc ctgctggaga ggaaggaaag cgaggagctc gaggtgaacc cggacccact | 1560 |
| ggcctgcccg acccctggg cgagcgtggt ggacctggta gccgtggttt ccctggcgca | 1620 |
| gatggtgttg ctggtcccaa gggtcccgct ggtgaacgtg gttctcctgg ccctgctggc | 1680 |
| cccaaaggat ctcctggtga agctggtcgt cccggtgaag ctggtctgcc tggtgccaag | 1740 |
| ggtctgactg gaagccctgg cagccctggt cctgatggca aaactggccc cctggtcccc | 1800 |
| gccggtcaag atggtcgccc cggaccccca ggcccacctg tgcccgtgg tcaggctggt | 1860 |
| gtgatgggat tccctggacc taaaggtgct gctgagagc cggcaaggc tggagagcga | 1920 |
| ggtgttcccg accccctgg cgctgtcggt cctgctggca aagatggaga ggctggagct | 1980 |
| cagggacccc ctgccctgc tggtccgct ggcgagagag gtgaacaagg ccctgctggc | 2040 |
| tcccccggat tccagggtct ccctggtcct gctggtcctc aggtgaagc aggcaaacct | 2100 |
| ggtgaacagg gtgttcctgg agaccttggc gccctggcc cctctggagc aagaggcgag | 2160 |
| agaggttttcc ctgcgagcg tggtgtgcaa ggtccccctg gtcctgctgg tccccgaggg | 2220 |
| gccaacggtg ctcccggcaa cgatggtgct aagggtgatg ctggtgcccc tggagctccc | 2280 |

```
ggtagccagg gcgcccctgg ccttcaggga atgcctggtg aacgtggtgc agctggtctt    2340
ccagggccta agggtgacag aggtgatgct ggtcccaaag gtgctgatgg ctctcctggc    2400
aaagatggcg tccgtggtct gactggcccc attggtcctc ctggccctgc tggtgcccct    2460
ggtgacaagg gtgaaagtgg tcccagcggc cctgctggtc ccactggagc tcgtggtgcc    2520
cccggagacc gtggtgagcc tggtcccccc ggccctgctg gctttgctgg ccccctggt    2580
gctgacggcc aacctggtgc taaaggcgaa cctggtgatg ctggtgctaa aggcgatgct    2640
ggtcccctg ccctgccgg acccgctgga ccccctggcc ccattggtaa tgttggtgct     2700
cctggagcca aggtgctcg cggcagcgct ggtcccctg gtgctactgg tttccctggt     2760
gctgctggcc gagtcggtcc tcctggcccc tctggaaatg ctggacccc tggccctcct    2820
ggtcctgctg gcaaagaagg cggcaaaggt cccgtggtg agactggccc tgctggacgt    2880
cctggtgaag ttggtccccc tggtccccct ggccctgctg gcgagaaagg atcccctggt    2940
gctgatggtc ctgctggtgc tcctggtact cccgggcctc aaggtattgc tggacagcgt    3000
ggtgtggtcg gcctgcctgg tcagagagga gagagaggct ccctggtct tcctggcccc    3060
tctggtgaac ctggcaaaca aggtccctct ggagcaagtg gtgaacgtgg tcccctggt     3120
cccatgggcc cccctggatt ggctggaccc cctggtgaat ctggacgtga ggggctcct    3180
ggtgccgaag ttcccctgg acgagacggt tctcctggcg ccaagggtga ccgtggtgag    3240
accggccccg ctgaccccc tggtgctcct ggtgctcct gtgcccctgg cccgttggc      3300
cctgctggca agagtggtga tcgtggtgag actggtcctg ctggtcccgc cggtcctgtc    3360
ggccctgttg gcgcccgtgg ccccgccgga ccccaaggcc ccgtggtga caagggtgag    3420
acaggcgaac agggcgacag aggcataaag ggtcaccgtg gcttctctgg cctccaggt     3480
ccccctggcc ctcctggctc tcctggtgaa caaggtccct ctggagcctc tggtcctgct    3540
ggtccccgag gtcccctgg ctctgctggt gctcctggca agatggact caacggtctc      3600
cctggcccca ttgggccccc tggtcctcgc ggtcgcactg gtgatgctgg tctgttggt     3660
ccccccggcc ctcctggacc tcctggtccc cctggtcctc ccagcgctgg tttcgacttc    3720
agcttcctgc cccagccacc tcaagagaag gctcacgatg gtggccgcta ctaccggct     3780
gatgatgcca atgtggttcg tgaccgtgac ctcgaggtgg acaccaccct caagagcctg    3840
agccagcaga tcgagaacat ccggagccca gagggcagcc gcaagaaccc cgcccgcacc    3900
tgccgtgacc tcaagatgtg ccactctgac tggaagagtg gagagtactg gattgacccc    3960
aaccaaggct gcaacctgga tgccatcaaa gtcttctgca acatggagac tggtgagacc    4020
tgcgtgtacc ccactcagcc cagtgtggcc cagaagaact ggtacatcag caagaacccc    4080
aaggacaaga ggcatgtctg gttcggcgag agcatgaccg atggattcca gttcgagtat    4140
ggcggccagg gctccgaccc tgccgatgtg ccatccagc tgaccttcct cgcctgatg      4200
tccaccgagg cctcccagaa catcacctac cactgcaaga cagcgtggc ctacatggac    4260
cagcagactg gcaacctcaa gaaggccctg ctcctccagg gctccaacga gatcgagatc   4320
cgcgccgagg gcaacagccg cttcacctac agcgtcactg tcgatggctg cacgagtcac   4380
accggagcct ggggcaagac agtgattgaa tacaaaacca ccaagacctc ccgcctgccc    4440
atcatcgatg tggccccctt ggacgttggt gccccagacc aggaattcgg cttcgacgtt    4500
ggccctgtct gcttcctgta aactcccctcc atcccaacct ggctccctcc cacccaacca   4560
actttccccc caacccggaa acagacaagc aacccaaact gaaccccctc aaaagccaaa    4620
```

| | | | | |
|---|---|---|---|---|
| aaatgggaga | caatttcaca | tggactttgg | aaaatatttt | tttcctttgc attcatctct | 4680 |
| caaacttagt | ttttatcttt | gaccaaccga | acatgaccaa | aaaccaaaag tgcattcaac | 4740 |
| cttaccaaaa | aaaaaaaaaa | aaaagaata | aataaataac | ttttaaaaa aggaagcttg | 4800 |
| gtccacttgc | ttgaagaccc | atgcgggggt | aagtcccttt | ctgcccgttg ggcttatgaa | 4860 |
| accccaatgc | tgcccttcct | gctcctttct | ccacaccccc | cttggggcct cccctccact | 4920 |
| ccttcccaaa | tctgtctccc | cagaagacac | aggaaacaat | gtattgtctg cccagcaatc | 4980 |
| aaaggcaatg | ctcaaacacc | caagtggccc | ccaccctcag | cccgctcctg cccgcccagc | 5040 |
| accccaggc | cctggggac | ctggggttct | cagactgcca | aagaagcctt gccatctggc | 5100 |
| gctcccatgg | ctcttgcaac | atctcccctt | cgttttgag | ggggtcatgc cgggggagcc | 5160 |
| accagcccct | cactgggttc | ggaggagagt | caggaagggc | cacgacaaag cagaaacatc | 5220 |
| ggatttgggg | aacgcgtgtc | aatcccttgt | gccgcagggc | tgggcgggag agactgttct | 5280 |
| gttccttgtg | taactgtgtt | gctgaaagac | tacctcgttc | ttgtcttgat gtgtcaccgg | 5340 |
| ggcaactgcc | tggggcggg | gatgggggca | gggtggaagc | ggctccccat tttataccaa | 5400 |
| aggtgctaca | tctatgtgat | gggtgggtg | ggagggaat | cactggtgct atagaaattg | 5460 |
| agatgccccc | ccaggccagc | aaatgttcct | ttttgttcaa | agtctatttt tattccttga | 5520 |
| tatttttctt | ttttttttt | ttttttgtg | gatgggggact | tgtgaatttt tctaaaggtg | 5580 |
| ctatttaaca | tgggaggaga | gcgtgtgcgg | ctccagccca | gccgctgct cactttccac | 5640 |
| cctctctcca | cctgcctctg | gcttctcagg | cctctgctct | ccgacctctc tcctctgaaa | 5700 |
| ccctcctcca | cagctgcagc | ccatcctccc | ggctccctcc | tagtctgtcc tgcgtcctct | 5760 |
| gtccccgggt | ttcagagaca | acttcccaaa | gcacaaagca | gtttttcccc ctaggggtgg | 5820 |
| gaggaagcaa | aagactctgt | acctatttg | tatgtgtata | ataatttgag atgttttaa | 5880 |
| ttattttgat | tgctggaata | aagcatgtgg | aaatgaccca | aacataa | 5927 |

<210> SEQ ID NO 4
<211> LENGTH: 5411
<212> TYPE: DNA
<213> ORGANISM: Homo sapiens
<220> FEATURE:
<221> NAME/KEY: misc_feature
<223> OTHER INFORMATION: Collagen, type I, alpha 2 (COL1A2), mRNA

<400> SEQUENCE: 4

| | | | | |
|---|---|---|---|---|
| gtgtcccata | gtgttccaa | acttggaaag | ggcggggag | ggcgggagga tgcggagggc | 60 |
| ggaggtatgc | agacaacgag | tcagagtttc | cccttgaaag | cctcaaaagt gtccacgtcc | 120 |
| tcaaaaagaa | tggaaccaat | ttaagaagcc | agcccgtgg | ccacgtccct tcccccattc | 180 |
| gctccctcct | ctgcgccccc | gcaggctcct | cccagctgtg | gctgcccggg ccccagccc | 240 |
| cagccctccc | attggtggag | gcccttttgg | aggcacccta | gggccaggga aacttttgcc | 300 |
| gtataaatag | ggcagatccg | ggcttttatta | ttttagcacc | acggcagcag gaggtttcgg | 360 |
| ctaagttgga | ggtactggcc | acgactgcat | gcccgcgccc | gccaggtgat acctccgccg | 420 |
| gtgacccagg | ggctctgcga | cacaaggagt | ctgcatgtct | aagtgctaga catgctcagc | 480 |
| tttgtggata | cgcggacttt | gttgctgctt | gcagtaacct | tatgcctagc aacatgccaa | 540 |
| tcttttacaag | aggaaactgt | aagaaagggc | ccagccggag | atagaggacc acgtggagaa | 600 |
| aggggtccac | caggccccc | aggcagagat | ggtgaagatg | gtcccacagg ccctcctggt | 660 |
| ccacctggtc | ctcctggccc | ccctggtctc | ggtgggaact | tgctgctca gtatgatgga | 720 |

```
aaaggagttg gacttggccc tggaccaatg ggcttaatgg gacctagagg cccacctggt      780
gcagctggag ccccaggccc tcaaggtttc caaggacctg ctggtgagcc tggtgaacct      840
ggtcaaactg gtcctgcagg tgctcgtggt ccagctggcc tcctggcaa ggctggtgaa       900 gatggtcacc ctggaaaacc cggacgacct ggtgagagag gagttgttgg accacagggt      960
gctcgtggtt tccctggaac tcctggactt cctggcttca aaggcattag gggacacaat     1020
ggtctgatgg gattgaaggg acagcccggt gctcctggtg tgaagggtga acctggtgcc     1080
cctggtgaaa atggaactcc aggtcaaaca ggagcccgtg gcttcctgg tgagagagga      1140 cgtgttggtg ccctggccc agctggtgcc cgtggcagta tggaagtgt gggtcccgtg       1200 ggtcctgctg gtcccattgg gtctgctggc cctccaggct cccaggtgc ccctggcccc     1260 aagggtgaaa ttggagctgt tggtaacgct ggtcctgctg gtcccgccgg tccccgtggt     1320
gaagtgggtc ttccaggcct ctccggcccc gttggacctc ctggtaatcc tggagcaaac     1380
ggccttactg gtgccaaggg tgctgctggc cttccggcg ttgctgggc tcccggcctc      1440 cctggacccc gcggtattcc tggccctgtt ggtgctgccg tgctactgg tgccagagga     1500 cttgttggtg agcctggtcc agctggctcc aaaggagaga gcggtaacaa gggtgagccc     1560
ggctctgctg ggccccaagg tcctcctggt cccagtggtg aagaaggaaa gagaggccct     1620
aatggggaag ctggatctgc cggccctcca ggacctcctg ggctgagagg tagtcctggt     1680
tctcgtggtc ttcctggagc tgatggcaga gctggcgtca tgggccctcc tggtagtcgt     1740
ggtgcaagtg gccctgctgg agtccgagga cctaatggag atgctggtcg ccctggggag     1800
cctggtctca tgggacccag aggtcttcct ggttcccctg gaaatatcgg ccccgctgga     1860
aaagaaggtc ctgtcggcct ccctggcatc gacggcaggc ctggcccaat tggcccagct     1920
ggagcaagag gagagcctgg caacattgga ttccctggac ccaaaggccc cactggtgat     1980
cctggcaaaa acggtgataa aggtcatgct ggtcttgctg gtgctcgggg tgctccaggt     2040
cctgatggaa caatggtgc tcagggacct cctggaccac agggtgttca agtggaaaa      2100 ggtgaacagg gtcccctgg tcctccaggc ttcagggtc tgcctggccc tcaggtccc       2160 gctggtgaag ttggcaaacc aggagaaaag ggtctccatg gtgagtttgg tctccctggt     2220
cctgctggtc caagagggga acgcggtccc ccaggtgaga gtggtgctgc cggtcctact     2280
ggtcctattg gaagccgagg tccttctgga ccccagggc tgatggaaa caagggtgaa      2340 cctggtgtgg ttggtgctgt gggcactgct ggtccatctg gtcctagtgg actcccagga     2400 gagagggggtc ctgctggcat acctggaggc aagggagaaa aggtgaacc tggtctcaga     2460 ggtgaaattg gtaaccctgg cagagatggt gctcgtggtg ctcctggtgc tgtaggtgcc     2520
cctggtcctg ctggagccac aggtgaccgg ggcgaagctg gggctgctgg tcctgctggt     2580
cctgctggtc ctcggggaag ccctggtgaa cgtggtgagg tcggtcctgc tggccccaat     2640
ggatttgctg gtcctgctgg tgctgctggt caacctggtg ctaaaggaga aagaggagcc     2700
aaagggccta agggtgaaaa cggtgttgtt ggtcccacag gccccgttgg agctgctggc     2760
ccagctggtc caaatggtcc ccccggtcct gctggaagtc gtggtgatgg aggcccccct     2820
ggtatgactg gttccctgg tgctgctgga cggactggtc cccaggacc tctggtatt       2880 tctggccctc ctggtccccc tggtcctgct gggaagaag gcttcgtgg tcctcgtggt     2940 gaccaaggtc cagttggccg aactggagaa gtaggtgcag ttggtccccc tggcttcgct     3000
ggtgagaagg gtccctctgg agaggctggt actgctggac ctcctggcac tccaggtcct     3060
cagggtcttc ttggtgctcc tggtattctg ggtctccctg gctcgagagg tgaacgtggt     3120
```

```
ctaccaggtg ttgctggtgc tgtgggtgaa cctggtcctc ttggcattgc cggccctcct    3180
ggggcccgtg gtcctcctgg tgctgtgggt agtcctggag tcaacggtgc tcctggtgaa    3240
gctggtcgtg atggcaaccc tgggaacgat ggtccccag gtcgcgatgg tcaacccgga     3300
cacaagggag agcgcggtta ccctggcaat attggtcccg ttggtgctgc aggtgcacct    3360
ggtcctcatg gccccgtggg tcctgctggc aaacatggaa accgtggtga actggtcct    3420 tctggtcctg ttggtcctgc tggtgctgtt ggcccaagag gtcctagtgg cccacaaggc    3480
attcgtggcg ataagggaga gcccggtgaa aggggcccca gaggtcttcc tggcttaaag    3540
ggacacaatg gattgcaagg tctgcctggt atcgctggtc accatggtga tcaaggtgct    3600
cctggctccg tgggtcctgc tggtcctagg ggccctgctg gtccttctgg ccctgctgga    3660
aaagatggtc gcactggaca tcctggtaca gttggacctg ctggcattcg aggccctcag    3720
ggtcaccaag gccctgctgg ccccctggt ccccctggcc ctcctggacc tccaggtgta    3780
agcggtggtg gttatgactt tggttacgat ggagacttct acagggctga ccagcctcgc    3840
tcagcacctt ctctcagacc caaggactat gaagttgatg ctactctgaa gtctctcaac    3900
aaccagattg agacccttct tactcctgaa ggctctagaa agaacccagc tcgcacatgc    3960
cgtgacttga gactcagcca cccagagtgg agcagtggtt actactggat tgaccctaac    4020
caaggatgca ctatgatgc tatcaaagta tactgtgatt tctctactgg cgaaacctgt    4080
atccgggccc aacctgaaaa catcccagcc aagaactggt ataggagctc caaggacaag    4140 aaaacacgtct ggctaggaga aactatcaat gctggcagcc agtttgaata taatgtagaa    4200
ggagtgactt ccaaggaaat ggctacccaa cttgccttca tgcgcctgct ggccaactat    4260
gcctctcaga acatcaccta ccactgcaag aacagcattg catacatgga tgaggagact    4320
ggcaacctga aaaaggctgt cattctacag ggctctaatg atgttgaact tgttgctgag    4380
ggcaacagca ggttcactta cactgttctt gtagatggct gctctaaaaa gacaaatgaa    4440
tggggaaaga caatcattga atacaaaaca aataagccat cacgcctgcc cttccttgat    4500
attgcacctt tggacatcgg tggtgctgac caggaattct ttgtggacat tggcccagtc    4560
tgtttcaaat aaatgaactc aatctaaatt aaaaaagaaa gaaatttgaa aaactttct    4620 ctttgccatt tcttcttctt ctttttaac tgaaagctga atccttccat ttcttctgca    4680
catctacttg cttaaattgt gggcaaaaga gaaaagaag gattgatcag agcattgtgc    4740
aatacagttt cattaactcc ttcccccgct cccccaaaaa tttgaatttt ttttcaaca    4800 ctcttacacc tgttatggaa aatgtcaacc tttgtaagaa aaccaaaata aaaattgaaa    4860
aataaaaacc ataaacattt gcaccacttg tggcttttga atatcttcca cagagggaag    4920
tttaaaaccc aaacttccaa aggtttaaac tacctcaaaa cactttccca tgagtgtgat    4980
ccacattgtt aggtgctgac ctagacagag atgaactgag gtccttgttt tgttttgttc    5040
ataatacaaa ggtgctaatt aatagtattt cagatacttg aagaatgttg atggtgctag    5100
aagaatttga gaagaaatac tcctgtattg agttgtatcg tgtggtgtat tttttaaaaa    5160
atttgattta gcattcatat tttccatctt attcccaatt aaaagtatgc agattatttg    5220
cccaaatctt cttcagattc agcatttgtt cttgccagt tcattttca tcttcttcca    5280 tggttccaca gaagctttgt ttcttgggca agcagaaaaa ttaaattgta cctatttgt    5340 atatgtgaga tgtttaaata aattgtgaaa aaatgaaat aaagcatgtt tggttttcca    5400
aaagaacata t                                                        5411
```

<210> SEQ ID NO 5
<211> LENGTH: 1633
<212> TYPE: DNA
<213> ORGANISM: Artificial sequence
<220> FEATURE:
<223> OTHER INFORMATION: Synthetic sequence containing the coding
regions of the vascular signal sequence of barley gene for Thiol
protease aleurain precursor fused to the human Prolyl
4-hydroxylase beta subunit and flanking regions

<400> SEQUENCE: 5

```
ctcgagtaaa ccatggctca tgctagggtt ttgcttttgg ctcttgctgt tcttgctact      60
gctgctgttg ctgtggcttc ttcttcatct ttcgctgatt ctaacccaat taggccagtg     120
actgatagag ctgcttctac tcttgctcaa ttggtcgaca tggatgctcc agaagaggag     180
gatcacgttc ttgtgcttag gaagtctaac ttcgctgaag ctcttgctgc tcacaagtac     240
cttcttgtgg agttttatgc tccttggtgc ggacattgca aagctcttgc tccagagtat     300
gctaaggctg ctggaaagtt gaaggctgag ggatctgaaa ttaggcttgc taaagtggat     360
gctactgagg agtctgatct tgctcaacag tacggagtta ggggataccc aactattaag     420
ttcttcagga acgagatac tgcttctcca aaggagtata ctgctggaag ggaggctgat     480
gatattgtga actggcttaa gaagagaact ggaccagctg ctactactct tccagatgga     540
gctgctgctg aatctcttgt ggagtcatct gaggtggcag tgattggatt cttcaaggat     600
gtggagtctg attctgctaa gcagttcctt caagctgctg aggctattga tgatattcca     660
ttcggaatta cttctaactc tgatgtgttc tctaagtacc agcttgataa ggatggagtg     720 gtgctttca agaaattcga tgagggaagg aacaatttcg agggagaggt gacaaaggag     780
aaccttcttg atttcattaa gcacaaccag cttccacttg tgattgagtt cactgagcag     840
actgctccaa agattttcgg aggagagatt aagactcaca ttcttctttt ccttccaaag     900
tctgtgtctg attacgatgg aaagttgtct aacttcaaga ctgctgctga gtctttcaag     960
ggaaagattc ttttcatttt cattgattct gatcacactg ataaccagag gattcttgag    1020
ttcttcggac ttaagaagga gagtgcccca gctgttaggc ttattactct tgaggaggag    1080
atgactaagt acaagccaga gtctgaagaa cttactgctg agaggattac tgagttctgc    1140
cacagattcc ttgagggaaa gattaagcca caccttatgt ctcaagagct tccagaggat    1200
tgggataagc agccagttaa ggtgttggtg ggtaaaaact tcgaggatgt ggctttcgat    1260
gagaagaaga acgtgttcgt ggagttctac gcaccttggt gtggtcactg taagcagctt    1320
gctccaattt gggataagtt gggagagact acaaggatc acgagaacat tgtgattgct    1380
aagatggatt ctactgctaa cgaggtggag gctgttaagg ttcactcttt cccaactttg    1440
aagttcttcc cagcttctgc tgataggact gtgattgatt acaacggaga aaggactctt    1500
gatggattca agaagttcct tgagtctgga ggacaagatg gagctggaga tgatgatgat    1560
cttgaggatt tggaagaagc tgaggagcca gatatggagg aggatgatga tcagaaggct    1620
gtgtgatgag ctc                                                       1633
```

<210> SEQ ID NO 6
<211> LENGTH: 1723
<212> TYPE: DNA
<213> ORGANISM: Artificial sequence
<220> FEATURE:
<223> OTHER INFORMATION: Synthetic sequence containing the coding
regions of the vascular signal sequence of barley gene for Thiol
protease aleurain precursor fused to the human Prolyl
4-hydroxylase alpha-1 subunit and flanking regions

<400> SEQUENCE: 6

```
ctcgagtaaa ccatggctca tgctagggtt ttgcttttgg ctcttgctgt tcttgctact        60
gctgctgttg ctgtggcttc ttcttcatct ttcgctgatt ctaacccaat taggccagtg       120
actgatagag ctgcttctac tcttgctcaa ttggtcgaca tgcacccagg attcttcact       180
tctattggac agatgactga tcttattcac actgagaagg atcttgtgac ttctcttaag       240
gattacatta aggctgagga ggataagttg gagcagatta agaagtgggc tgagaagttg       300
gataggctta cttctactgc tacaaaagat ccagagggat tcgttggtca tccagtgaac       360
gctttcaagt tgatgaagag cttaacact  gagtggagtg agcttgagaa ccttgtgctt       420
aaggatatgt ctgatggatt catttctaac cttactattc agaggcagta cttcccaaat       480
gatgaggatc aagtgggagc tgctaaggct cttcttaggc ttcaggatac ttacaacctt       540
gatactgata caatttctaa gggaaacctt ccaggagtta agcacaagtc tttccttact       600
gctgaggatt gcttcgagct tggaaaggtt gcatacactg aggctgatta ctaccacact       660
gagctttgga tggaacaagc tcttaggcaa cttgatgagg agagatttc  tactattgat       720
aaggtgtcag tgcttgatta ccttttcttac gctgtgtacc agcagggtga tcttgataag       780
gctcttttgc ttactaagaa gttgcttgag cttgatccag aacatcagag ggctaacgga       840
aaccttaagt acttcgagta cattatggct aaggaaaagg atgtgaacaa gtctgcttct       900
gatgatcagt ctgatcaaaa gactactcca agaagaagg  gagtggctgt tgattatctt       960
cctgagaggc agaagtatga gatgttgtgt aggggagagg gtattaagat gactccaagg      1020
aggcagaaga agttgttctg caggtatcac gatggaaaca ggaacccaaa gttcattctt      1080
gctccagcta gcaagaaga  tgagtgggat aagccaagga ttattaggtt ccacgatatt      1140
atttctgatg ctgagattga gattgtgaag gatcttgcta agccaagact taggagggct      1200
actatttcta acctatac   tggtgatctt gagactgtgc actacaggat ttctaagtct      1260
gcttggcttt ctggatacga gaacccagtg gtgtctagga ttaacatgag gattcaggat      1320
cttactggac ttgatgtgtc tactgctgag gagcttcaag ttgctaacta cggagttgga      1380
ggacaatatg agccacactt cgatttcgct aggaaggatg agccagatgc tttttaaggag      1440
cttggaactg gaaacaggat tgctacttgg cttttctaca tgtctgatgt ttctgctgga      1500
ggagctactg ttttcccaga agtgggagct tctgtttggc aaagaagg  aactgctgtg      1560
ttctggtaca ccttttcgc  ttctggagag ggagattact ctactaggca tgctgcttgc      1620
ccagttcttg ttggaaacaa gtgggtgtca acaagtggc  ttcatgagag gggacaagag      1680
tttagaaggc catgcactct ttctgagctt gagtgatgag ctc                        1723
```

<210> SEQ ID NO 7
<211> LENGTH: 1489
<212> TYPE: PRT
<213> ORGANISM: Artificial sequence
<220> FEATURE:
<223> OTHER INFORMATION: A recombinant protein consisting of a Vacuolar
      transit signal fused to human alpha 1(I) collagen

<400> SEQUENCE: 7

```
Met Ala His Ala Arg Val Leu Leu Leu Ala Leu Ala Val Leu Ala Thr
1               5                   10                  15

Ala Ala Val Ala Val Ala Ser Ser Ser Ser Phe Ala Asp Ser Asn Pro
            20                  25                  30

Ile Arg Pro Val Thr Asp Arg Ala Ala Ser Thr Leu Ala Gln Leu Gln
```

```
                35                  40                  45
Glu Glu Gly Gln Val Glu Gly Gln Asp Glu Asp Ile Pro Pro Ile Thr
 50                  55                  60

Cys Val Gln Asn Gly Leu Arg Tyr His Asp Arg Asp Val Trp Lys Pro
 65                  70                  75                  80

Glu Pro Cys Arg Ile Cys Val Cys Asp Asn Gly Lys Val Leu Cys Asp
                 85                  90                  95

Asp Val Ile Cys Asp Glu Thr Lys Asn Cys Pro Gly Ala Glu Val Pro
                100                 105                 110

Glu Gly Glu Cys Cys Pro Val Cys Pro Asp Gly Ser Glu Ser Pro Thr
                115                 120                 125

Asp Gln Glu Thr Thr Gly Val Glu Gly Pro Lys Gly Asp Thr Gly Pro
                130                 135                 140

Arg Gly Pro Arg Gly Pro Ala Gly Pro Pro Gly Arg Asp Gly Ile Pro
145                 150                 155                 160

Gly Gln Pro Gly Leu Pro Gly Pro Pro Gly Pro Pro Gly Pro Pro Gly
                165                 170                 175

Pro Pro Gly Leu Gly Gly Asn Phe Ala Pro Gln Leu Ser Tyr Gly Tyr
                180                 185                 190

Asp Glu Lys Ser Thr Gly Gly Ile Ser Val Pro Gly Pro Met Gly Pro
                195                 200                 205

Ser Gly Pro Arg Gly Leu Pro Gly Pro Pro Gly Ala Pro Gly Pro Gln
210                 215                 220

Gly Phe Gln Gly Pro Pro Gly Glu Pro Gly Glu Pro Gly Ala Ser Gly
225                 230                 235                 240

Pro Met Gly Pro Arg Gly Pro Pro Gly Pro Pro Gly Lys Asn Gly Asp
                245                 250                 255

Asp Gly Glu Ala Gly Lys Pro Gly Arg Pro Gly Glu Arg Gly Pro Pro
                260                 265                 270

Gly Pro Gln Gly Ala Arg Gly Leu Pro Gly Thr Ala Gly Leu Pro Gly
                275                 280                 285

Met Lys Gly His Arg Gly Phe Ser Gly Leu Asp Gly Ala Lys Gly Asp
                290                 295                 300

Ala Gly Pro Ala Gly Pro Lys Gly Glu Pro Gly Ser Pro Gly Glu Asn
305                 310                 315                 320

Gly Ala Pro Gly Gln Met Gly Pro Arg Gly Leu Pro Gly Glu Arg Gly
                325                 330                 335

Arg Pro Gly Ala Pro Gly Pro Ala Gly Ala Arg Gly Asn Asp Gly Ala
                340                 345                 350

Thr Gly Ala Ala Gly Pro Pro Gly Pro Thr Gly Pro Ala Gly Pro Pro
                355                 360                 365

Gly Phe Pro Gly Ala Val Gly Ala Lys Gly Glu Ala Gly Pro Gln Gly
                370                 375                 380

Pro Arg Gly Ser Glu Gly Pro Gln Gly Val Arg Gly Glu Pro Gly Pro
385                 390                 395                 400

Pro Gly Pro Ala Gly Ala Ala Gly Pro Ala Gly Asn Pro Gly Ala Asp
                405                 410                 415

Gly Gln Pro Gly Ala Lys Gly Ala Asn Gly Ala Pro Gly Ile Ala Gly
                420                 425                 430

Ala Pro Gly Phe Pro Gly Ala Arg Gly Pro Ser Gly Pro Gln Gly Pro
                435                 440                 445

Gly Gly Pro Pro Gly Pro Lys Gly Asn Ser Gly Glu Pro Gly Ala Pro
                450                 455                 460
```

```
Gly Ser Lys Gly Asp Thr Gly Ala Lys Gly Glu Pro Gly Pro Val Gly
465                 470                 475                 480

Val Gln Gly Pro Pro Gly Pro Ala Gly Glu Glu Gly Lys Arg Gly Ala
            485                 490                 495

Arg Gly Glu Pro Gly Pro Thr Gly Leu Pro Gly Pro Pro Gly Glu Arg
                500                 505                 510

Gly Gly Pro Gly Ser Arg Gly Phe Pro Gly Ala Asp Gly Val Ala Gly
            515                 520                 525

Pro Lys Gly Pro Ala Gly Glu Arg Gly Ser Pro Gly Pro Ala Gly Pro
        530                 535                 540

Lys Gly Ser Pro Gly Glu Ala Gly Arg Pro Gly Glu Ala Gly Leu Pro
545                 550                 555                 560

Gly Ala Lys Gly Leu Thr Gly Ser Pro Gly Ser Pro Gly Pro Asp Gly
                565                 570                 575

Lys Thr Gly Pro Pro Gly Pro Ala Gly Gln Asp Gly Arg Pro Gly Pro
            580                 585                 590

Pro Gly Pro Pro Gly Ala Arg Gly Gln Ala Gly Val Met Gly Phe Pro
        595                 600                 605

Gly Pro Lys Gly Ala Ala Gly Glu Pro Gly Lys Ala Gly Glu Arg Gly
        610                 615                 620

Val Pro Gly Pro Pro Gly Ala Val Gly Pro Ala Gly Lys Asp Gly Glu
625                 630                 635                 640

Ala Gly Ala Gln Gly Pro Pro Gly Pro Ala Gly Pro Ala Gly Glu Arg
                645                 650                 655

Gly Glu Gln Gly Pro Ala Gly Ser Pro Gly Phe Gln Gly Leu Pro Gly
                660                 665                 670

Pro Ala Gly Pro Pro Gly Glu Ala Gly Lys Pro Gly Glu Gln Gly Val
            675                 680                 685

Pro Gly Asp Leu Gly Ala Pro Gly Pro Ser Gly Ala Arg Gly Glu Arg
        690                 695                 700

Gly Phe Pro Gly Glu Arg Gly Val Gln Gly Pro Pro Gly Pro Ala Gly
705                 710                 715                 720

Pro Arg Gly Ala Asn Gly Ala Pro Gly Asn Asp Gly Ala Lys Gly Asp
                725                 730                 735

Ala Gly Ala Pro Gly Ala Pro Gly Ser Gln Gly Ala Pro Gly Leu Gln
                740                 745                 750

Gly Met Pro Gly Glu Arg Gly Ala Ala Gly Leu Pro Gly Pro Lys Gly
            755                 760                 765

Asp Arg Gly Asp Ala Gly Pro Lys Gly Ala Asp Gly Ser Pro Gly Lys
            770                 775                 780

Asp Gly Val Arg Gly Leu Thr Gly Pro Ile Gly Pro Pro Gly Pro Ala
785                 790                 795                 800

Gly Ala Pro Gly Asp Lys Gly Glu Ser Gly Pro Ser Gly Pro Ala Gly
                805                 810                 815

Pro Thr Gly Ala Arg Gly Ala Pro Gly Asp Arg Gly Glu Pro Gly Pro
            820                 825                 830

Pro Gly Pro Ala Gly Phe Ala Gly Pro Pro Gly Ala Asp Gly Gln Pro
            835                 840                 845

Gly Ala Lys Gly Glu Pro Gly Asp Ala Gly Ala Lys Gly Asp Ala Gly
            850                 855                 860

Pro Pro Gly Pro Ala Gly Pro Ala Gly Pro Pro Gly Pro Ile Gly Asn
865                 870                 875                 880
```

```
Val Gly Ala Pro Gly Ala Lys Gly Ala Arg Gly Ser Ala Gly Pro Pro
            885                 890                 895
Gly Ala Thr Gly Phe Pro Gly Ala Ala Gly Arg Val Gly Pro Pro Gly
            900                 905                 910
Pro Ser Gly Asn Ala Gly Pro Pro Gly Pro Pro Gly Pro Ala Gly Lys
            915                 920                 925
Glu Gly Gly Lys Gly Pro Arg Gly Glu Thr Gly Pro Ala Gly Arg Pro
            930                 935                 940
Gly Glu Val Gly Pro Pro Gly Pro Pro Gly Pro Ala Gly Glu Lys Gly
945                 950                 955                 960
Ser Pro Gly Ala Asp Gly Pro Ala Gly Ala Pro Gly Thr Pro Gly Pro
            965                 970                 975
Gln Gly Ile Ala Gly Gln Arg Gly Val Val Gly Leu Pro Gly Gln Arg
            980                 985                 990
Gly Arg Gly Phe Pro Gly Leu Pro Gly Pro Ser Gly Glu Pro Gly
            995                 1000                1005
Lys Gln Gly Pro Ser Gly Ala Ser Gly Glu Arg Gly Pro Pro Gly
            1010                1015                1020
Pro Met Gly Pro Pro Gly Leu Ala Gly Pro Pro Gly Glu Ser Gly
            1025                1030                1035
Arg Glu Gly Ala Pro Gly Ala Glu Gly Ser Pro Gly Arg Asp Gly
            1040                1045                1050
Ser Pro Gly Ala Lys Gly Asp Arg Gly Glu Thr Gly Pro Ala Gly
            1055                1060                1065
Pro Pro Gly Ala Pro Gly Ala Pro Gly Ala Pro Gly Pro Val Gly
            1070                1075                1080
Pro Ala Gly Lys Ser Gly Asp Arg Gly Glu Thr Gly Pro Ala Gly
            1085                1090                1095
Pro Ala Gly Pro Val Gly Pro Ala Gly Ala Arg Gly Pro Ala Gly
            1100                1105                1110
Pro Gln Gly Pro Arg Gly Asp Lys Gly Glu Thr Gly Glu Gln Gly
            1115                1120                1125
Asp Arg Gly Ile Lys Gly His Arg Gly Phe Ser Gly Leu Gln Gly
            1130                1135                1140
Pro Pro Gly Pro Pro Gly Ser Pro Gly Glu Gln Gly Pro Ser Gly
            1145                1150                1155
Ala Ser Gly Pro Ala Gly Pro Arg Gly Pro Pro Gly Ser Ala Gly
            1160                1165                1170
Ala Pro Gly Lys Asp Gly Leu Asn Gly Leu Pro Gly Pro Ile Gly
            1175                1180                1185
Pro Pro Gly Pro Arg Gly Arg Thr Gly Asp Ala Gly Pro Val Gly
            1190                1195                1200
Pro Pro Gly Pro Pro Gly Pro Pro Gly Pro Pro Gly Pro Pro Ser
            1205                1210                1215
Ala Gly Phe Asp Phe Ser Phe Leu Pro Gln Pro Pro Gln Glu Lys
            1220                1225                1230
Ala His Asp Gly Gly Arg Tyr Tyr Arg Ala Asp Ala Asn Val
            1235                1240                1245
Val Arg Asp Arg Asp Leu Glu Val Asp Thr Thr Leu Lys Ser Leu
            1250                1255                1260
Ser Gln Gln Ile Glu Asn Ile Arg Ser Pro Glu Gly Ser Arg Lys
            1265                1270                1275
Asn Pro Ala Arg Thr Cys Arg Asp Leu Lys Met Cys His Ser Asp
```

```
                  1280                1285                1290
Trp Lys Ser Gly Glu Tyr Trp Ile Asp Pro Asn Gln Gly Cys Asn
        1295                1300                1305
Leu Asp Ala Ile Lys Val Phe Cys Asn Met Glu Thr Gly Glu Thr
        1310                1315                1320
Cys Val Tyr Pro Thr Gln Pro Ser Val Ala Gln Lys Asn Trp Tyr
        1325                1330                1335
Ile Ser Lys Asn Pro Lys Asp Lys Arg His Val Trp Phe Gly Glu
        1340                1345                1350
Ser Met Thr Asp Gly Phe Gln Phe Glu Tyr Gly Gly Gln Gly Ser
        1355                1360                1365
Asp Pro Ala Asp Val Ala Ile Gln Leu Thr Phe Leu Arg Leu Met
        1370                1375                1380
Ser Thr Glu Ala Ser Gln Asn Ile Thr Tyr His Cys Lys Asn Ser
        1385                1390                1395
Val Ala Tyr Met Asp Gln Gln Thr Gly Asn Leu Lys Lys Ala Leu
        1400                1405                1410
Leu Leu Lys Gly Ser Asn Glu Ile Glu Ile Arg Ala Glu Gly Asn
        1415                1420                1425
Ser Arg Phe Thr Tyr Ser Val Thr Val Asp Gly Cys Thr Ser His
        1430                1435                1440
Thr Gly Ala Trp Gly Lys Thr Val Ile Glu Tyr Lys Thr Thr Lys
        1445                1450                1455
Thr Ser Arg Leu Pro Ile Ile Asp Val Ala Pro Leu Asp Val Gly
        1460                1465                1470
Ala Pro Asp Gln Glu Phe Gly Phe Asp Val Gly Pro Val Cys Phe
        1475                1480                1485
Leu

<210> SEQ ID NO 8
<211> LENGTH: 1389
<212> TYPE: PRT
<213> ORGANISM: Artificial sequence
<220> FEATURE:
<223> OTHER INFORMATION: A recombinant protein consisting of a Vacuolar
      transit signal fused to human alpha 2(I) collagen

<400> SEQUENCE: 8

Met Ala His Ala Arg Val Leu Leu Leu Ala Leu Ala Val Leu Ala Thr
1               5                   10                  15
Ala Ala Val Ala Val Ala Ser Ser Ser Phe Ala Asp Ser Asn Pro
                20                  25                  30
Ile Arg Pro Val Thr Asp Arg Ala Ala Ser Thr Leu Ala Gln Leu Leu
        35                  40                  45
Gln Glu Glu Thr Val Arg Lys Gly Pro Ala Gly Asp Arg Gly Pro Arg
    50                  55                  60
Gly Glu Arg Gly Pro Pro Gly Pro Pro Gly Arg Asp Gly Glu Asp Gly
65                  70                  75                  80
Pro Thr Gly Pro Pro Gly Pro Pro Gly Pro Pro Gly Pro Pro Gly Leu
                85                  90                  95
Gly Gly Asn Phe Ala Ala Gln Tyr Asp Gly Lys Gly Val Gly Leu Gly
                100                 105                 110
Pro Gly Pro Met Gly Leu Met Gly Pro Arg Gly Pro Pro Gly Ala Ala
        115                 120                 125
Gly Ala Pro Gly Pro Gln Gly Phe Gln Gly Pro Ala Gly Glu Pro Gly
```

```
              130                 135                 140
Glu Pro Gly Gln Thr Gly Pro Ala Gly Ala Arg Gly Pro Ala Gly Pro
145                 150                 155                 160

Pro Gly Lys Ala Gly Glu Asp Gly His Pro Gly Lys Pro Gly Arg Pro
                165                 170                 175

Gly Glu Arg Gly Val Val Gly Pro Gln Gly Ala Arg Gly Phe Pro Gly
            180                 185                 190

Thr Pro Gly Leu Pro Gly Phe Lys Gly Ile Arg Gly His Asn Gly Leu
        195                 200                 205

Asp Gly Leu Lys Gly Gln Pro Gly Ala Pro Gly Val Lys Gly Glu Pro
    210                 215                 220

Gly Ala Pro Gly Glu Asn Gly Thr Pro Gly Gln Thr Gly Ala Arg Gly
225                 230                 235                 240

Leu Pro Gly Glu Arg Gly Arg Val Gly Ala Pro Gly Pro Ala Gly Ala
                245                 250                 255

Arg Gly Ser Asp Gly Ser Val Gly Pro Val Gly Pro Ala Gly Pro Ile
            260                 265                 270

Gly Ser Ala Gly Pro Pro Gly Phe Pro Gly Ala Pro Gly Pro Lys Gly
        275                 280                 285

Glu Ile Gly Ala Val Gly Asn Ala Gly Pro Thr Gly Pro Ala Gly Pro
    290                 295                 300

Arg Gly Glu Val Gly Leu Pro Gly Leu Ser Gly Pro Val Gly Pro Pro
305                 310                 315                 320

Gly Asn Pro Gly Ala Asn Gly Leu Thr Gly Ala Lys Gly Ala Ala Gly
                325                 330                 335

Leu Pro Gly Val Ala Gly Ala Pro Gly Leu Pro Gly Pro Arg Gly Ile
            340                 345                 350

Pro Gly Pro Val Gly Ala Ala Gly Ala Thr Gly Ala Arg Gly Leu Val
        355                 360                 365

Gly Glu Pro Gly Pro Ala Gly Ser Lys Gly Glu Ser Gly Asn Lys Gly
    370                 375                 380

Glu Pro Gly Ser Ala Gly Pro Gln Gly Pro Pro Gly Pro Ser Gly Glu
385                 390                 395                 400

Glu Gly Lys Arg Gly Pro Asn Gly Glu Ala Gly Ser Ala Gly Pro Pro
                405                 410                 415

Gly Pro Pro Gly Leu Arg Gly Ser Pro Gly Ser Arg Gly Leu Pro Gly
            420                 425                 430

Ala Asp Gly Arg Ala Gly Val Met Gly Pro Pro Gly Ser Arg Gly Ala
        435                 440                 445

Ser Gly Pro Ala Gly Val Arg Gly Pro Asn Gly Asp Ala Gly Arg Pro
    450                 455                 460

Gly Glu Pro Gly Leu Met Gly Pro Arg Gly Leu Pro Gly Ser Pro Gly
465                 470                 475                 480

Asn Ile Gly Pro Ala Gly Lys Glu Gly Pro Val Gly Leu Pro Gly Ile
                485                 490                 495

Asp Gly Arg Pro Gly Pro Ile Gly Pro Ala Gly Ala Arg Gly Glu Pro
            500                 505                 510

Gly Asn Ile Gly Phe Pro Gly Pro Lys Gly Pro Thr Gly Asp Pro Gly
        515                 520                 525

Lys Asn Gly Asp Lys Gly His Ala Gly Leu Ala Gly Ala Arg Gly Ala
    530                 535                 540

Pro Gly Pro Asp Gly Asn Asn Gly Ala Gln Gly Pro Pro Gly Pro Gln
545                 550                 555                 560
```

```
Gly Val Gln Gly Gly Lys Glu Gln Gly Pro Ala Gly Pro Pro Gly
                565                 570                 575

Phe Gln Gly Leu Pro Gly Pro Ser Gly Pro Ala Gly Glu Val Gly Lys
                580                 585                 590

Pro Gly Glu Arg Gly Leu His Gly Glu Phe Gly Leu Pro Gly Pro Ala
                595                 600                 605

Gly Pro Arg Gly Glu Arg Gly Pro Pro Gly Glu Ser Gly Ala Ala Gly
            610                 615                 620

Pro Thr Gly Pro Ile Gly Ser Arg Gly Pro Ser Gly Pro Pro Gly Pro
625                 630                 635                 640

Asp Gly Asn Lys Gly Glu Pro Gly Val Val Gly Ala Val Gly Thr Ala
                645                 650                 655

Gly Pro Ser Gly Pro Ser Gly Leu Pro Gly Glu Arg Gly Ala Ala Gly
                660                 665                 670

Ile Pro Gly Gly Lys Gly Glu Lys Gly Glu Pro Gly Leu Arg Gly Glu
                675                 680                 685

Ile Gly Asn Pro Gly Arg Asp Gly Ala Arg Gly Ala His Gly Ala Val
                690                 695                 700

Gly Ala Pro Gly Pro Ala Gly Ala Thr Gly Asp Arg Gly Glu Ala Gly
705                 710                 715                 720

Ala Ala Gly Pro Ala Gly Pro Ala Gly Pro Arg Gly Ser Pro Gly Glu
                725                 730                 735

Arg Gly Glu Val Gly Pro Ala Gly Pro Asn Gly Phe Ala Gly Pro Ala
                740                 745                 750

Gly Ala Ala Gly Gln Pro Gly Ala Lys Gly Glu Arg Gly Ala Lys Gly
                755                 760                 765

Pro Lys Gly Glu Asn Gly Val Val Gly Pro Thr Gly Pro Val Gly Ala
770                 775                 780

Ala Gly Pro Ala Gly Pro Asn Gly Pro Pro Gly Pro Ala Gly Ser Arg
785                 790                 795                 800

Gly Asp Gly Gly Pro Pro Gly Met Thr Gly Phe Pro Gly Ala Ala Gly
                805                 810                 815

Arg Thr Gly Pro Pro Gly Pro Ser Gly Ile Ser Gly Pro Pro Gly Pro
                820                 825                 830

Pro Gly Pro Ala Gly Lys Glu Gly Leu Arg Gly Pro Arg Gly Asp Gln
                835                 840                 845

Gly Pro Val Gly Arg Thr Gly Glu Val Gly Ala Val Gly Pro Pro Gly
            850                 855                 860

Phe Ala Gly Glu Lys Gly Pro Ser Gly Glu Ala Gly Thr Ala Gly Pro
865                 870                 875                 880

Pro Gly Thr Pro Gly Pro Gln Gly Leu Leu Gly Ala Pro Gly Ile Leu
                885                 890                 895

Gly Leu Pro Gly Ser Arg Gly Glu Arg Gly Leu Pro Gly Val Ala Gly
                900                 905                 910

Ala Val Gly Glu Pro Gly Pro Leu Gly Ile Ala Gly Pro Pro Gly Ala
                915                 920                 925

Arg Gly Pro Pro Gly Ala Val Gly Ser Pro Gly Val Asn Gly Ala Pro
                930                 935                 940

Gly Glu Ala Gly Arg Asp Gly Asn Pro Gly Asn Asp Gly Pro Pro Gly
945                 950                 955                 960

Arg Asp Gly Gln Pro Gly His Lys Gly Glu Arg Gly Tyr Pro Gly Asn
                965                 970                 975
```

```
Ile Gly Pro Val Gly Ala Ala Gly Ala Pro Gly Pro His Gly Pro Val
            980                 985                 990

Gly Pro Ala Gly Lys His Gly Asn Arg Gly Glu Thr Gly Pro Ser Gly
        995                 1000                1005

Pro Val Gly Pro Ala Gly Ala Val Gly Pro Arg Gly Pro Ser Gly
        1010                1015                1020

Pro Gln Gly Ile Arg Gly Asp Lys Gly Glu Pro Gly Glu Lys Gly
        1025                1030                1035

Pro Arg Gly Leu Pro Gly Phe Lys Gly His Asn Gly Leu Gln Gly
        1040                1045                1050

Leu Pro Gly Ile Ala Gly His His Gly Asp Gln Gly Ala Pro Gly
        1055                1060                1065

Ser Val Gly Pro Ala Gly Pro Arg Gly Pro Ala Gly Pro Ser Gly
        1070                1075                1080

Pro Ala Gly Lys Asp Gly Arg Thr Gly His Pro Gly Thr Val Gly
        1085                1090                1095

Pro Ala Gly Ile Arg Gly Pro Gln Gly His Gln Gly Pro Ala Gly
        1100                1105                1110

Pro Pro Gly Pro Pro Gly Pro Pro Gly Pro Pro Gly Val Ser Gly
        1115                1120                1125

Gly Gly Tyr Asp Phe Gly Tyr Asp Gly Asp Phe Tyr Arg Ala Asp
        1130                1135                1140

Gln Pro Arg Ser Ala Pro Ser Leu Arg Pro Lys Asp Tyr Glu Val
        1145                1150                1155

Asp Ala Thr Leu Lys Ser Leu Asn Asn Gln Ile Glu Thr Leu Leu
        1160                1165                1170

Thr Pro Glu Gly Ser Arg Lys Asn Pro Ala Arg Thr Cys Arg Asp
        1175                1180                1185

Leu Arg Leu Ser His Pro Glu Trp Ser Ser Gly Tyr Tyr Trp Ile
        1190                1195                1200

Asp Pro Asn Gln Gly Cys Thr Met Glu Ala Ile Lys Val Tyr Cys
        1205                1210                1215

Asp Phe Pro Thr Gly Glu Thr Cys Ile Arg Ala Gln Pro Glu Asn
        1220                1225                1230

Ile Pro Ala Lys Asn Trp Tyr Arg Ser Ser Lys Asp Lys Lys His
        1235                1240                1245

Val Trp Leu Gly Glu Thr Ile Asn Ala Gly Ser Gln Phe Glu Tyr
        1250                1255                1260

Asn Val Glu Gly Val Thr Ser Lys Glu Met Ala Thr Gln Leu Ala
        1265                1270                1275

Phe Met Arg Leu Leu Ala Asn Tyr Ala Ser Gln Asn Ile Thr Tyr
        1280                1285                1290

His Cys Lys Asn Ser Ile Ala Tyr Met Asp Glu Glu Thr Gly Asn
        1295                1300                1305

Leu Lys Lys Ala Val Ile Leu Gln Gly Ser Asn Asp Val Glu Leu
        1310                1315                1320

Val Ala Glu Gly Asn Ser Arg Phe Thr Tyr Thr Val Leu Val Asp
        1325                1330                1335

Gly Cys Ser Lys Lys Thr Asn Glu Trp Gly Lys Thr Ile Ile Glu
        1340                1345                1350

Tyr Lys Thr Asn Lys Pro Ser Arg Leu Pro Phe Leu Asp Ile Ala
        1355                1360                1365

Pro Leu Asp Ile Gly Gly Ala Asp His Glu Phe Phe Val Asp Ile
```

```
              1370           1375           1380
Gly Pro  Val Cys Phe Lys
    1385

<210> SEQ ID NO 9
<211> LENGTH: 2888
<212> TYPE: DNA
<213> ORGANISM: Artificial sequence
<220> FEATURE:
<223> OTHER INFORMATION: Synthetic sequence containing the coding
      regions of the vascular signal sequence of barley gene for Thiol
      protease aleurain precursor fused to the human Lysyl hydroxylase 3
      and flanking regions

<400> SEQUENCE: 9
gcgaattcgc tagctatcac tgaaaagaca gcaagacaat ggtgtctcga tgcaccagaa      60
ccacatcttt gcagcagatg tgaagcagcc agagtggtcc acaagacgca ctcagaaaag     120
gcatcttcta ccgacacaga aaagacaaac cacagctcat catccaacat gtagactgtc     180
gttatgcgtc ggctgaagat aagactgacc ccaggccagc actaaagaag aaataatgca     240
agtggtccta gctccacttt agctttaata attatgtttc attattattc tctgcttttg     300
ctctctatat aaagagcttg tattttcatt tgaaggcaga ggcgaacaca cacacagaac     360
ctccctgctt acaaaccaga tcttaaacca tggctcacgc tagggttttg cttcttgctc     420
ttgctgttct tgctactgct gctgttgctg tggcttcttc aagttctttc gctgattcta     480
acccaattag gccagtgact gatagagctg cttctactct tgctcaattg agatctatgt     540
ctgatagacc aaggggaagg gatccagtta atccagagaa gttgcttgtg attactgtgg     600
ctactgctga gactgaagga taccttagat ccttaggag tgctgagttc ttcaactaca     660
ctgtgaggac tcttggactt ggagaagaat ggaggggagg agatgttgct agaactgttg     720
gaggaggaca gaaagtgaga tggcttaaga agagatggaa gagtacgct gatagggagg     780 atatgattat tatgttcgtg gattcttacg atgtgattct tgctggatct ccaactgagc     840 tttttgaagaa attcgttcag tctggatcta ggcttctttt ctctgctgag tcttttgtt      900 ggccagaatg gggacttgct gagcaatatc agaagtggg aactggaaag agattcctta      960
actctggagg attcattgga ttcgctacta ctattcacca gattgtgagg cagtggaagt     1020
acaaggatga cgatgatgat cagcttttct cactaggct ttaccttgat ccaggactta     1080
gggagaagtt gtctcttaac cttgatcaca agtctaggat tttccagaac cttaacggtg     1140
ctcttgatga ggttgtgctt aagttcgata ggaacagagt gaggattagg aacgtggctt     1200
acgatactct tcctattgtg gtgcatggaa acggaccaac aaaactccag cttaactacc     1260
ttggaaacta cgttccaaac ggatggactc cagaaggagg atgtggattc tgcaatcagg     1320
ataggagaac tcttccagga ggacaaccac accaagagt tttccttgct gtgttcgttg     1380
aacagccaac tccattcctt ccaagattcc ttcagaggct tcttcttttg gattacccac     1440
cagatagggt gacactttt cttcacaaca acgaggtttt ccacgagcca cacattgctg     1500
attcttggcc acagcttcag gatcatttct ctgctgtgaa gttggttggt ccagaagaag     1560
ctctttctcc aggagaagct agggatatgc tatggatttt gtgcaggcag gatccagagt     1620
gcgagttcta cttctctctt gatgctgatg ctgtgcttac taaccttcag actcttagga     1680
ttcttattga ggggaacagg aaagtgattg ctccaatgct ttctaggcac ggaaagttgt     1740
ggtctaattt ctggggtgct ctttctcctg atgagtacta cgctagatca gaggactacg     1800
tggagcttgt tcagagaaag agagtgggag tttggaacgt tccttatatt tctcaggctt     1860
```

-continued

```
acgtgattag gggagatact cttaggatgg agcttccaca gagggatgtt ttctctggat    1920
ctgatactga tccagatatg gctttctgca agtctttcag ggataaggga atttccttc    1980 accttctaa ccagcatgag ttcggaagat tgcttgctac ttcaagatac gatactgagc    2040
accttcatcc tgatctttgg cagattttcg ataacccagt ggattggaag gagcagtaca    2100
ttcacgagaa ctactctagg gctcttgaag gagaaggaat tgtggagcaa ccatgcccag    2160
atgtttactg gttcccactt cttctgagc aaatgtgcga tgagcttgtt gctgagatgg     2220
agcattacgg acaatggagt ggaggtagac atgaggattc taggcttgct ggaggatacg    2280
agaacgttcc aactgtggat attcacatga agcaagtggg atacgaggat caatggcttc    2340
agcttcttag gacttatgtg ggaccaatga ctgagtctct tttcccagga taccacacta    2400
aggctagggc tgttatgaac ttcgttgtga ggtatcgtcc agatgagcaa ccatctctta    2460
ggccacacca cgattcttct actttcactc ttaacgtggc tcttaaccac aagggacttg    2520
attatgaggg aggaggatgc cgtttcctta gatacgattg cgtgatttct tcaccaagaa    2580
agggatgggc tcttcttcat ccaggaaggc ttactcatta ccacgaggga cttccaacta    2640
cttggggaac tagatatatt atggtgtctt tcgtggatcc atgactgctt taatgagata    2700
tgcgagacgc ctatgatcgc atgatatttg ctttcaattc tgttgtgcac gttgtaaaaa    2760
acctgagcat gtgtagctca gatccttacc gccggtttcg gttcattcta atgaatatat    2820
cacccgttac tatcgtattt ttatgaataa tattctccgt tcaatttact gattgtccag    2880
aattcgcg                                                             2888
```

<210> SEQ ID NO 10
<211> LENGTH: 57
<212> TYPE: PRT
<213> ORGANISM: Pisum sativum
<220> FEATURE:
<221> NAME/KEY: misc_feature
<223> OTHER INFORMATION: RuBisCO small subunit 3A chloroplast targeting
      signal peptide

<400> SEQUENCE: 10

Met Ala Ser Met Ile Ser Ser Ser Ala Val Thr Thr Val Ser Arg Ala
1               5                   10                  15

Ser Thr Val Gln Ser Ala Ala Val Ala Pro Phe Gly Gly Leu Lys Ser
            20                  25                  30

Met Thr Gly Phe Pro Val Lys Lys Val Asn Thr Asp Ile Thr Ser Ile
        35                  40                  45

Thr Ser Asn Gly Gly Arg Val Lys Cys
    50                  55

<210> SEQ ID NO 11
<211> LENGTH: 28
<212> TYPE: PRT
<213> ORGANISM: Arabidopsis thaliana
<220> FEATURE:
<221> NAME/KEY: misc_feature
<223> OTHER INFORMATION: Transaminase A mitochondria targeting signal
      peptide

<400> SEQUENCE: 11

Met Ala Leu Ala Met Met Ile Arg Asn Ala Ala Ser Lys Arg Gly Met
1               5                   10                  15

Thr Pro Ile Ser Gly His Phe Gly Gly Leu Arg Ser
            20                  25

<210> SEQ ID NO 12
<211> LENGTH: 4467
<212> TYPE: DNA
<213> ORGANISM: Artificial sequence
<220> FEATURE:
<223> OTHER INFORMATION: Synthetic sequence containing the coding
regions of the vascular signal sequence of barley gene for Thiol
protease aleurain precursor fused to the Human alpha 1 collagen

<400> SEQUENCE: 12

```
atggctcacg ctcgtgttct cctcctcgct ctcgctgttt tggcaacagc tgctgtggct       60
gtggcttcta gttcttcttt tgctgattca aaccctatta gacctgttac tgatagagca      120
gcttccactt tggctcaatt gcaagaggag ggccaggttg agggccaaga tgaggatatc      180
cctccaatta catgcgtgca aaatggcttg cgttaccacg ataggatgt gtggaaacct       240
gaaccttgtc gtatctgtgt gtgtgataac ggcaaggtgc tctgcgatga tgttatctgc      300
gatgagacaa aaaattgccc tggcgctgaa gttcctgagg gcgagtgttg ccctgtgtgc      360
cctgatggtt ccgagtcccc aactgatcag gaaactactg gcgtggaggg cccaaaagga      420
gatactggtc cacgtggtcc tagggtcca gcaggtcctc caggtagaga tggtattcca       480
ggccagcctg gattgccagg accaccaggc ccacctggcc caccaggacc tcctggtctt      540
ggtggaaatt tcgctccaca actctcttat ggctatgatg agaagtcaac aggtggtatt      600
tccgttccag gtcctatggg accatccgga ccaagaggtc tcccaggtcc tccaggtgct      660
cctggacctc aaggctttca aggacctcca ggcgaaccag agaaccaggc gcttctgga       720
ccaatgggcc caaggggacc acctggccca ccaggaaaaa atggcgatga tggcgaagct      780
ggaaagcctg gtcgtcctgg agagagaggt cctcctggcc cacagggtgc aagaggcttg      840
ccaggaactc tggcttgcc tggaatgaag gacatagggg gcttctccgg cctcgatggc       900
gctaagggtg atgctggccc tgctggacca aagggcgagc aggttcccc tggagaaaac      960
ggtgctcctg gacaaatggg tcctcgtgga cttccaggag aaaggggtcg tccaggcgct     1020
ccaggaccag caggtgctag gggaaacgat ggtgcaacag gcgctgctgg ccctcctggc     1080
ccaactggtc ctgctggccc tccaggattc ccaggcgcga ttggagctaa ggagaagca      1140
ggaccacagg gccctagggg ttctgaagga cctcagggtg ttagaggtga accaggtcct     1200
ccaggcccag ctggagcagc tggtccagca ggaaatccag gtgctgatgg tcaacctgga     1260
gctaagggcg ctaatggcgc accaggtatc gcaggcgcac caggtttccc tggcgctaga     1320
ggcccaagtg gtcctcaagg accaggtgga ccaccaggtc aaaaggcaa ttctggcgaa      1380
cctggcgctc aggttctaa aggagatact ggtgctaaag gcgaaccagg acctgttggt     1440
gttcagggtc ctcctggtcc tgctggagaa gaggaaaaa gaggtgctcg tgagaacca      1500
ggaccaactg gacttcctgg acctcctggt gaacgtggcg gacctggctc aagggggttc     1560
cctggagctg atggagtggc aggtccaaaa ggccctgctg agagagagg ttcaccaggt      1620
ccagctggtc ctaagggctc ccctggtgaa gcaggtagac aggcgaagc aggattgcca     1680
ggcgcaaagg gattgacagg ctctcctggt agtcctggcc cagatggaaa acaggcccca     1740
ccaggtccag caggacaaga tggacgtcca ggccccaccag gtcctcctgg agcaagggga     1800
caagctggcg ttatgggttt tccaggacct aaaggtgctg ctggagagcc aggaaaggca     1860
ggtgaaagag gagttcctgg tccaccagga gcagtgggtc ctgctggcaa agatggtgaa     1920
gctggagcac agggccctcc aggccctgct ggccagctg gcgaacgtgg agaacaaggc     1980
ccagctggta gtccaggatt tcaaggattg cctggccctg ctggccctcc aggagaagca     2040
```

```
ggaaaacctg gagaacaagg agttcctggt gatttgggag cacctggacc ttcaggagca   2100
cgtggtgaaa gaggcttccc tggcgagagg ggtgttcaag gtccaccagg tccagcagga   2160
cctagaggtg ctaatggcgc tcctggcaac gatggagcaa aaggtgatgc tggtgctcct   2220
ggcgcacctg gaagtcaggg tgctcctgga ttgcaaggaa tgcctggaga gaggggtgct   2280
gctggcttgc caggcccaaa gggcgatagg ggtgatgctg gaccaaaagg tgctgatgga   2340
tccccaggaa aagatggagt tcgtggtctt actggcccaa tcggacctcc aggccctgct   2400
ggcgctccag gtgataaggg cgaaagtggc ccaagtggac ctgctggacc tactggtgct   2460
agaggtgcac ctggtgatag gggtgaacct ggaccacctg gtccagctgg ttttgctggt   2520
cctcctggag ctgatggaca acctggcgca aaggtgaac caggtgatgc tggcgcaaag    2580
ggagatgctg gtccacctgg acctgctggt ccagcaggcc ccctgggcc aatcggtaat    2640
gttggagcac aggtgctaa gggagctagg ggttccgctg gtccacctgg agcaacagga    2700
tttccaggcg ctgctggtag agttggccca ccaggcccat ccggaaacgc aggccctcct   2760
ggtcctccag gtcctgctgg caaggagggt ggcaaaggac caaggggcga aactggccct   2820
gctggtagac ctggcgaagt tggccctcct ggaccaccag gtccagcagg agaaaaaggt   2880
tccccaggag ctgatggccc agctggtgct ccaggaactc caggccctca aggtattgct   2940
ggacagagag gcgttgtggg actccctggt caaaggggag agagaggatt tccaggcttg   3000
ccaggaccta gtggagaacc tggaaaacaa ggcccatcag gcgctagtgg agagcgtgga   3060
cctcctggcc ctatgggacc tcctggattg gctggcccac ctggcgaatc aggtcgtgaa   3120
ggcgcaccag gcgcagaagg atcacctgga agagatggat cccctggtgc taaaggcgat   3180
cgtggagaaa ctggtccagc aggcccacca ggcgcaccag gtgcacctgg cgctccagga   3240
cctgtgggac cagctggaaa atccggagat aggggcgaga caggcccagc aggaccagct   3300
ggacctgttg ccctgctggg cgctcgtgga ccagcaggac ctcaaggacc aaggggagat   3360
aagggagaaa caggcgaaca aggcgatagg ggcattaagg gtcataggg ttttagtggc    3420
ctccagggtc ctcctggccc acctggatca ccaggagaac agggaccatc tggtgcttcc   3480
ggcccagctg gtccaagagg acctccagga tcagctggtg cacctggaaa agatggtctt   3540
aacggtctcc caggaccaat cggccctcca ggacctagag gaagaacagg agatgctggc   3600
cctgttggcc ctcaggacc tcctggtcca ccaggtccac ctggtcctcc atcagctgga    3660
ttcgattttt catttcttcc acagccacca aagagaaag ctcacgatgg cggcagatat    3720
taccgtgctg atgatgctaa cgttgttagg gatagagatt tggaagtgga tacaactttg   3780
aaatccctct cccagcaaat tgaaaacatt agatctccag aaggttcacg taaaaaccca   3840
gctagaacat gtcgtgattt gaaaatgtgt cactccgatt ggaaaagtgg taatactgg    3900
attgatccaa tcagggctg taatctcgat gctatcaaag ttttctgtaa catggaaaca   3960
ggcgaaacat cgtttatcc tactcaacct tccgtggctc agaaaaattg gtacatctca    4020
aaaaatccta agataagag gcacgtttgg ttcggtgaaa gtatgactga tggatttcaa   4080
tttgagtacg gcggtcaagg tagtgatcca gctgatgtgg ctattcaact cacattttg    4140
cgtcttatgt ccacagaggc atcacaaaac atcacttacc actgcaaaaa cagtgtggct   4200
tatatggatc aacaaacagg aaaccttaag aaggctcttc ttttgaaggg ctcaaacgag   4260
attgagatta gagcagaggg caactcaagg tttacttatt cagttactgt tgatggctgc   4320
acttcacata ctggcgcttg gggtaaaaca gttatcgagt ataagactac aaaaacatca   4380
```

```
agactcccaa tcattgatgt tgctcctctc gatgttggcg ctcctgatca agagttcggt   4440
tttgatgtgg gcccagtttg tttcctc                                      4467

<210> SEQ ID NO 13
<211> LENGTH: 3627
<212> TYPE: DNA
<213> ORGANISM: Artificial sequence
<220> FEATURE:
<223> OTHER INFORMATION: Synthetic sequence containing the coding
      regions of the vascular signal sequence of barley gene for Thiol
      protease aleurain precursor fused to the Human alpha 2 collagen

<400> SEQUENCE: 13
atggctcacg ctcgtgttct cctcctcgct ctcgctgttt tggcaacagc tgctgtggct     60
gtggcttcaa gttctagttt tgctgattcc aacccaattc gtccagttac tgatagagca    120
gcttccactt tggctcaatt gcttcaagaa gaaactgtga ggaagggccc tgctggcgat    180
aggggcccta ggggcgaaag gggtccacca ggacctccag gcagggatgg cgaagatggt    240
ccaactggcc ctcctggacc tcctggccct ccagggccac ccggcttggg cggaaacttc    300
gcagctcaat acgatggcaa gggtgttggt cttggtcctg gtcctatggg cttgatggga    360
cctagaggcc cacctggtgc tgctggtgct cctggaccag aggttttca gggaccagct    420 ggcgagccag gagagccagg ccaaacagga ccagctggtg caaggggacc tgctggacct    480
cctgaaaaag ctggtgaaga tggtcaccca ggcaaaccag acgtcctgg cgaaagaggt    540 gttgttggac acaaggcgc taggggattt ccaggtacac tggattgcc aggttttaag    600 ggcattcgtg gtcataacgg cctcgatgga ttgaagggac agcctggcgc acctggcgtt    660
aagggtgaac ctggagcacc aggtgaaaac ggtactcctg gccagactgg tgcaagagga    720
ctcccaggtg aaaggggtag agttggtgct cctggacctg ctggagctag ggtagtgat    780 ggtagtgttg gtcctgtggg ccctgctggt ccaatcggtt ccgctggccc acctggattc    840
ccaggcgctc caggacctaa aggagaaatc ggtgctgtgg gtaacgcagg tcctactggt    900
ccagcaggtc ctcgtggaga agtgggattg ccaggacttt ctggtccagt gggccctcca    960
ggcaaccctg gagctaacgg cttgacagga gctaaaggcg cagcaggact ccctggagtg   1020
gctggcgcac caggattgcc tggtccaagg ggtatcccag ccctgttgg cgcagctgga   1080 gctactggtg cacgtggact tgttggcgaa ccaggccctg ctggatcaaa aggcgagtct   1140
ggaaataagg gagaacctgg ttctgctgga cctcaaggtc ctcctggacc ttctggagaa   1200
gaaggaaaaa ggggaccaaa tggcgaggct ggatcagcag gtccaccagg accacctgga   1260
cttcgtggat cccctggtag tagaggactt ccaggcgctg atggtagagc aggcgttatg   1320
ggaccaccag gaagtagagg agcatccggt ccagcaggag ttaggggtcc taacggagat   1380
gctggtagac aggtgaacc aggtcttatg ggcccaaggg gcctcccagg tagtccagga   1440
aatatcggcc ctgctggaaa agaaggccct gttggacttc aggtattga tggacgtcct   1500 ggccctattg gcccagcagg tgcaagagga gaacctggca atattggatt tccaggacca   1560
aagggtccaa caggcgatcc tggaaaaaat ggagataagg gtcatgctgg attggcaggc   1620
gcaaggggcg ctcctggtcc agatggaaac aacggcgcac agggtccacc tggccctcag   1680
ggtgttcaag gcggaaaagg cgaacaaggc ccagctggac accaggcttt caaggcttg   1740 ccaggaccaa gtggtccagc aggtgaagtt ggcaagccag gcgagcgtgg acttcatggc   1800
gagtttggac tccctggacc agcaggacca agggtgaaa gaggcccctcc tggagagagt   1860 ggcgctgctg gaccaacagg cccaatcggt agtagaggtc ctagtggacc tccaggccca   1920
```

```
gatggaaata agggtgaacc aggagttgtg ggcgctgttg gaacagctgg tccttcagga      1980
ccatcaggac tcccaggcga gagaggcgct gctggcattc ctggaggaaa aggtgaaaaa      2040
ggcgaacctg gcctccgtgg cgaaatcgga atcctggacg tgatggtgc tcgtggtgca      2100 cacggcgctg tgggcgctcc aggccctgct ggtgctactg gtgatagagg agaggctggc      2160
gcagctggcc cagcaggtcc tgctggccca aggggtagtc ctggtgaaag aggcgaagtt      2220
ggacctgctg gccctaacgg ctttgctggc cctgctggag cagcaggtca acctggcgct      2280
aaaggtgaaa ggggcggaaa gggcccaaaa ggtgaaaatg gcgttgtggg accaactggt      2340
ccagtgggcg cagctggacc tgctggtcca aatggaccac caggaccagc aggtagtaga      2400
ggagatggtg gacctccagg aatgacaggt tttccaggtg ctgctggtag aacaggacct      2460
cctggtccta gtggtatttc tggtccacca ggaccaccag tcctgctgg aaaagaagga      2520 ttgaggggtc cacgtggtga tcaaggacca gtgggcagaa ctggtgaagt tggcgcagtg      2580
ggaccacctg gttttgctgg agaaaagggc ccttctggag aggcaggaac agctggtcct      2640
cctggtacac ctggacctca aggactttg gtgcacctg gtattctcgg attgccagga      2700
agtaggggcg aacgtggact tcctggcgtg gcaggagcag ttggagaacc tggccctctc      2760
ggaatcgcag gcccaccagg cgcaagagga ccaccaggag ctgttggatc accaggcgtg      2820
aatggtgcac ctggcgaggc tggtcgtgat ggaaacccag gaatgatgg cccaccagga      2880 agagatggtc aacctggaca caaggcgag aggggctacc aggaaatat tggcccagtt      2940 ggtgctgctg gcgcaccagg cccacacggt ccagttggac cagcaggaaa acacggtaat      3000
cgtggcgaaa caggccctc aggcccagtg ggacctgctg gtgctgttgg cccaagagga      3060
ccatctggac tcaaggcat tagaggcgat aagggagagc ctggcgaaaa aggacctaga      3120
ggcttgcctg gttttaaagg acacaacggt ctccaaggac ttccaggtat cgctggtcat      3180 catgagagatc agggtgctcc tggatcagtg ggtccagcag tcctagagg cccagcaggc      3240 ttcgagtata atgttgaggg cgttacttct aaagagatgg caactcagct cgcttttatg      3300
agattgctcg ctaactacgc atcccaaaac atcacttatc actgcaaaaa ttccattgca      3360
tatatggatg aggagacagg aaatttgaag aaagcagtta ttctccaagg tagtaacgat      3420
gttgagcttg tggctgaggg aaatagtaga ttcacttaca cagttttggt ggatggatgc      3480
tcaaagaaaa ctaatgagtg gggcaagaca atcattgagt acaagacaaa taagccttct      3540
aggctcccat ttctcgatat tgcacctctt gatatcggag gagctgatca cgagtttttt      3600
gttgatatcg gacctgtttg ttttaag                                            3627
```

<210> SEQ ID NO 14
<211> LENGTH: 45
<212> TYPE: PRT
<213> ORGANISM: Artificial sequence
<220> FEATURE:
<223> OTHER INFORMATION: Vacuolar transit signal originating from a
      plant vacuolar thiol protease

<400> SEQUENCE: 14

Met Ala His Ala Arg Val Leu Leu Leu Ala Leu Ala Val Leu Ala Thr
1               5                   10                  15

Ala Ala Val Ala Val Ala Ser Ser Ser Phe Ala Asp Ser Asn Pro
            20                  25                  30

Ile Arg Pro Val Thr Asp Arg Ala Ala Ser Thr Leu Ala
        35                  40                  45

-continued

```
<210> SEQ ID NO 15
<211> LENGTH: 1464
<212> TYPE: PRT
<213> ORGANISM: Homo sapiens
<220> FEATURE:
<221> NAME/KEY: MISC_FEATURE
<223> OTHER INFORMATION: Alpha-1 type I collagen

<400> SEQUENCE: 15

Met Phe Ser Phe Val Asp Leu Arg Leu Leu Leu Leu Ala Ala Thr
1               5                   10                  15

Ala Leu Leu Thr His Gly Gln Glu Glu Gly Gln Val Glu Gly Gln Asp
                20                  25                  30

Glu Asp Ile Pro Pro Ile Thr Cys Val Gln Asn Gly Leu Arg Tyr His
                35                  40                  45

Asp Arg Asp Val Trp Lys Pro Glu Pro Cys Arg Ile Cys Val Cys Asp
        50                  55                  60

Asn Gly Lys Val Leu Cys Asp Asp Val Ile Cys Asp Glu Thr Lys Asn
65                  70                  75                  80

Cys Pro Gly Ala Glu Val Pro Glu Gly Glu Cys Cys Pro Val Cys Pro
                85                  90                  95

Asp Gly Ser Glu Ser Pro Thr Asp Gln Glu Thr Thr Gly Val Glu Gly
                100                 105                 110

Pro Lys Gly Asp Thr Gly Pro Arg Gly Pro Arg Gly Pro Ala Gly Pro
                115                 120                 125

Pro Gly Arg Asp Gly Ile Pro Gly Gln Pro Gly Leu Pro Gly Pro Pro
        130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Ile Ser
                165                 170                 175

Val Pro Gly Pro Met Gly Pro Ser Gly Pro Arg Gly Leu Pro Gly Pro
                180                 185                 190

Pro Gly Ala Pro Gly Pro Gln Gly Phe Gln Gly Pro Pro Gly Glu Pro
                195                 200                 205

Gly Glu Pro Gly Ala Ser Gly Pro Met Gly Pro Arg Gly Pro Pro Gly
        210                 215                 220

Pro Pro Gly Lys Asn Gly Asp Asp Gly Glu Ala Gly Lys Pro Gly Arg
225                 230                 235                 240

Pro Gly Glu Arg Gly Pro Pro Gly Pro Gln Gly Ala Arg Gly Leu Pro
                245                 250                 255

Gly Thr Ala Gly Leu Pro Gly Met Lys Gly His Arg Gly Phe Ser Gly
                260                 265                 270

Leu Asp Gly Ala Lys Gly Asp Ala Gly Pro Ala Gly Pro Lys Gly Glu
        275                 280                 285

Pro Gly Ser Pro Gly Glu Asn Gly Ala Pro Gly Gln Met Gly Pro Arg
                290                 295                 300

Gly Leu Pro Gly Glu Arg Gly Arg Pro Gly Ala Pro Gly Pro Ala Gly
305                 310                 315                 320

Ala Arg Gly Asn Asp Gly Ala Thr Gly Ala Ala Gly Pro Pro Gly Pro
                325                 330                 335

Thr Gly Pro Ala Gly Pro Pro Gly Phe Pro Gly Ala Val Gly Ala Lys
                340                 345                 350

Gly Glu Ala Gly Pro Gln Gly Pro Arg Gly Ser Glu Gly Pro Gln Gly
        355                 360                 365
```

-continued

Val Arg Gly Glu Pro Gly Pro Gly Pro Ala Gly Ala Ala Gly Pro
    370             375             380

Ala Gly Asn Pro Gly Ala Asp Gly Gln Pro Gly Ala Lys Gly Ala Asn
385             390             395             400

Gly Ala Pro Gly Ile Ala Gly Ala Pro Gly Phe Pro Gly Ala Arg Gly
            405             410             415

Pro Ser Gly Pro Gln Gly Pro Gly Gly Pro Gly Pro Lys Gly Asn
        420             425             430

Ser Gly Glu Pro Gly Ala Pro Gly Ser Lys Gly Asp Thr Gly Ala Lys
        435             440             445

Gly Glu Pro Gly Pro Val Gly Val Gln Gly Pro Pro Gly Pro Ala Gly
    450             455             460

Glu Glu Gly Lys Arg Gly Ala Arg Gly Glu Pro Gly Pro Thr Gly Leu
465             470             475             480

Pro Gly Pro Pro Gly Glu Arg Gly Gly Pro Gly Ser Arg Gly Phe Pro
            485             490             495

Gly Ala Asp Gly Val Ala Gly Pro Lys Gly Pro Ala Gly Glu Arg Gly
            500             505             510

Ser Pro Gly Pro Ala Gly Pro Lys Gly Ser Pro Gly Glu Ala Gly Arg
        515             520             525

Pro Gly Glu Ala Gly Leu Pro Gly Ala Lys Gly Leu Thr Gly Ser Pro
    530             535             540

Gly Ser Pro Gly Pro Asp Gly Lys Thr Gly Pro Pro Gly Pro Ala Gly
545             550             555             560

Gln Asp Gly Arg Pro Gly Pro Pro Gly Pro Pro Gly Ala Arg Gly Gln
            565             570             575

Ala Gly Val Met Gly Phe Pro Gly Pro Lys Gly Ala Ala Gly Glu Pro
            580             585             590

Gly Lys Ala Gly Glu Arg Gly Val Pro Gly Pro Pro Gly Ala Val Gly
        595             600             605

Pro Ala Gly Lys Asp Gly Glu Ala Gly Ala Gln Gly Pro Pro Gly Pro
    610             615             620

Ala Gly Pro Ala Gly Glu Arg Gly Glu Gln Gly Pro Ala Gly Ser Pro
625             630             635             640

Gly Phe Gln Gly Leu Pro Gly Pro Ala Gly Pro Pro Gly Glu Ala Gly
            645             650             655

Lys Pro Gly Glu Gln Gly Val Pro Gly Asp Leu Gly Ala Pro Gly Pro
            660             665             670

Ser Gly Ala Arg Gly Glu Arg Gly Phe Pro Gly Glu Arg Gly Val Gln
        675             680             685

Gly Pro Pro Gly Pro Ala Gly Pro Arg Gly Ala Asn Gly Ala Pro Gly
    690             695             700

Asn Asp Gly Ala Lys Gly Asp Ala Gly Ala Pro Gly Ala Pro Gly Ser
705             710             715             720

Gln Gly Ala Pro Gly Leu Gln Gly Met Pro Gly Glu Arg Gly Ala Ala
            725             730             735

Gly Leu Pro Gly Pro Lys Gly Asp Arg Gly Asp Ala Gly Pro Lys Gly
            740             745             750

Ala Asp Gly Ser Pro Gly Lys Asp Gly Val Arg Gly Leu Thr Gly Pro
        755             760             765

Ile Gly Pro Pro Gly Pro Ala Gly Ala Pro Gly Asp Lys Gly Glu Ser
    770             775             780

```
Gly Pro Ser Gly Pro Ala Gly Pro Thr Gly Ala Arg Gly Ala Pro Gly
785                 790                 795                 800

Asp Arg Gly Glu Pro Gly Pro Pro Gly Pro Ala Gly Phe Ala Gly Pro
                805                 810                 815

Pro Gly Ala Asp Gly Gln Pro Gly Ala Lys Gly Glu Pro Gly Asp Ala
            820                 825                 830

Gly Ala Lys Gly Asp Ala Gly Pro Pro Gly Pro Ala Gly Pro Ala Gly
        835                 840                 845

Pro Pro Gly Pro Ile Gly Asn Val Gly Ala Pro Gly Ala Lys Gly Ala
850                 855                 860

Arg Gly Ser Ala Gly Pro Pro Gly Ala Thr Gly Phe Pro Gly Ala Ala
865                 870                 875                 880

Gly Arg Val Gly Pro Pro Gly Pro Ser Gly Asn Ala Gly Pro Pro Gly
                885                 890                 895

Pro Pro Gly Pro Ala Gly Lys Glu Gly Gly Lys Gly Pro Arg Gly Glu
                900                 905                 910

Thr Gly Pro Ala Gly Arg Pro Gly Glu Val Gly Pro Pro Gly Pro Pro
            915                 920                 925

Gly Pro Ala Gly Glu Lys Gly Ser Pro Gly Ala Asp Gly Pro Ala Gly
        930                 935                 940

Ala Pro Gly Thr Pro Gly Pro Gln Gly Ile Ala Gly Gln Arg Gly Val
945                 950                 955                 960

Val Gly Leu Pro Gly Gln Arg Gly Glu Arg Gly Phe Pro Gly Leu Pro
                965                 970                 975

Gly Pro Ser Gly Glu Pro Gly Lys Gln Gly Pro Ser Gly Ala Ser Gly
            980                 985                 990

Glu Arg Gly Pro Pro Gly Pro Met Gly Pro Pro Gly Leu Ala Gly Pro
        995                 1000                1005

Pro Gly Glu Ser Gly Arg Glu Gly Ala Pro Gly Ala Glu Gly Ser
    1010                1015                1020

Pro Gly Arg Asp Gly Ser Pro Gly Ala Lys Gly Asp Arg Gly Glu
    1025                1030                1035

Thr Gly Pro Ala Gly Pro Pro Gly Ala Pro Gly Ala Pro Gly Ala
    1040                1045                1050

Pro Gly Pro Val Gly Pro Ala Gly Lys Ser Gly Asp Arg Gly Glu
    1055                1060                1065

Thr Gly Pro Ala Gly Pro Thr Gly Pro Val Gly Pro Val Gly Ala
    1070                1075                1080

Arg Gly Pro Ala Gly Pro Gln Gly Pro Arg Gly Asp Lys Gly Glu
    1085                1090                1095

Thr Gly Glu Gln Gly Asp Arg Gly Ile Lys Gly His Arg Gly Phe
    1100                1105                1110

Ser Gly Leu Gln Gly Pro Pro Gly Pro Pro Gly Ser Pro Gly Glu
    1115                1120                1125

Gln Gly Pro Ser Gly Ala Ser Gly Pro Ala Gly Pro Arg Gly Pro
    1130                1135                1140

Pro Gly Ser Ala Gly Ala Pro Gly Lys Asp Gly Leu Asn Gly Leu
    1145                1150                1155

Pro Gly Pro Ile Gly Pro Pro Gly Pro Arg Gly Arg Thr Gly Asp
    1160                1165                1170

Ala Gly Pro Val Gly Pro Pro Gly Pro Pro Gly Pro Pro Gly Pro
    1175                1180                1185

Pro Gly Pro Pro Ser Ala Gly Phe Asp Phe Ser Phe Leu Pro Gln
```

```
                1190                1195                1200
Pro Pro Gln Glu Lys Ala His Asp Gly Gly Arg Tyr Tyr Arg Ala
    1205                1210                1215

Asp Asp Ala Asn Val Val Arg Asp Arg Asp Leu Glu Val Asp Thr
    1220                1225                1230

Thr Leu Lys Ser Leu Ser Gln Gln Ile Glu Asn Ile Arg Ser Pro
    1235                1240                1245

Glu Gly Ser Arg Lys Asn Pro Ala Arg Thr Cys Arg Asp Leu Lys
    1250                1255                1260

Met Cys His Ser Asp Trp Lys Ser Gly Glu Tyr Trp Ile Asp Pro
    1265                1270                1275

Asn Gln Gly Cys Asn Leu Asp Ala Ile Lys Val Phe Cys Asn Met
    1280                1285                1290

Glu Thr Gly Glu Thr Cys Val Tyr Pro Thr Gln Pro Ser Val Ala
    1295                1300                1305

Gln Lys Asn Trp Tyr Ile Ser Lys Asn Pro Lys Asp Lys Arg His
    1310                1315                1320

Val Trp Phe Gly Glu Ser Met Thr Asp Gly Phe Gln Phe Glu Tyr
    1325                1330                1335

Gly Gly Gln Gly Ser Asp Pro Ala Asp Val Ala Ile Gln Leu Thr
    1340                1345                1350

Phe Leu Arg Leu Met Ser Thr Glu Ala Ser Gln Asn Ile Thr Tyr
    1355                1360                1365

His Cys Lys Asn Ser Val Ala Tyr Met Asp Gln Thr Gly Asn
    1370                1375                1380

Leu Lys Lys Ala Leu Leu Leu Gln Gly Ser Asn Glu Ile Glu Ile
    1385                1390                1395

Arg Ala Glu Gly Asn Ser Arg Phe Thr Tyr Ser Val Thr Val Asp
    1400                1405                1410

Gly Cys Thr Ser His Thr Gly Ala Trp Gly Lys Thr Val Ile Glu
    1415                1420                1425

Tyr Lys Thr Thr Lys Thr Ser Arg Leu Pro Ile Ile Asp Val Ala
    1430                1435                1440

Pro Leu Asp Val Gly Ala Pro Asp Gln Glu Phe Gly Phe Asp Val
    1445                1450                1455

Gly Pro Val Cys Phe Leu
    1460

<210> SEQ ID NO 16
<211> LENGTH: 1366
<212> TYPE: PRT
<213> ORGANISM: Homo sapiens
<220> FEATURE:
<221> NAME/KEY: MISC_FEATURE
<223> OTHER INFORMATION: Alpha-2 type I collagen

<400> SEQUENCE: 16

Met Leu Ser Phe Val Asp Thr Arg Thr Leu Leu Leu Leu Ala Val Thr
1               5                   10                  15

Leu Cys Leu Ala Thr Cys Gln Ser Leu Gln Glu Glu Thr Val Arg Lys
                20                  25                  30

Gly Pro Ala Gly Asp Arg Gly Pro Arg Gly Glu Arg Gly Pro Pro Gly
            35                  40                  45

Pro Pro Gly Arg Asp Gly Glu Asp Gly Pro Thr Gly Pro Pro Gly Pro
        50                  55                  60
```

```
Pro Gly Pro Pro Gly Pro Gly Leu Gly Gly Asn Phe Ala Ala Gln
 65                  70                  75                  80

Tyr Asp Gly Lys Gly Val Gly Leu Gly Pro Pro Met Gly Leu Met
                 85                  90                  95

Gly Pro Arg Gly Pro Pro Gly Ala Ala Gly Ala Pro Gly Pro Gln Gly
            100                 105                 110

Phe Gln Gly Pro Ala Gly Glu Pro Gly Glu Pro Gly Gln Thr Gly Pro
        115                 120                 125

Ala Gly Ala Arg Gly Pro Ala Gly Pro Pro Gly Lys Ala Gly Glu Asp
    130                 135                 140

Gly His Pro Gly Lys Pro Gly Arg Pro Gly Glu Arg Gly Val Val Gly
145                 150                 155                 160

Pro Gln Gly Ala Arg Gly Phe Pro Gly Thr Pro Gly Leu Pro Gly Phe
                165                 170                 175

Lys Gly Ile Arg Gly His Asn Gly Leu Asp Gly Leu Lys Gly Gln Pro
                180                 185                 190

Gly Ala Pro Gly Val Lys Gly Glu Pro Gly Ala Pro Gly Glu Asn Gly
            195                 200                 205

Thr Pro Gly Gln Thr Gly Ala Arg Gly Leu Pro Gly Glu Arg Gly Arg
210                 215                 220

Val Gly Ala Pro Gly Pro Ala Gly Ala Arg Gly Ser Asp Gly Ser Val
225                 230                 235                 240

Gly Pro Val Gly Pro Ala Gly Pro Ile Gly Ser Ala Gly Pro Pro Gly
                245                 250                 255

Phe Pro Gly Ala Pro Gly Pro Lys Gly Glu Ile Gly Ala Val Gly Asn
            260                 265                 270

Ala Gly Pro Ala Gly Pro Ala Gly Pro Arg Gly Glu Val Gly Leu Pro
            275                 280                 285

Gly Leu Ser Gly Pro Val Gly Pro Pro Gly Asn Pro Gly Ala Asn Gly
            290                 295                 300

Leu Thr Gly Ala Lys Gly Ala Ala Gly Leu Pro Gly Val Ala Gly Ala
305                 310                 315                 320

Pro Gly Leu Pro Gly Pro Arg Gly Ile Pro Gly Pro Val Gly Ala Ala
                325                 330                 335

Gly Ala Thr Gly Ala Arg Gly Leu Val Gly Glu Pro Gly Pro Ala Gly
            340                 345                 350

Ser Lys Gly Glu Ser Gly Asn Lys Gly Glu Pro Gly Ser Ala Gly Pro
            355                 360                 365

Gln Gly Pro Pro Gly Pro Ser Gly Glu Glu Gly Lys Arg Gly Pro Asn
        370                 375                 380

Gly Glu Ala Gly Ser Ala Gly Pro Pro Gly Pro Pro Gly Leu Arg Gly
385                 390                 395                 400

Ser Pro Gly Ser Arg Gly Leu Pro Gly Ala Asp Gly Arg Ala Gly Val
                405                 410                 415

Met Gly Pro Pro Gly Ser Arg Gly Ala Ser Gly Pro Ala Gly Val Arg
            420                 425                 430

Gly Pro Asn Gly Asp Ala Gly Arg Pro Gly Glu Pro Gly Leu Met Gly
        435                 440                 445

Pro Arg Gly Leu Pro Gly Ser Pro Gly Asn Ile Gly Pro Ala Gly Lys
        450                 455                 460

Glu Gly Pro Val Gly Leu Pro Gly Ile Asp Gly Arg Pro Gly Pro Ile
465                 470                 475                 480

Gly Pro Ala Gly Ala Arg Gly Glu Pro Gly Asn Ile Gly Phe Pro Gly
```

```
                485                 490                 495
Pro Lys Gly Pro Thr Gly Asp Pro Gly Lys Asn Gly Asp Lys Gly His
            500                 505                 510
Ala Gly Leu Ala Gly Ala Arg Gly Ala Pro Gly Pro Asp Gly Asn Asn
            515                 520                 525
Gly Ala Gln Gly Pro Pro Gly Pro Gln Gly Val Gln Gly Gly Lys Gly
            530                 535                 540
Glu Gln Gly Pro Pro Gly Pro Pro Gly Phe Gln Gly Leu Pro Gly Pro
545                 550                 555                 560
Ser Gly Pro Ala Gly Glu Val Gly Lys Pro Gly Glu Arg Gly Leu His
            565                 570                 575
Gly Glu Phe Gly Leu Pro Gly Pro Ala Gly Pro Arg Gly Glu Arg Gly
            580                 585                 590
Pro Pro Gly Glu Ser Gly Ala Ala Gly Pro Thr Gly Pro Ile Gly Ser
            595                 600                 605
Arg Gly Pro Ser Gly Pro Pro Gly Pro Asp Gly Asn Lys Gly Glu Pro
            610                 615                 620
Gly Val Val Gly Ala Val Gly Thr Ala Gly Pro Ser Gly Pro Ser Gly
625                 630                 635                 640
Leu Pro Gly Glu Arg Gly Ala Ala Gly Ile Pro Gly Gly Lys Gly Glu
            645                 650                 655
Lys Gly Glu Pro Gly Leu Arg Gly Glu Ile Gly Asn Pro Gly Arg Asp
            660                 665                 670
Gly Ala Arg Gly Ala Pro Gly Ala Val Gly Ala Pro Gly Pro Ala Gly
            675                 680                 685
Ala Thr Gly Asp Arg Gly Glu Ala Ala Gly Pro Ala Gly Pro Ala Gly
            690                 695                 700
Ala Gly Pro Arg Gly Ser Pro Gly Glu Arg Gly Glu Val Gly Pro Ala
705                 710                 715                 720
Gly Pro Asn Gly Phe Ala Gly Pro Ala Gly Ala Ala Gly Gln Pro Gly
            725                 730                 735
Ala Lys Gly Glu Arg Gly Ala Lys Gly Pro Lys Gly Glu Asn Gly Val
            740                 745                 750
Val Gly Pro Thr Gly Pro Val Gly Ala Ala Gly Pro Ala Gly Pro Asn
            755                 760                 765
Gly Pro Pro Gly Pro Ala Gly Ser Arg Gly Asp Gly Gly Pro Pro Gly
            770                 775                 780
Met Thr Gly Phe Pro Gly Ala Ala Gly Arg Thr Gly Pro Pro Gly Pro
785                 790                 795                 800
Ser Gly Ile Ser Gly Pro Pro Gly Pro Pro Gly Pro Ala Gly Lys Glu
            805                 810                 815
Gly Leu Arg Gly Pro Arg Gly Asp Gln Gly Pro Val Gly Arg Thr Gly
            820                 825                 830
Glu Val Gly Ala Val Gly Pro Pro Gly Phe Ala Gly Glu Lys Gly Pro
            835                 840                 845
Ser Gly Glu Ala Gly Thr Ala Gly Pro Pro Gly Thr Pro Gly Pro Gln
            850                 855                 860
Gly Leu Leu Gly Ala Pro Gly Ile Leu Gly Leu Pro Gly Ser Arg Gly
865                 870                 875                 880
Glu Arg Gly Leu Pro Gly Val Ala Gly Ala Val Gly Glu Pro Gly Pro
            885                 890                 895
Leu Gly Ile Ala Gly Pro Pro Gly Ala Arg Gly Pro Pro Gly Ala Val
            900                 905                 910
```

```
Gly Ser Pro Gly Val Asn Gly Ala Pro Gly Glu Ala Gly Arg Asp Gly
        915                 920                 925

Asn Pro Gly Asn Asp Gly Pro Pro Gly Arg Asp Gly Gln Pro Gly His
    930                 935                 940

Lys Gly Glu Arg Gly Tyr Pro Gly Asn Ile Gly Pro Val Gly Ala Ala
945                 950                 955                 960

Gly Ala Pro Gly Pro His Gly Pro Val Gly Pro Ala Gly Lys His Gly
                965                 970                 975

Asn Arg Gly Glu Thr Gly Pro Ser Gly Pro Val Gly Pro Ala Gly Ala
            980                 985                 990

Val Gly Pro Arg Gly Pro Ser Gly Pro Gln Gly Ile Arg Gly Asp Lys
        995                 1000                1005

Gly Glu Pro Gly Glu Lys Gly Pro Arg Gly Leu Pro Gly Leu Lys
    1010                1015                1020

Gly His Asn Gly Leu Gln Gly Leu Pro Gly Ile Ala Gly His His
    1025                1030                1035

Gly Asp Gln Gly Ala Pro Gly Ser Val Gly Pro Ala Gly Pro Arg
    1040                1045                1050

Gly Pro Ala Gly Pro Ser Gly Pro Ala Gly Lys Asp Gly Arg Thr
    1055                1060                1065

Gly His Pro Gly Thr Val Gly Pro Ala Gly Ile Arg Gly Pro Gln
    1070                1075                1080

Gly His Gln Gly Pro Ala Gly Pro Pro Gly Pro Pro Gly Pro Pro
    1085                1090                1095

Gly Pro Pro Gly Val Ser Gly Gly Gly Tyr Asp Phe Gly Tyr Asp
    1100                1105                1110

Gly Asp Phe Tyr Arg Ala Asp Gln Pro Arg Ser Ala Pro Ser Leu
    1115                1120                1125

Arg Pro Lys Asp Tyr Glu Val Asp Ala Thr Leu Lys Ser Leu Asn
    1130                1135                1140

Asn Gln Ile Glu Thr Leu Leu Thr Pro Glu Gly Ser Arg Lys Asn
    1145                1150                1155

Pro Ala Arg Thr Cys Arg Asp Leu Arg Leu Ser His Pro Glu Trp
    1160                1165                1170

Ser Ser Gly Tyr Tyr Trp Ile Asp Pro Asn Gln Gly Cys Thr Met
    1175                1180                1185

Asp Ala Ile Lys Val Tyr Cys Asp Phe Ser Thr Gly Glu Thr Cys
    1190                1195                1200

Ile Arg Ala Gln Pro Glu Asn Ile Pro Ala Lys Asn Trp Tyr Arg
    1205                1210                1215

Ser Ser Lys Asp Lys Lys His Val Trp Leu Gly Glu Thr Ile Asn
    1220                1225                1230

Ala Gly Ser Gln Phe Glu Tyr Asn Val Glu Gly Val Thr Ser Lys
    1235                1240                1245

Glu Met Ala Thr Gln Leu Ala Phe Met Arg Leu Leu Ala Asn Tyr
    1250                1255                1260

Ala Ser Gln Asn Ile Thr Tyr His Cys Lys Asn Ser Ile Ala Tyr
    1265                1270                1275

Met Asp Glu Glu Thr Gly Asn Leu Lys Lys Ala Val Ile Leu Gln
    1280                1285                1290

Gly Ser Asn Asp Val Glu Leu Val Ala Glu Gly Asn Ser Arg Phe
    1295                1300                1305
```

-continued

```
Thr Tyr Thr Val Leu Val Asp Gly Cys Ser Lys Lys Thr Asn Glu
    1310                1315                1320

Trp Gly Lys Thr Ile Ile Glu Tyr Lys Thr Asn Lys Pro Ser Arg
    1325                1330                1335

Leu Pro Phe Leu Asp Ile Ala Pro Leu Asp Ile Gly Gly Ala Asp
    1340                1345                1350

Gln Glu Phe Phe Val Asp Ile Gly Pro Val Cys Phe Lys
    1355                1360                1365
```

METHODS OF GENERATING AND USING PROCOLLAGEN

RELATED APPLICATIONS

This Application is a National Phase of PCT Patent Application No. PCT/IL2009/000419 having International filing date of Apr. 16, 2009, which claims the benefit of U.S. Provisional Patent Application Nos. 61/129,976 filed on Aug. 4, 2008, and 61/071,267 filed on Apr. 18, 2008. The contents of the above Applications are all incorporated herein by reference.

FIELD AND BACKGROUND OF THE INVENTION

The present invention, in some embodiments thereof, relates to compositions which comprise procollagen and uses of same in promoting wound healing, treating fibrosis and promoting angiogenesis.

The rapid response of the mammalian body to initiate the healing response to prevent life threatening bleeding and infection has evolved to ensure survival, often at the expense of efficient regeneration of the damaged tissue. The wound healing process entails different stages, some being sequential, while others concomitant. However, all stages are carefully orchestrated at the damaged tissue site to regenerate a tissue with normal functionality. The sequence of events involves clotting, inflammation, tissue deposition (migration and proliferation) and finally tissue remodeling.

At the time of tissue injury, blood is released from damaged vessels leading to the formation of a fibrin fiber mesh with platelets entrapped within. The mesh functions as a scaffold for recruited cells to migrate towards and throughout. The activated platelets degranulate and release chemotactic agents including cytokines and growth factors such as transforming growth factor-β1 (TGF-β1), resulting in recruitment of fibroblasts and keratinocytes. Several days after injury the fibroblasts begin to replace the damaged tissue by depositing new collagen matrices. Collagen fibers gradually increase in thickness and align along the stress line of the wound. In normal scar formation, collagen fibers typically align in parallel to the epidermis. This newly formed granulation tissue is eventually organized and contracted into a more dense structure by myofibroblasts.

Scars usually form as a result of the normal progression of the wound healing response and are composed of connective tissue deposited during the healing process. Most scars exhibit a certain degree of both abnormal organization (as seen in scars of the skin) and amounts of connective tissue (as seen in scars of the central nervous system). However, alterations in the normal tissue production cascade result in less than optimal wound healing with excessive deposit of scarring tissue resulting in keloid and hypertrophic scar formation, also termed fibrosis. Hypertrophic scars are characterized by excessive collagen deposition, altered collagen remodeling and contraction and differ from keloid scars in that they are defined within the boundaries of the wound site.

Transforming growth factor-β1 (TGF-β1) plays an important role in these healing processes and has been reported to mediate the transition of fibroblasts into myofibroblasts. This fibroblast subtype is characterized by α-smooth muscle actin (α-SMA) expression and is involved in wound contraction. TGF-β1 induces collagen deposition by upregulation of both mRNA stability and expression of procollagen. In addition, it reduces collagen degradation rates by inhibiting the expression of matrix metalloproteinases (MMPs) while inducing the expression of tissue inhibitors of metalloproteinases (TIMPs).

Aside from the MMP/TIPMP balance, the accessibility of a collagen molecule to such enzymatic activity is also a central factor in determining collagen degradation rates. This accessibility is primarily determined by the organizational state of the collagen (helical monomers versus monomers organized into fibrils) and the extent of crosslinking between collagen triple helices.

Types I and III collagen are fibril-forming collagens, which constitute the bulk of the dermal extracellular matrix. Collagen is synthesized as a procollagen precursor, in which three collagen polypeptides coil into each other, forming the triple helix. These helices are subsequently linked together at the final step of collagen fibril biosynthesis. Type I procollagen consists of two alpha 1 collagen chains and a single alpha 2 chain. Type III is composed of three alpha 1 chains.

In all of the fibrillar collagen molecules, the three polypeptide chains are constructed from a repeating Gly-X-Y triplet, where X and Y can be any amino acid but are frequently the imino acids proline and hydroxyproline. An important feature of fibril forming collagens is that they are synthesized as precursor procollagens containing globular N- and C-terminal extension propeptides.

Each procollagen molecule assembles within the rough endoplasmic reticulum from its three constituent polypeptide chains. As the polypeptide chain is co-translationally translocated across the membrane of the endoplasmic reticulum, hydroxylation of proline and lysine residues occurs within the Gly-X-Y repeat region. Once the polypeptide chain is fully translocated into the lumen of the endoplasmic reticulum, the three pro-alpha chains associate via their C-propeptides to form a trimeric molecule allowing the Gly-X-Y repeat region to form a nucleation point at its C-terminal end, ensuring correct alignment of the chains. The Gly-X-Y region then folds in a C-to-N direction to form a triple helix.

The C-propeptides, and to a lesser extent the N-propeptides, maintain procollagen solubility during its passage out of the cell [Bulleid et al., Biochem Soc Trans. 2000; 28(4): 350-3]. Following or during secretion of procollagen molecules into the extracellular matrix, propeptides are typically cleaved by procollagen N- and C-proteinases, thereby triggering spontaneous self-assembly of collagen molecules into fibrils [Hulmes, 2002 J Struct Biol. 137(1-2):2-10].

Removal of the propeptides by procollagen N- and C-proteinases dramatically lowers the solubility of procollagen and is necessary to initiate the self-assembly of collagen into fibers at 37° C. Crucial to this assembly process are the short non triple-helical peptides called telopeptides which are the remnants of the N- and C-terminal propeptides following digestion with N/C proteinases. These peptides act to ensure correct covalent registration of the collagen molecules within the fibril structure via their crosslinkable aldehydes by lowering the critical concentration necessary for self-assembly (Bulleid et al., 2000, supra).

To date, animal-derived collagen is the major source of collagen for medical applications. Animal-purified collagen is fully processed containing crosslinked telopeptides which render it highly insoluble. Solubilization of animal-purified collagen is typically effected using an extraction method which involves proteolytic removal of the telopeptide region with proteloytic enzymes such as trypsin, yielding atelocollagen which can be solubilized (see U.S. Pat. Nos. 3,934,852; 3,121,049; 3,131,130; 3,314,861; 3,530,037; 3,949,073; 4,233,360 and 4,488,911 for general methods for preparing purified soluble collagen). Atelocollagen undergoes fibrillogenesis under physiological conditions, to form fibers. Such fibers are relatively stable structures, resistant to proteolysis by MMPs. However, these fibers lack the molecular domains found in procollagen, essential to natural wound healing processes and to the natural formation of collagen structures.

As mentioned, alterations in the normal tissue production cascade during the process of wound healing may lead to excessive deposition of scarring tissue resulting in fibrosis.

U.S. Pat. No. 6,448,278 and references therein describe specific procollagen C-proteinase (PCP) inhibitors for the treatment of various medical conditions associated with unregulated production of collagen, including pathological fibrosis or scarring.

Zhang Y et al., 1999, 13(1):51-4 teach direct stimulation of procollagen I (alpha 1) gene expression by administration of platelet-derived wound healing factor (PDWHF).

Saggers, et al., [Wounds 13(2):66-71, 2001] reported that acid-soluble collagen isolated from rat tail tendons inhibits types I and III procollagen mRNA expression in human dermal fibroblasts grown on collagen-coated dishes. The anabolic steroid, oxandrolone, antagonized such collagen substrate inhibition of procollagen mRNA expression. These findings suggest that oxandrolone may directly enhance wound healing by increasing the expression of procollagen mRNA in fibroblasts associated with a collagen matrix analogous to the healing wound.

U.S. Patent App. Nos. 20030199441 and 20050282737 teach medicaments for treating or preventing fibrotic diseases. They describe application of a (poly) peptide with antifibrotic activity, comprising at least one N-terminal procollagen (III) propeptide and a C-terminal procollagen (III) propeptide, or a fragment of the (poly) peptide.

SUMMARY OF THE INVENTION

According to an aspect of some embodiments of the present invention there is provided a method of promoting wound healing, treating fibrosis and/or promoting angiogenesis comprising administering to a subject in need thereof a therapeutically effective amount of a procollagen, thereby promoting wound healing, treating fibrosis and/or promoting angiogenesis in the subject.

According to an aspect of some embodiments of the present invention there is provided use of a procollagen for promoting wound healing, treating fibrosis and/or promoting angiogenesis.

According to an aspect of some embodiments of the present invention there is provided an article of manufacture comprising a packaging material which packages as active ingredients procollagen and an agent for promoting wound healing, treating fibrosis and/or promoting angiogenesis.

According to an aspect of some embodiments of the present invention there is provided a pharmaceutical composition comprising as an active ingredient procollagen and a pharmaceutically acceptable carrier.

According to an aspect of some embodiments of the present invention there is provided a method of purifying procollagen, the method comprising:
 (a) providing a procollagen preparation; and
 (b) purifying the procollagen from the procollagen preparation.

According to some embodiments of the invention, the purifying is effected by a method selected from the group consisting of, gel filtration, salting-out and anion exchange chromatography.

According to some embodiments of the invention, the packaging material comprises at least two separate containers separately packaging the procollagen and the agent for promoting wound healing and/or treating fibrosis.

According to some embodiments of the invention, the article of manufacture of, further comprises instructions for use in promoting wound healing and/or treating fibrosis.

According to some embodiments of the invention, the administering is effected into a tissue area which comprises the wound or a fibrotic tissue.

According to some embodiments of the invention, the administering is effected prior to fibroblast recruitment to the wound.

According to some embodiments of the invention, the procollagen comprises human procollagen.

According to some embodiments of the invention, the procollagen is derived from Type I or Type III collagen.

According to some embodiments of the invention, the procollagen is produced in plant cells.

According to some embodiments of the invention, the procollagen is degradable by collagenase.

According to some embodiments of the invention, the wound is related to a fibrotic condition selected from the group consisting of systemic or localized scleroderma, liver fibrosis, alcoholic cirrhosis, biliary cirrhosis, hepatitis, venoocclusive disease, idiopathic interstitial fibrosis, idiopathic pulmonary fibrosis, interstitial pulmonary fibrosis, acute pulmonary fibrosis, acute respiratory distress syndrome, perimuscular fibrosis, pericentral fibrosis, dermatofibroma, kidney fibrosis, diabetic nephropathy, glomerulonephritis, keloids, hypertrophic scars, joint adhesions, arthrosis, myelofibrosis, corneal scaring, cystic fibrosis, muscular fibrosis, Duchenne's muscular dystrophy, esophageal stricture, retroabdominal scaring, Crohn's disease, ulcerative colitis, atherosclerotic alterations, pulmonary hypertension, angiopathy of the arteries and veins, aneurysms of large vessels or are induced or initiated by scar revisions, plastic surgeries, glaucoma, cataract fibrosis, corneal scaring, graft vs. host disease, tendon surgery, nerve entrapment, Dupuytren's contracture, OB/GYN adhesions, pelvic adhesions, peridural fibrosis, diseases of the thyroid gland or the parathyroids, metastatic bone disease, multiple myeloma and restenosis.

According to some embodiments of the invention, the wound is an acute wound.

According to some embodiments of the invention, the wound is a chronic wound.

According to some embodiments of the invention, the wound is inflicted by diabetes.

According to some embodiments of the invention, the wound is selected from the group consisting of an ulcer, a burn and a surgical wound.

According to some embodiments of the invention, the procollagen comprises monomeric procollagen.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-D are schematic representations of DNA constructs used to generate the tobacco plants of some embodiments of the present invention.

Figures 2A, 2B:
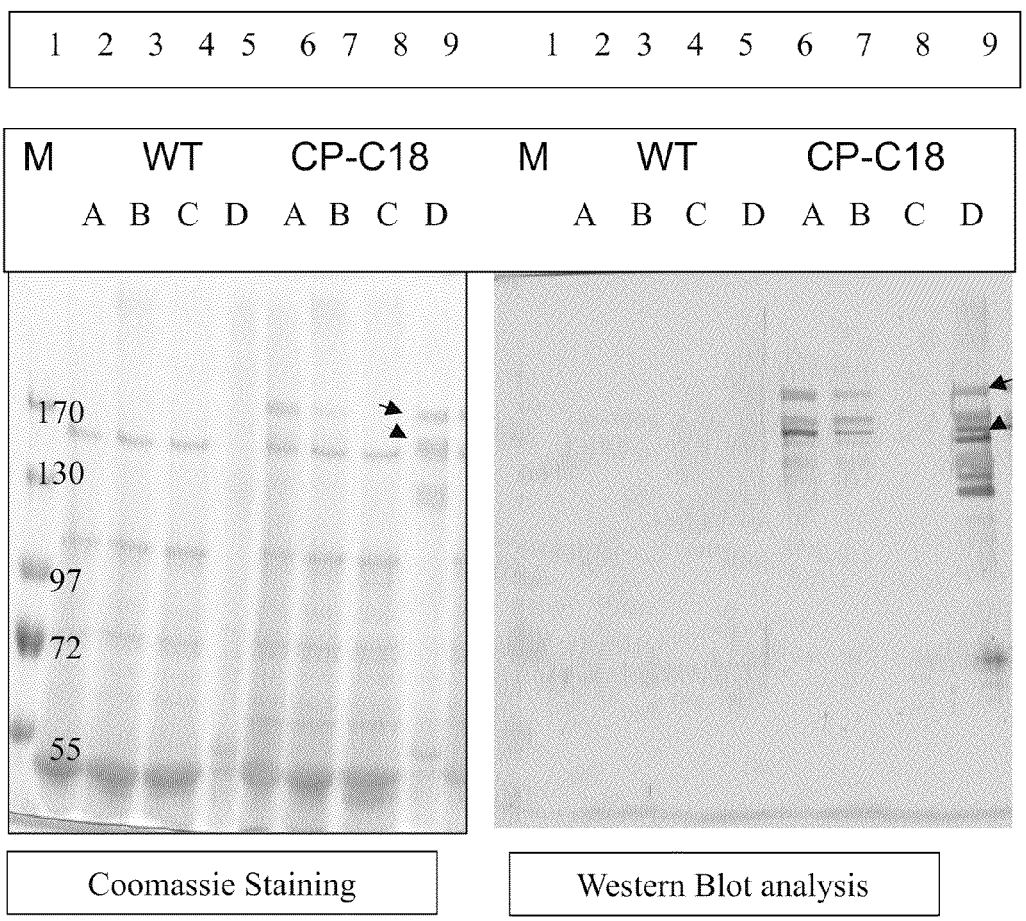

FIGS. 2A-B are images of Coomassie blue-stained SDS PAGE (FIG. 2A) and Western blot analysis (FIG. 2B) showing step-wise purification of procollagen from CP A3-29 transgenic tobacco plants (lot #CP C-18). Lanes represent protein samples separated from either wild type (WT) or CP A3-29 plant lines after homogenization—(Lane A); after centrifugation and saturation with 15% AMS (Lane B); after centrifugation and saturation with 25% AMS (Lane C); and after resuspension of the 25% AMS pellet (Lane D). "M" denotes lanes in which molecular weight markers were loaded.

Figure 3A:
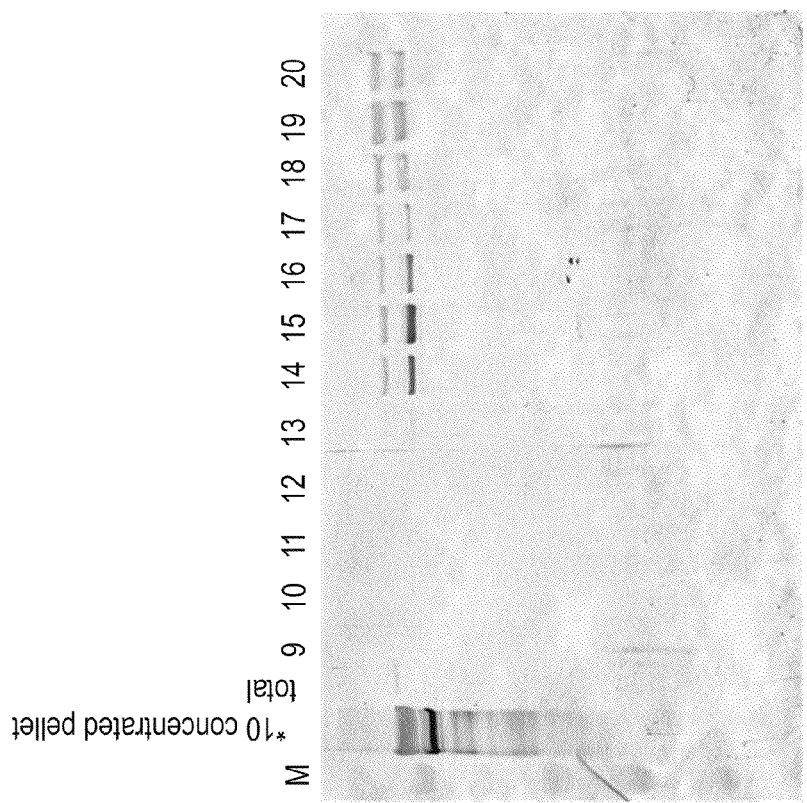
Figure 3B:
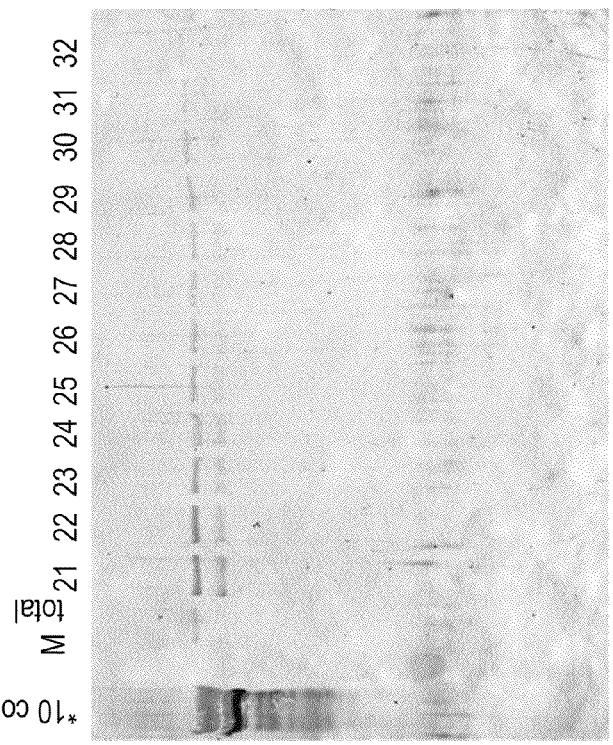

FIGS. 3A-B are images of Western blot analyses of anion exchange fractions #9-20 separated on an 8% SDS-PAGE. The lane labeled "concentrated pellet" corresponds to proteins within the 10-fold-concentrated 25% ammonium sulfate pellet. The lane labeled "Total" corresponds to the protein sample prior to separation on the column.

Figure 4:
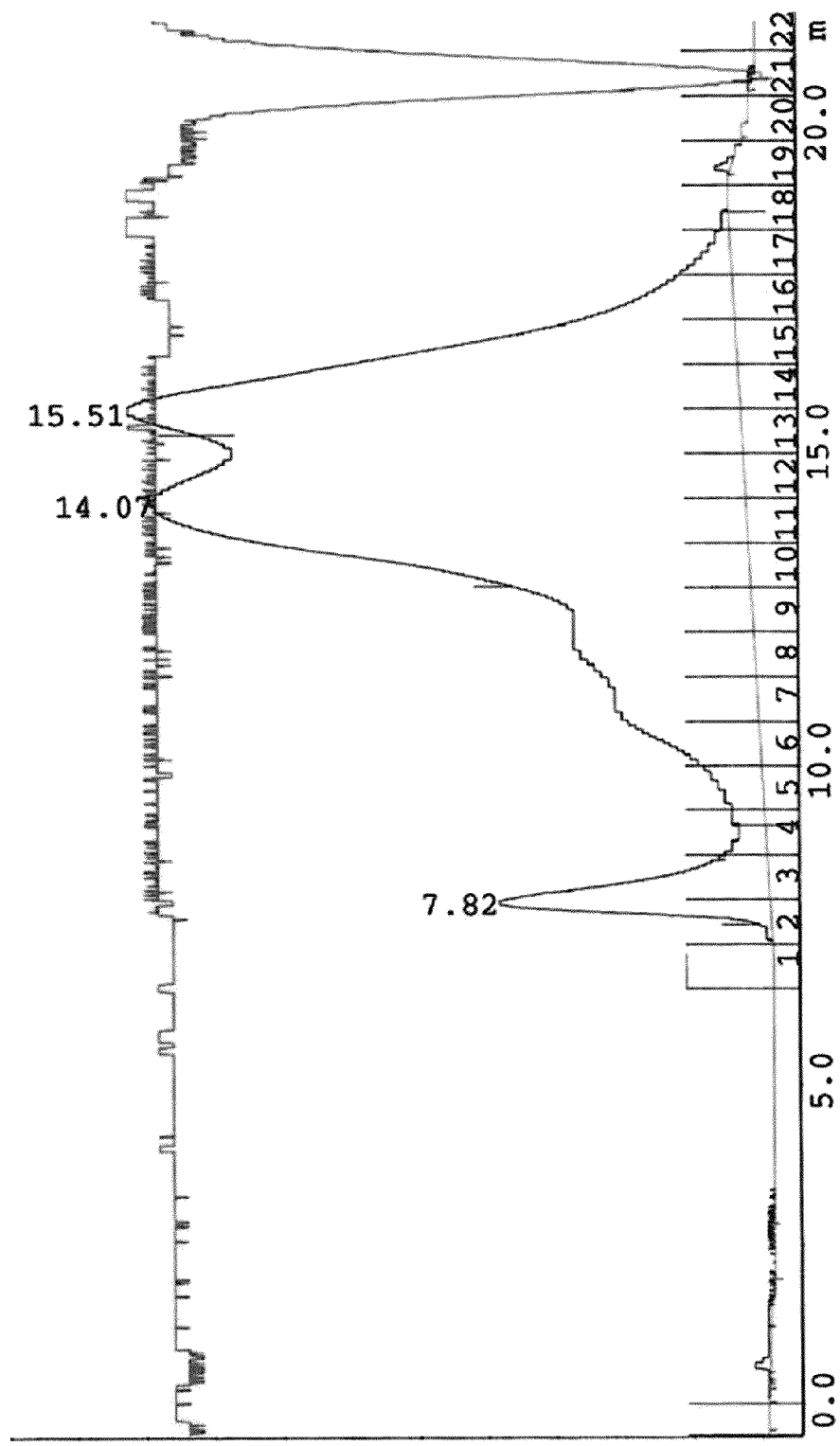

FIG. 4 is a Gel Filtration chromatogram of pooled anion exchange fractions comprising procollagen. Absorbance was measured at 226 nm.

FIGS. 5A-B are silver stain images of gel filtration fractions separated on 8% SDS-PAGE. Samples were run in parallel to a molecular weight protein marker (M) and an unfiltered sample prior (total). Upper arrow: procollagen $\alpha_1$. Lower arrow: procollagen $\alpha_2$.

Figures 6A, 6B:

FIGS. 6A-B are images of Western blot analyses of gel filtration fractions separated on an 8% SDS-PAGE and run in parallel to a molecular weight protein marker (M) and an unfiltered sample prior (total).

Figure 7B:
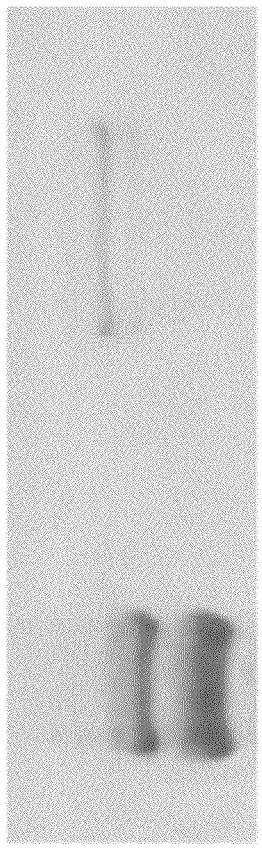
Figure 7A:
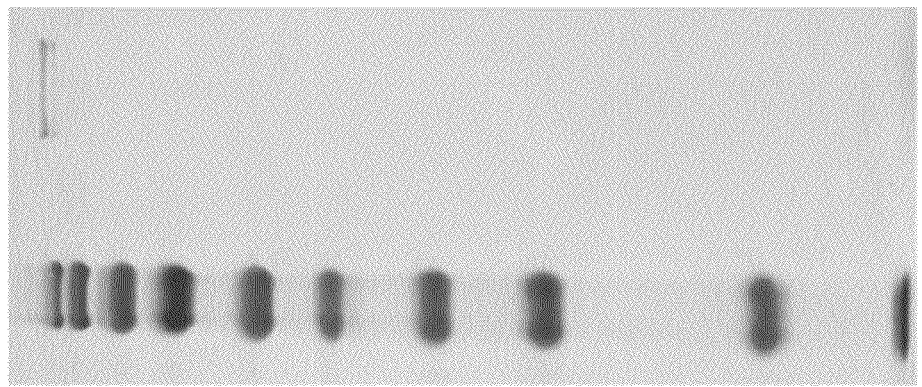

FIGS. 7A-B are scans of instant blue-stained 12% gels following separation of proteins in fractions 3 and 4 following a 10-fold concentration step run in parallel to a protein molecular weight maker (left lane). FIG. 7B is a magnification of the upper section of FIG. 7A.

Figure 8:
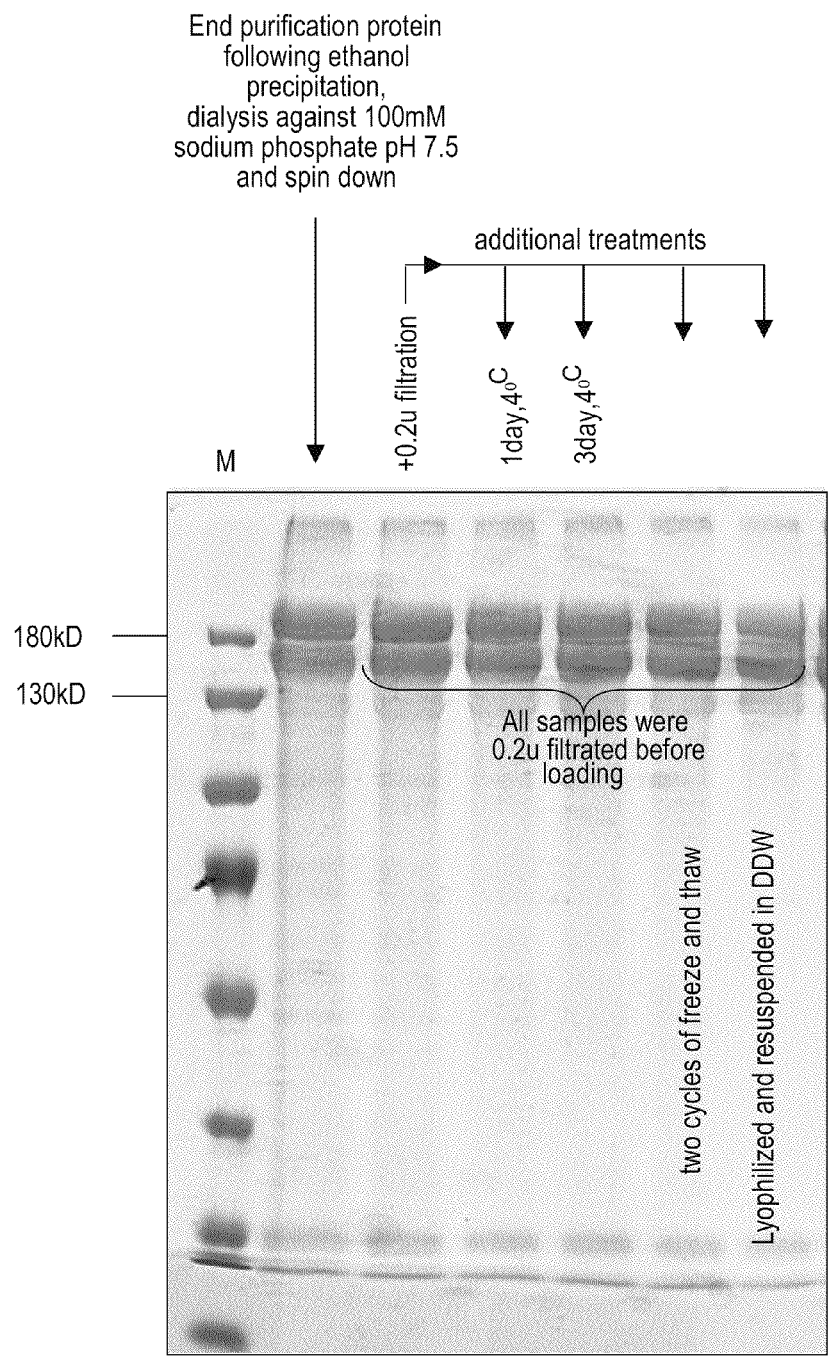

FIG. 8 is a scan of an instant blue-stained SDS-PAGE separation of the AMS-precipitated anion exchange procollagen-containing fraction sample following ethanol precipitation dialysis and spin down (lane 2). Lane 3 includes the same sample following filtration through a 0.2 μm filter. Lanes 4-7 were loaded with samples as in lane 3, following a 24 h (lane 4), or 72 h (lane 5) incubation at 4° C., following two freeze and thaw cycles (lane 6), or following lyophilization and resuspension in DDW (lane 7).

DESCRIPTION OF EMBODIMENTS OF THE INVENTION

The present invention, in some embodiments thereof, relates to compositions and methods for use in wound healing and treatment of fibrosis.

It is to be understood that the invention is not necessarily limited in its application to the details set forth in the following description or exemplified by the Examples. The invention is capable of other embodiments or of being practiced or carried out in various ways.

Although the formation of collagen fibrils is essential to morphogenesis and to healing of wounds and bone fractures in the adult, excessive formation of fibrous collagenous ECM causes much morbidity in the general population. These conditions include keloids (excessive skin scarring), surgical adhesions, and deep-seated fibroses of organs including lungs, liver and kidneys. The deep-seated fibroses are particularly ominous, as the replacement of parenchymal tissue by scar tissue composed essentially of fibrous collagenous ECM destroys organ function.

Whilst reducing the present invention to practice, the present inventors discovered that in sharp contrast to fibrillar collagen, procollagen, as well as acid-soluble atelocollagen or telopeptide-containing collagen isolated by recombinant techniques or from animal tissues can be advantageously used to promote wound healing and prevent scar formation.

Procollagen, as compared to collagen is a nonfibrous, highly soluble substance due to the presence of the C- and N-terminal extensions, herein termed propeptides. Provision of procollagen early in the wound healing process, prior to massive recruitment of fibroblasts provides a readily available soluble substrate to collagenase already present in the wound site resulting in the production of chemotactic collagen fragments, which in turn recruits fibroblasts enhancing the healing process.

Furthermore, procollagen added to the wound site should be readily recognized by natural wound healing elements such as C-propeptide proteinase and N-propeptide proteinase, yielding telopeptide-containing collagen. Telopeptide-containing collagen can be readily incorporated into tissues by natural tissue forming mechanisms which require the presence of the telopeptide region to generate correctly organized collagen deposits. Telopeptide-containing collagen produced by natural elements in the wounded tissue may form tissues with a fiber orientation more closely resembling intact tissues and thus prevent or reduce scar tissue formation. In addition, the released N- and C-propeptides may serve to regulate de-novo synthesis of procollagen thereby preventing fibrosis and scarring.

Thus, according to one aspect of the present invention, there is provided a method of promoting wound healing. The method comprises administering to a subject in need thereof a therapeutically effective amount of a procollagen, thereby promoting wound healing in the subject.

The term "wound" as used herein refers broadly to injuries to the skin, subcutaneous tissue, bone and deep sited organs or connective tissue, initiated in any one of a variety of ways (e.g., pressure sores from extended bed rest, trauma-induced wounds, surgery-related wounds and the like) and with varying characteristics.

As used herein, "wound healing" or "tissue regeneration" refers to the reconstitution of a functional tissue (e.g., skin tissue, bone tissue or mucouos membrane), with minimal or complete absence of fibrous tissue capable of compromising tissue functionality.

Examples of wounds which are the subject of the present teachings include, but are not limited to, bruises, scrapes, burn wounds, sunburn wounds, incisional wounds, excisional wounds, surgical wounds, necrotizing fascitis, ulcers, venous stasis ulcers, diabetic ulcers, decubitus ulcers, aphthous ulcers, scars, alopecia greata, dermatitis, allergic contact dermatitis, atopic dermatitis, berloque dermatitis, diaper dermatitis, dyshidrotic dermatitis, psoriasis, eczema, erythema, warts, anal warts, angioma, cherry angioma, athlete's foot, atypical moles, basal cell carcinoma, Bateman's purpura, bullous pemphigoid, candida, chondrodermatitis helicis, Clark's nevus, cold sores, condylomata, cysts, Darier's disease, dermatofibroma, Discoid Lupus Erythematosus, nummular eczema, atopic eczema, dyshidrotic eczema, hand eczema, Multiforme Erythema Nodosum, Fordyce's Condition, Folliculitis Keloidalis Nuchae, Folliculitis, Granuloma Annulare, Grover's Disease, heat rash, herpes simplex, herpes zoster (shingles), Hidradenitis Suppurativa, Hives, Hyperhidrosis, Ichthyosis, Impetigo, Keratosis Pilaris, Keloids, Keratoacanthoma, Lichen Planus, Lichen Planus Like Keratosis, Lichen Simplex Chronicus, Lichen Sclerosus, Lymphomatoid Papulosis, Lupus of the Skin, Lyme Disease, Lichen Striatus, Myxoid Cysts, Mycosis Fungoides, Molluscum Contagiosum, Moles, Nail Fungus, Necrobiosis Lipoidica Diabeticorum, Nummular Dermatitis, Onychoschizia, Onychomycosis, Pityriasis Lichenoides, Pityriasis Rosea, Pityriasis Rubra Pilaris, Plantar Warts, Poison Ivy, Poison Oak, Pompholyx, Pseudofolliculitis Barbae, Pruritus Ani and Pityriasis Alba.

Wounds are typically classified into one of four grades depending on the depth of the wound: (i) Grade I: wounds limited to the epithelium; (ii) Grade II: wounds extending into the dermis; (iii) Grade III: wounds extending into the subcutaneous tissue; and (iv) Grade IV, also known as full-thickness wounds: wounds wherein bones are exposed (e.g., a bony pressure point such as the greater trochanter or the sacrum).

The term "partial thickness wound" used herein refers to wounds that encompass Grades I-III; examples of partial thickness wounds include burn wounds, pressure sores, venous stasis ulcers, and diabetic ulcers.

The term "full thickness wound" used herein is meant to include both Grade III and Grade IV wounds.

The term "chronic wound" used herein refers to a wound that has stalled and that has not healed within thirty days.

As mentioned, the procollagen of the present invention may be useful for treating wounds in the bone. It will be appreciated however that the procollagen may also be useful for treating other bone disorders including, but not limited to osteoporosis (including postmenopausal osteoporosis, male and female senile osteoporosis and corticosteroid-induced osteoporosis), osteoarthritis, Paget's disease, osteomalacia, prolonged bed rest, chronic disuse of a limb, anorexia, microgravity, exogenous and endogenous gonadal insufficiency, bone fracture, non-union, defect, prosthesis implantation and the like.

As explained in detail in the background section, formation of fibrotic tissue is an integral part of wound healing. However, in some cases during the healing process or in patients with fibrotic conditions or diseases, collagen production may be qualitatively altered or mislocalized to the extracellular space. In such diseases, the fibrotic tissue becomes rigid, firm and nonelastic.

Thus, according to further embodiments of this aspect of the present invention there is provided a method of treating fibrosis.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the phrase "medical conditions associated with fibrosis" refers to medical conditions which result from fibrosis or in which fibrosis occurred during the progression of the disease or syndrome.

Fibrotic diseases are induced or initiated by scar revisions, plastic surgeries, glaucoma, cataract fibrosis, corneal scaring, graft vs. host disease, tendon surgery, nerve entrapment, Dupuytren's contracture, OB/GYN adhesions, pelvic adhesions, infertility, peridural fibrosis, diseases of the thyroid gland or the parathyroids, metastatic bone disease, multiple myeloma, or restenoses.

Specific examples of medical conditions associated with fibrosis include, but are not limited to, systemic or localized scleroderma, liver fibrosis of various etiologies, alcoholic cirrhosis, e.g. alcoholic liver cirrhosis, biliary cirrhosis, hepatitis of viral or other origin, veno-occlusive disease, idiopathic interstitial fibrosis, idiopathic pulmonary fibrosis, interstitial pulmonary fibrosis, acute pulmonary fibrosis, acute respiratory distress syndrome, perimuscular fibrosis, pericentral fibrosis, dermatofibroma, kidney fibrosis, diabetic nephropathy, glomerulonephritis, keloids, hypertrophic scars, joint adhesions, arthrosis, myelofibrosis, corneal scaring, cystic fibrosis, muscular fibrosis, Duchenne's muscular dystrophy, esophageal stricture, retroabdominal scaring, Crohn's disease, ulcerative colitis, atherosclerotic alterations, pulmonary hypertension, angiopathy of the arteries and veins, aneurysms of large vessels.

The procollagen of the present invention may also be useful for promoting angiogenesis (e.g. at a site of a wound, during tissue remodeling, following ischemic stroke, ischemic heart disease and gastrointestinal lesions).

The term "angiogenesis" as used herein, refers to the de novo formation of vessels such as that arising from vasculogenesis as well as those arising from branching and sprouting of existing vessels, capillaries and venules.

The term "procollagen" as used herein, refers to a collagen molecule (e.g. human) that comprises either an N-terminal propeptide, a C-terminal propeptide or both. Exemplary human procollagen amino acid sequences are set forth by SEQ ID NOs: 1, 2, 7, 8 and 12 and 13.

Procollagen may comprise polypeptides of any fibril-forming collagens (types I, II, III, V, and XI), networks forming collagens (types IV, VIII, and X), collagens associated with fibril surfaces (types IX, XII, and XIV), collagens which occur as transmembrane proteins (types XIII and XVII), or collagens which form 11-nm periodic beaded filaments (type VI). According to embodiments of this aspect of the present invention, the procollagen comprises an alpha 1 and/or 2 chain of type I collagen $\{e.g., [\alpha_1(I)]_2 \alpha_2(I); [\alpha_1(I)]3)\}$ or collagen (III) homotrimers $[\alpha_1(III)]3$ According to some embodiments of this aspect of the present invention, the procollagen is provided in a monomeric form (due to steric hindrance that the propeptides form, and as such is an intrinsic property of the procollagen molecule).

Although the use of collagenase-catalyzed procollagen fragments is advantageous as a source for signaling, application of genetically modified forms of procollagen may be preferred when attempting to recruit fibroblasts to a particular tissue or to establish functional tissue architecture. More specifically, collagenase-resistant collagens and the like may be preferred for such purposes [Wu et al., Proc Natl. Acad Sci, Vol. 87, p. 5888-5892, 1990].

The recombinant human procollagen may be expressed in any cell, including but not limited to prokaryotic cells (e.g., bacteria), plant cells and other eukaryotic cells such as yeast and fungus, as long as the procollagen is not subject to the activity of N and/or C proteinases.

Recombinant synthesis of procollagen in yeast has been described in U.S. Pat. No. 5,593,859, which is hereby incorporated by reference in its entirety.

Recombinant synthesis of procollagen in plants has been described in U.S. Pat. No. 6,617,431, which is hereby incorporated by reference in its entirety.

Plants in which the human procollagen may be produced (i.e. expressed) may be any lower (e.g. moss and algae) or higher (vascular) plant, and can include tissues or isolated cells and extracts thereof (e.g., of a cell suspension). Preferred plants are those which are capable of accumulating large amounts of collagen chains, collagen and/or the processing enzymes described herein below. Such plants may also be selected according to their resistance to stress conditions and the ease at which expressed components or assembled collagen can be extracted. Examples of plants in which human procollagen may be expressed include, but are not limited to tobacco, maize, alfalfa, rice, potato, soybean, tomato, wheat, barley, canola, carrot, lettuce and cotton.

Production of recombinant human procollagen is typically effected by stable or transient transformation with an exogenous polynucleotide sequence encoding human procollagen.

Exemplary polynucleotide sequences encoding human procollagen are set forth by SEQ ID NOs: 3 and 4.

The stability of the triple-helical structure of collagen requires the hydroxylation of prolines by the prolyl-4-hydroxylase (P4H) enzyme to form hydroxyproline residues within the collagen chain. Although plants are capable of synthesizing hydroxyproline-containing proteins, the prolyl hydroxylase responsible for synthesis of hydroxyproline in plant cells exhibits relatively loose substrate sequence specificity as compared with mammalian P4H and thus, production of collagen with hydroxyproline only at the Y position of Gly-X-Y triplets requires co-expression of collagen and human or mammalian P4H genes.

Thus, according to one embodiment, the procollagen is expressed in a subcellular compartment of a plant that is devoid of endogenous P4H activity so as to avoid incorrect hydroxylation thereof. As is used herein, the phrase "subcellular compartment devoid of endogenous P4H activity" refers to any compartmentalized region of the cell which does not include plant P4H or an enzyme having plant-like P4H activity. According to one embodiment, the subcellular compartment is a vacuole.

Accumulation of the expressed procollagen in a subcellular compartment devoid of endogenous P4H activity can be effected via any one of several approaches.

For example, the expressed procollagen can include a signal sequence for targeting the expressed protein to a subcellular compartment such as the apoplast or an organelle (e.g. chloroplast). Examples of suitable signal sequences include the chloroplast transit peptide (included in Swiss-Prot entry P07689, amino acids 1-57, SEQ ID NO: 10) and the Mitochondrion transit peptide (included in Swiss-Prot entry P46643, amino acids 1-28, SEQ ID NO: 11).

Alternatively, the sequence of the procollagen can be modified in a way which alters the cellular localization of the procollagen when expressed in plants.

Some embodiments of the present invention therefore contemplate genetically modified cells co-expressing both human procollagen and a P4H, capable of correctly hydroxylating the procollagen alpha chain(s) [i.e. hydroxylating only the proline (Y) position of the Gly-X-Y triplets]. P4H is an enzyme composed of two subunits, alpha and beta as set forth in Genbank Nos. P07237 and P13674. Both are needed to form an active enzyme while the beta subunit also possesses chaperon and protein disulfide isomerase function.

The P4H expressed by the genetically modified cells of the present invention is preferably a human P4H which is encoded by, for example, SEQ ID NOs: 5 and 6. In addition, P4H mutants which exhibit enhanced substrate specificity, or P4H homologues can also be used. A suitable P4H homologue is exemplified by an *Arabidopsis* oxidoreductase identified by NCBI accession NP_179363.

Since P4H is required to co-accumulate with the expressed procollagen chain, the coding sequence thereof is preferably modified accordingly (e.g. by addition or deletion of signal sequences such as for vacuolar targeting).

In mammalian cells, collagen is also modified by Lysyl hydroxylase, galactosyltransferase and glucosyltransferase. These enzymes sequentially modify lysyl residues at specific positions to hydroxylysyl, galactosylhydroxylysyl and glucosylgalactosyl hydroxylysyl residues. A single human enzyme, Lysyl hydroxylase 3 (LH3), as set forth in Genbank No. 060568, can catalyze all three consecutive steps in hydroxylysine linked carbohydrate formation [Wang et al. Matrix Biol. 2002 November; 21(7):559-66].

Thus, the genetically modified cells of the present invention may also express mammalian LH3. An LH3-encoding sequence such as that set forth by SEQ ID NO: 9 can be used for such purposes.

The procollagen(s) and modifying enzymes described above can be expressed from a stably integrated or a transiently expressed nucleic acid construct which includes polynucleotide sequences encoding the procollagen alpha chains and/or modifying enzymes (e.g. P4H and LH3) positioned under the transcriptional control of functional promoters. Such a nucleic acid construct (also termed herein as an expression construct) can be configured for expression throughout the whole organism e.g. plant, defined tissues or defined cells, or at defined developmental stages of the organism. Such a construct may also include selection markers (e.g. antibiotic resistance), enhancer elements and an origin of replication for bacterial replication.

It will be appreciated that constructs including two expressible inserts (e.g. two alpha procollagen chain types, or an alpha chain and P4H) preferably include an individual promoter for each insert, or alternatively such constructs can express a single transcript chimera including both insert sequences from a single promoter. In such a case, the chimeric transcript may include an IRES sequence between the two insert sequences such that the downstream insert can be translated therefrom.

Numerous functional expression promoters and enhancers which can be either tissue specific, developmentally specific, constitutive or inducible can be utilized by the constructs of the present invention, some examples are provided hereinunder.

As used herein in the specification, the phrase "plant promoter" or "promoter" includes a promoter which can direct gene expression in cells (including DNA containing organelles) of plants, fungus and yeast. Such a promoter can be derived from plant, bacterial, viral, fungal or animal origin. Such a promoter can be constitutive, i.e., capable of directing high levels of gene expression in a plurality of tissues, tissue-specific, i.e., capable of directing gene expression in a particular tissue or tissues, inducible, i.e., capable of directing gene expression under a stimulus, or chimeric, i.e., formed of portions of at least two different promoters.

Thus, the plant promoter employed can be a constitutive promoter, a tissue-specific promoter, an inducible promoter or a chimeric promoter.

Examples of constitutive promoters include, without being limited to, CaMV35S and CaMV19S promoters, FMV34S promoter, sugarcane bacilliform badnavirus promoter, CsVMV promoter, *Arabidopsis* ACT2/ACT8 actin promoter,

*Arabidopsis* ubiquitin UBQ1 promoter, barley leaf thionin BTH6 promoter, and rice actin promoter.

Examples of tissue-specific promoters include, without being limited to, bean phaseolin storage protein promoter, DLEC promoter, PHS promoter, zein storage protein promoter, conglutin gamma promoter from soybean, AT2S1 gene promoter, ACT11 actin promoter from *Arabidopsis*, napA promoter from *Brassica napus* and potato patatin gene promoter.

The inducible promoter is a promoter induced by a specific stimulus such as stress conditions comprising, for example, light, temperature, chemicals, drought, high salinity, osmotic shock, oxidative conditions or pathogenic-related stress and include, without being limited to, the light-inducible promoter derived from the pea rbcS gene, the promoter from the alfalfa rbcS gene, the promoters DRE, MYC and MYB active in drought; the promoters INT, INPS, prxEa, Ha hsp17.7G4 and RD21 active in high salinity and osmotic stress, and the promoters hsr203J and str246C active in pathogenic stress.

The promoter utilized in the present invention should preferably be a strong constitutive promoter such that overexpression of the construct inserts is effected following transformation.

It will be appreciated that any of the construct types used in the present invention can be co-transformed into the same cells using same or different selection markers in each construct type. Alternatively the first construct type can be introduced into a first organism e.g. plant while the second construct type can be introduced into a second isogenic plant, following which the transgenic plants resultant therefrom can be crossed and the progeny selected for double transformants. Further self-crosses of such progeny can be employed to generate lines homozygous for both constructs.

A number of vectors containing constitutive or inducible promoters can be used for transforming yeast cells. For a review, see Current Protocols in Molecular Biology, Vol. 2, 1988, ed. Ausubel et al., Greene Publish. Assoc. & Wiley Interscience, ch. 13; Grant et al., 1987, "Expression and Secretion Vectors for Yeast," in Methods in Enzymol. 153: 516-544; Glover, 1986, DNA Cloning, Vol. II, IRL Press, Wash., D.C., Ch. 3; and Bitter, 1987, "Heterologous Gene Expression in Yeast," in Methods in Enzymol. 152:673-684. A constitutive yeast promoter such as ADH or Leu2 or an inducible promoter such as GAL can be used ("Cloning in Yeast," ch. 3, R. Rothstein In: DNA Cloning, Vol. 11, A Practical Approach, Ed. D. M. Glover, 1986, IRL Press, Wash. D.C.). Alternatively, vectors which promote integration of foreign DNA sequences into the yeast chromosome can be used.

There are various methods of introducing nucleic acid constructs into both monocotyledonous and dicotyledenous plants (Potrykus, I., Annu. Rev. Plant. Physiol., Plant. Mol. Biol. (1991) 42:205-225; Shimamoto et al., Nature (1989) 338:274-276). Such methods rely on either stable integration of the nucleic acid construct or a portion thereof into the genome of the plant, or on transient expression of the nucleic acid construct in which case these sequences are not inherited by progeny of the plant.

In addition, several methods exist in which a nucleic acid construct can be directly introduced into the DNA of a DNA-containing organelle such as a chloroplast.

There are two principle methods of effecting stable genomic integration of exogenous sequences such as those included within the nucleic acid constructs of the present invention into plant genomes:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S, and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation (Horsch et al. in Plant Molecular Biology Manual A5, Kluwer Academic Publishers, Dordrecht (1988) p. 1-9). A supplementary approach employs the *Agrobacterium* delivery system in combination with vacuum infiltration. The *Agrobacterium* system is especially viable in the creation of transgenic dicotyledenous plants.

There are various methods of direct DNA transfer into plant cells. In electroporation, protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals, tungsten particles or gold particles, and the microprojectiles are physically accelerated into cells or plant tissues.

Following transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Transient expression methods which can be utilized for transiently expressing the isolated nucleic acid included within the nucleic acid construct of the present invention include, but are not limited to, microinjection and bombardment as described above but under conditions which favor transient expression, and viral mediated expression wherein a packaged or unpackaged recombinant virus vector including the nucleic acid construct is utilized to infect plant tissues or cells such that a propagating recombinant virus established therein expresses the non-viral nucleic acid sequence.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, the constructions can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of the present invention is demonstrated by the above references as well as in U.S. Pat. No. 5,316,931.

A technique for introducing exogenous nucleic acid sequences to the genome of the chloroplasts is known. This technique involves the procedures as described below. First, the exogenous nucleic acid is introduced via particle bombardment into the cells with the aim of introducing at least one exogenous nucleic acid molecule into the chloroplasts. The exogenous nucleic acid is selected such that it is integratable into the chloroplast's genome via homologous recombination which is readily effected by enzymes inherent to the chloroplast. To this end, the exogenous nucleic acid includes, in addition to a gene of interest, at least one nucleic acid stretch which is derived from the chloroplast's genome. In addition, the exogenous nucleic acid includes a selectable marker, which serves by sequential selection procedures to ascertain that all or substantially all of the copies of the chloroplast genomes following such selection include the exogenous nucleic acid. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Regardless of the technique used for transformation, once procollagen-expressing progeny are identified, such plants are further cultivated under conditions which maximize expression thereof. Progeny resulting from transformed plants can be selected, by verifying presence of exogenous mRNA and/or polypeptides by using nucleic acid or protein probes (e.g. antibodies). The latter approach enables localization of the expressed polypeptide components (by for example, probing fractionated plants extracts) and thus also verifies a potential for correct processing and assembly.

Following cultivation of such plants, the procollagen is typically harvested. Plant tissues/cells are preferably harvested at maturity, and the procollagen molecules are isolated using any biochemical method known in the art.

Thus, embodiments of the present invention further provide for a method of purifying procollagen.

The method comprising providing procollagen preparation and purifying the procollagen.

Procollagen may be generated using any method known in the art (for example those described above).

Procollagen may be fully purified or partially purified using any protein purification technique known in the art. These methods are typically based on size, charge or binding affinity purification.

According to one embodiment, the procollagen is comprised in a procollagen-containing composition, in which at least 0.1%, at least 0.25%, at least 0.5%, at least 1%, at least 2.5%, at least 5%, at least 10%, at least 20%, at least 30%, at least 40%, at least 50%, at least 60%, at least 70%, at least 80%, at least 90%, at least 92%, at least 93%, at least 94%, at least 95%, at least 96%, at least 97%, at least 99% or 100% is procollagen. Other components comprised in the procollagen composition may include but are not limited to collagen, hyaluronic acid, alginate, carboxymethylcellulose, hydroxymethylcellulose, hydroxyethylcellulose, oxidized cellulose, cellulose whiskers, and starch.

As used herein, "purifying" refers to the isolation of the protein from its natural environment or site of accumulation within the recombinant host. Separation from small molecules is typically effected by dialysis such as using cellulose membranes. Gel-filtration chromatorgraphy is typically used as a more discriminative technique. Alternatively or additionally, salting-out is used, such as with ammonium sulfate which is typically used for protein purification e.g., to precipitate fibrinogen. Yet alternatively or additionally, ion exchange chromatography is used to separate procollagen on the basis of net charge. Affinity chromatography is another powerful approach for isolation of proteins of interest. More specifically, antibodies can be used or affinity-binding methods based on the protein's natural attractive forces to certain chemical groups.

Exemplary methods of purifying or semi-purifying procollagen of the present invention are described in detail in the Examples section which follows.

Regardless of the method of production, once the procollagen is at hand it can be administered to the subject per se or in a pharmaceutical composition.

As used herein, a "pharmaceutical composition" refers to a preparation of the active ingredients described herein with other chemical components such as physiologically suitable carriers and excipients. The purpose of the pharmaceutical composition is to facilitate administration of the active ingredients (e.g., procollagen) to the subject.

As used herein, the term "active ingredient" refers to the procollagen accountable for the intended biological effect (i.e., promoting wound healing and treating fibrosis).

Hereinafter, the phrases "physiologically acceptable carrier" and "pharmaceutically acceptable carrier", which may be interchangeably used, refer to a carrier or a diluent that do not cause significant irritation to the subject and do not abrogate the biological activity and properties of the administered active ingredients. An adjuvant is included under these phrases.

Herein, the term "excipient" refers to an inert substance added to the pharmaceutical composition to further facilitate administration of an active ingredient of the present invention.

Techniques for formulation and administration of drugs may be found in "Remington's Pharmaceutical Sciences," Mack Publishing Co., Easton, Pa., latest edition, which is incorporated herein by reference.

The pharmaceutical composition may be formulated as a unit dosage form. In such form, the preparation is subdivided into unit doses containing appropriate quantities of the active ingredients such as for a single administration. The unit dosage form can be a packaged preparation, the package containing discrete quantities of preparation, for example, an adhesive bandage, a non-adhesive bandage, a wipe, a baby wipe, a gauze, a pad and a sanitary pad.

The pharmaceutical compositions of the present invention may be applied in a local manner, for example, via administration of the compositions directly onto a tissue region (e.g. wound) of the subject. Suitable routes of administration of pharmaceutical compositions may, for example, include topical (e.g., to a keratinous tissue, such as the skin, hair, nail, scalp), subcutaneous, mucosal (e.g., oral, vaginal, eye), intramascular administrations.

The pharmaceutical compositions of the present invention may also be applied via injecting the composition including the active ingredient and a physiologically acceptable carrier. For local administration, the compositions may be injected into the wound, and/or into healthy tissue (e.g., skin) that surrounds the wounded tissue, or both e.g., subcutaneous.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

The active ingredient may also be in a powder form for constitution with a suitable vehicle, e.g., sterile, pyrogen-free water based solution, before use.

Pharmaceutical compositions for use in accordance with the present invention thus may be formulated in conventional manner using one or more physiologically acceptable carriers comprising excipients and auxiliaries, which facilitate processing of the active ingredients into preparations. Proper formulation is dependent upon the administration approach chosen.

Determination of a therapeutically effective amount is well within the capability of those skilled in the art, especially in light of the detailed disclosure provided herein. Treatment can be effected prior to the formation of massive scar tissue, such as prior to the recruitment of fibroblasts to the affected site. However, the present invention also envisages administering the procollagen at any other stage of healing.

For any preparation used in the method of the invention, the therapeutically effective amount or dose can be estimated initially from in vitro assays. In addition, a dose can be formulated in tissue culture systems or in animal models to achieve a desired concentration or titer. Animal models may be used in order to establish criteria for administration. For example, a diabetic rat or mouse wound model may be used [Galeano et al., Diabetes. (2004) 53(9):2509-17]. Outcome measures such as perfusion and survival, as well as histological and functional criteria, can be employed to assess the efficacy of the different parameters, in order to approach optimal efficiency.

Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the type of formulation employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Depending on the severity of the condition (e.g., the area, depth and degree of the wound or the scar) and the responsiveness of the skin, dosing can be of a single or a plurality of administrations, with course of treatment ranging from several days to several weeks or until cure is effected or diminution of the condition is achieved. In exemplary embodiments, the pharmaceutical composition of the present invention is administered at least once a day.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA-approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

Since the pharmaceutical compositions of the present invention are utilized in vivo, the compositions are preferably of high purity and substantially free of potentially harmful contaminants, e.g., at least National Food (NF) grade, generally at least analytical grade, and preferably at least pharmaceutical grade. To the extent that a given compound must be synthesized prior to use, such synthesis or subsequent purification shall preferably result in a product that is substantially free of any potentially contaminating toxic agents that may have been used during the synthesis or purification procedures.

To improve therapeutic efficacy, additional agents may be incorporated into the pharmaceutical compositions of the present invention. Agents for promoting wound healing, treating fibrosis and/or promoting angiogenesis can be formulated in a single composition together with the procollagen (e.g., single container) or when desired, packed in separate containers and included in an article of manufacture, which may further comprise instructions for use. Such agents include, but are not limited to, extracellular matrix components (e.g. vitronectin, laminin, collagen, elastin), growth factors (e.g. FGF 1, FGF 2, IGF 1, IGF 2, PDGF, EGF, KGF, HGF, VEGF, SDF-1, GM-CSF, CSF, G-CSF, TGF alpha, TGF beta, NGF, PDWHF and ECGF), hypoxia inducible factors (e.g. HIF-1 alpha and beta and HIF-2), hormones (e.g., insulin, growth hormone (GH), CRH, Leptin, Prolactin, oxandrolone and TSH), angiogenic factors (e.g., angiogenin and angiopoietin), coagulation and anticoagulation factors (e.g., Factor I, Factor XIII, tissue factor, calcium, vWF, protein C, protein S, protein Z, fibronectin, antithrombin, heparin, plasminogen, low molecular weight heparin (Clixan), high molecular weight kininogen (HMWK), prekallikrein, plasminogen activator inhibitor-1 (PAI1), plasminogen activator inhibitor-2 (PAI2), urokinase, thrombomoduline, tissue plasminogen activator (tPA), alpha 2-antiplasmin and Protein Z-related protease inhibitor (ZPI)), cytokines (IL-1 alpha, IL-1 beta, IL-2, IL-3, IL-4, IL-5, IL-6, IL-7, IL-8, IL-9, IL-10, IL-11, IL-12, IL-13 and IFN-alpha, IFN, beta, and IFN-gamma), Bone morphogenetic proteins (BMPs), chemokines (e.g., MCP-1 or CCL2), enzymes (e.g. endoglycosidases, exoglycosidases, endonucleases, exonucleases, peptidases, lipases, oxidases, decarboxylases, hydrases, chondroitinase, chondroitinase ABC, chondroitinase AC, hyaluronidase, keratanase, heparanases, heparanase splice variance, collagenase, trypsin, catalases), neurotransmitters (e.g., acetylcholine and monoamines), neuropeptides (e.g. substance P), vitamins (e.g., D-biotin, Choline Chloride, Folic acid, Myo-inositol, Niacinamide, D-Pantothenic acid, Calcium salts, Pyridoxal.HCl, Pyrodixine.HCl, Riboflavin, Thiamine.HCl, Vitamin B12, vitamin E, vitamin C, vitamin D, vitamin B1-6, vitamin K, vitamin A and vitamin PP), carbohydrates (e.g. Mono/Di/Polysacharides including glucose, mannose, maltose and fructose), ions, chelators (e.g. Fe chelators, Ca chelators), antioxidants (e.g., Vitamin E, Quarcetin, superoxide scavengers, Superoxide dismutase, $H_2O_2$ scavengers, free radicals scavengers, Fe scavengers), fatty acids (e.g., Triglycerides, Phospholipids, Cholesterols, free fatty acids and non free fatty acids, fatty alcohol, Linoleic acid, oleic acid and lipoic acid), antibiotics (e.g., Penicillins, Cephalosporins and Tetracyclines), analgesics, anesthetics, antibacterial agents, anti-yeast agents, anti-fungal agents, antiviral agents, probiotic agents, anti-protozal agents, anti-pruritic agents, anti-dermatitis agents, anti-emetics, anti-inflammatory agents, anti-hyperkeratolyic agents, antiperspirants, anti-psoriatic agents, anti-seborrheic agents, antihistamine agents, amino acids (e.g., essential and nonessential, especially glutamine and arginine), salts sulfates (e.g. Calcium Sulfate), steroids (e.g., androgens, estrogens, progestagens, glucocorticoids and mineralocorticoids), catecholamines (e.g., Epinephrine and Nor-epinephrine), Nucleosides and Nucleotides (e.g., Purins and Pyrimidines), Prostaglandins (e.g. Prostaglandin E2), Leucotriens, Erythropoietins (e.g. Thrombopoietin), Proteoglycans (e.g. Heparan sulfate, keratan sulfate), Hydroxyapatites (e.g. Hydroxyapatite ($Ca_{10}PO_4)_6(OH)_2$)), Haptoglobins (Hp1-1, Hp2-2 and Hp1-2), Superoxide dismutases (e.g. SOD 1/2/3), Nitric Oxides, Nitric Oxide donors (e.g. nitroprusside, Sigma Aldrich, St. Louis, Mo., USA, Glutathione peroxidases, Hydrating compounds (e.g. vasopressin), cells (e.g. Platelets), cell medium (e.g. M199, DMEM/F12, RPMI, Iscovs), serum (e.g. human serum, fetal calf serum, fetal bovine serum), buffers (e.g., HEPES, Sodium Bicarbonate), detergents (e.g., Tween), disinfectants, herbs, fruit extracts, vegetable extracts (e.g. cabbage, cucumber), flower extracts, plant extracts, flavinoids (e.g. pomegranate juice), spices, leaves (e.g. Green tea, Chamomile), Polyphenols (e.g. Red Wine), honey, lectins, microparticles, nanoparticles (liposomes), micelles, calcium carbonate ($CaCO_3$, e.g. precipitated calcium carbonate, ground/pulverized calcium carbonate, albacar, PCC, GCC), calcite, limestone, crushed marble, ground limestone, lime, and chalk (e.g. whiting chalk, champagne chalk, french chalk).

The present compositions may also contain ingredients, substances, elements and materials containing, hydrogen, alkyl groups, aryl groups, halo groups, hydroxy groups, alkoxy groups, alkylamino groups, dialkylamino groups, acyl groups, carboxyl groups, carboamido groups, sulfonamide groups, aminoacyl groups, amide groups, amine groups, nitro groups, organo selenium compounds, hydrocarbons, and cyclic hydrocarbons.

The present compositions may be combined with substances such as benzol peroxide, vasoconstrictors, vasodilatators, salicylic acid, retinoic acid, azelaic acid, lactic acid, glycolic acid, pyreuric acid, tannins, benzlidenecamphor and derivatives thereof, alpha hydroxyis, surfactants.

Compositions of some embodiments of the present invention may be bioconjugated to polyethylenglycol (e.g. PEG, SE-PEG) which preserves the stability (e.g., against protease activities) and/or solubility (e.g., within a biological fluid such as blood, digestive fluid) of the active ingredients while preserving their biological activity and prolonging their half-life.

The compositions of the present invention can be formulated as putty, ointment, inhalants, woven/non-woven pads, bandages, sponge, gels or hydrogels, (formulated with for example, gellatine, hyaluronic acid) or on the basis of poly-acrylate or an oleogel (e.g. made of water and Eucerin).

Oleogels comprising both an aqueous and a fatty phase are based particularly on Eucerinum anhydricum, a basis of wool wax alcohols and paraffin, wherein the percentage of water and the basis can vary. Furthermore additional lipophilic components for influencing the consistency can be added, e.g. glycerin, polyethylene glycols of different chain lengths, e.g. PEG400, plant oils such as almond oil, liquid paraffin, neutral oil and the like. The hydrogels of the present invention can be produced through the use of gel-forming agents and water, wherein the first are selected especially from natural products such as cellulose derivatives, such as cellulose ester and ether, e.g. hydroxyethyl-hydroxypropyl derivatives, e.g. tylose, or also from synthetic products such as polyacrylic acid derivatives, such as Carbopol or Carbomer, e.g. P934, P940, P941. They can be produced or polymerized based on known regulations, from alcoholic suspensions by adding bases for gel formation.

Exemplary amounts of procollagen in the gel include 0.01-30 g per 100 g of gel, 0.01-10 g per 100 g of gel, 0.01-8 g per 100 g of gel, 0.1-5 g per 100 g of gel.

In addition, the pharmaceutical compositions of this aspect of the present invention also include a dermatologically acceptable carrier.

The phrase "dermatologically acceptable carrier", refers to a carrier which is suitable for topical application onto the skin, i.e., keratinous tissue, has good aesthetic properties, is compatible with the active agents of the present invention and any other components, and is safe and non-toxic for use in mammals.

In order to enhance the percutaneous absorption of the active, one or more of a number of agents can be added to the pharmaceutical compositions including, but not limited to, dimethylsulfoxide, dimethylacetamide, dimethylformamide, surfactants, azone, alcohol, acetone, propylene glycol and polyethylene glycol.

The carrier utilized in the compositions of the invention can be in a wide variety of forms. These include emulsion carriers, including, but not limited to, oil-in-water, water-in-oil, water-in-oil-in-water, and oil-in-water-in-silicone emulsions, a cream, an ointment, an aqueous solution, a lotion, a soap, a paste, an emulsion, a gel, a spray, a foam or an aerosol. As will be understood by the skilled artisan, a given component will distribute primarily into either the water or oil/silicone phase, depending on the water solubility/dispersibility of the component in the composition.

Emulsions according to the present invention generally contain a pharmaceutically effective amount of the agent disclosed herein and a lipid or oil. Lipids and oils may be derived from animals, plants, or petroleum and may be natural or synthetic (i.e., man-made). Examples of suitable emulsifiers are described in, for example, U.S. Pat. No. 3,755,560, issued to Dickert, et al. Aug. 28, 1973; U.S. Pat. No. 4,421,769, issued to Dixon, et al., Dec. 20, 1983; and McCutcheon's Detergents and Emulsifiers, North American Edition, pages 317-324 (1986), each of which is fully incorporated by reference in its entirety.

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form.

Examples of suitable carriers comprising oil-in-water emulsions are described in U.S. Pat. No. 5,073,371 to Turner, D. J. et al., issued Dec. 17, 1991, and U.S. Pat. No. 5,073,372, to Turner, D. J. et al., issued Dec. 17, 1991 each of which is fully incorporated by reference in its entirety. An especially preferred oil-in-water emulsion, containing a structuring agent, hydrophilic surfactant and water, is described in detail hereinafter.

A preferred oil-in-water emulsion comprises a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant.

A wide variety of anionic surfactants are also useful herein. See, e.g., U.S. Pat. No. 3,929,678, to Laughlin et al., issued Dec. 30, 1975 which is fully incorporated by reference in its entirety. In addition, amphoteric and zwitterionic surfactants are also useful herein.

The pharmaceutical compositions of the present invention can be formulated in any of a variety of forms utilized by the pharmaceutical or cosmetic industry for skin application including solutions, lotions, sprays, creams, ointments, salves, gels, oils, wash, etc., as described below.

The pharmaceutical or cosmetic compositions of the present invention may be formulated to be sufficiently viscous so as to remain on the treated skin area, does not readily evaporate, and/or is not easily removed by rinsing with water, but rather is removable with the aid of soaps, cleansers and/or shampoos.

Methods for preparing compositions having such properties are well known to those skilled in the art, and are described in detail in Remington's Pharmaceutical Sciences, 1990 (supra); and Pharmaceutical Dosage Forms and Drug Delivery Systems, 6th ed., Williams & Wilkins (1995).

The topical compositions of the subject invention, including but not limited to lotions and creams, may comprise a dermatologically acceptable emollient. As used herein, "emollient" refers to a material useful for the prevention or relief of dryness, as well as for the protection of the skin. Wide varieties of suitable emollients are known and may be used herein. See, e.g., Sagarin, Cosmetics, Science and Technology, 2nd Edition, Vol. 1, pp. 3243 (1972), which contains numerous examples of materials suitable as an emollient and is fully incorporated herein by reference. A preferred emollient is glycerin.

Lotions and creams according to the present invention generally comprise a solution carrier system and one or more emollients.

The topically applied pharmaceutical or cosmetic composition of the present invention may also include additional components which are added, for example, in order to enrich the pharmaceutical or cosmetic compositions with fragrance and skin nutrition factors.

Such components are selected suitable for use on human keratinous tissue without inducing toxicity, incompatibility, instability, allergic response, and the like within the scope of sound medical judgment. In addition, such optional components are useful provided that they do not unacceptably alter the benefits of the active compounds of the invention.

The CTFA Cosmetic Ingredient Handbook, Second Edition (1992) describes a wide variety of non-limiting cosmetic ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin-conditioning agents (e.g., humectants, including miscellaneous and occlusive), skin soothing and/or healing agents (e.g., panthenol and derivatives e.g., ethyl panthenol), aloe vera, pantothenic acid and its derivatives, allantoin, bisabolol, and dipotassium glycyffhizinate, skin treating agents, thickeners, and vitamins and derivatives thereof.

It will be appreciated that the procollagen of the present invention may be incorporated into products already developed or being developed by cosmetic companies, including but not limited to Estee Lauder, Helena Rubinstein and L'Oreal.

The pharmaceutical or cosmetic compositions of the present invention can be applied directly to the skin. Alternatively, it can be delivered via normal skin application by various transdermal drug delivery systems which are known in the art, such as transdermal patches that release the composition into the skin in a time released manner. Other drug delivery systems known in the art include pressurized aerosol bottles, iontophoresis or sonophoresis. Iontophoresis is employed to increase skin permeability and facilitate transdermal delivery. U.S. Pat. Nos. 5,667,487 and 5,658,247 discloses an ionosonic apparatus suitable for the ultrasonic-iontophoretically-mediated transport of therapeutic agents across the skin. Alternatively, or in addition, liposomes or micelles may also be employed as a delivery vehicle.

Since wounds and ischemia may engage the scalp, the pharmaceutical compositions of the present invention further include emollients, surfactants and/or conditioners which are suitable for use on the scalp skin and hair.

The emollients include, but are not limited to, hydrocarbon oils and waxes, such as mineral oil, petrolatum, and the like, vegetable and animal oils and fats, such as olive oil, palm oil, castor oil, corn oil, soybean oil, and the like, and lanolin and its derivatives, such as lanolin, lanolin oil, lanolin wax, lanolin alcohols, and the like. Other emollients include esters of fatty acids having 10 to 20 carbon atoms, such as including myristic, stearic, isostearic, palmitic, and the like, such as methyl myristate, propyl myristate, butyl myristate, propyl stearate, propyl isostearate, propyl palmitate, and the like. Other emollients include fatty acids having 10 to 20 carbon atoms, including stearic, myristic, lauric, isostearic, palmitic, and the like. Emollients also include fatty alcohols having 10 to 20 carbon atoms, such as cetyl, myristyl, lauryl, isostearyl, stearyl and the like.

An emulsifier/surfactant is preferably utilized when formulating the pharmaceutical compositions of the present invention for use on hair.

Examples of surfactants include, but are not limited to, spolyoxyalkylene oxide condensation products of hydrophobic alkyl, alkene, or alkyl aromatic functional groups having a free reactive hydrogen available for condensation with hydrophilic alkylene oxide, polyethylene oxide, propylene oxide, butylene oxide, polyethylene oxide or polyethylene glycol. Particularly effective are the condensation products of octylphenol with ~7 to ~13 moles of ethylene oxide, sold by the Rohm & Haas Company under their trademark TRITON 100® series products.

Other ingredients such as, fragrances, stabilizing agents, dyes, antimicrobial agents, antibacterial agents, antiagglomerates, ultraviolet radiation absorbers, and the like are also included in the composition of the present invention which is formulated for use on hair.

A conditioner agent stable to acid hydrolysis, such as a silicone compound having at least one quaternary ammonium moiety along with an ethoxylated monoquat is preferably also utilized in order to stabilize and optionally thicken the composition of the present invention which is formulated for use on hair.

An optional thickener also can be included to improve composition esthetics and facilitate application of the composition to the hair. Exemplary thickeners are methylcellulose, hydroxybutyl methylcellulose, hydroxypropylcellulose, hydroxypropyl methylcellulose, hydroxyethyl ethylcellulose and hydroxyethylcellulose, di (hydrogenated tallow) phthalic acid amide, crosslinked maleic anhydride-methyl vinyl ether copolymer, guar gum, xanthan gum and gum arabic.

The carrier of the conditioning composition is predominantly water, but organic solvents also can be included in order to facilitate manufacturing of the composition or to provide esthetic properties, such as viscosity control. Suitable solvents include the lower alcohols like ethyl alcohol and isopropyl alcohol; glycol ethers, like 2-butoxyethanol, ethylene glycol monoethyl ether, propylene glycol and diethylene glycol monoethyl ether or monomethyl ether and mixtures thereof. Non-limiting conditioning agents which may be used in opaque conditioners include: stearyltrimethylammonium chloride; behenetrimethylammonium chloride; cetrimonium bromide; soytrimonium chloride; tallowtrimonium chloride; dihyrogenatedtallowedimethylammonium chloride; behentrimethylammonium methosulfate; Peg-2 Oleammonium chloride; dihyrogenatedtallowedimethylammonium bromide; dihyrogenatedtallowedimethylammonium methosulfate; palmityltrimethylammonium chloride; hydrogenated tallowtrimethylammonium chloride; hydrogenated tallowtrimethylammonium bromide; dicetyidimethylammonium chloride; distearyldimethylammonium chloride; dipalmityidimethylammonium chloride; hydrogenated tallowtrimethylammonium methosulfate; cetrimonium tosylate; eicosyltrimethylammonium chloride and ditallowedimethylammonium chloride.

Shampoo formulations are sometimes advantageous for treating scalp skin conditions (e.g. lesions, psoriasis).

The hair shampoo composition of the present invention may be provided in any form selected from liquid, powder, gel and granule as needed. A liquid composition using water or a lower alcohol as a solvent is preferred, with a liquid composition using water being especially preferred. Shampoo compositions which may be used according to the teachings of the present invention are further described in U.S. Pat. No. 6,194,363 and U.S. Pat. No. 6,007,802.

It will be appreciated that the procollagen of the present invention may be incorporated into biocompatible and/or biodegradable polymer-based matrices, including sheets, films, membranes sponges and gels.

Procollagen can be absorbed or encapsulated into biocompatible polymer-based matrices or alternatively, actively crosslinked to such constructs by exposure to ultraviolet radiation, dehydrothermal (DHT) techniques or via chemical reagents such as the zero-length 1-ethyl-3-(3-dimethylaminopropyl) carbodiimide hydrochloride (EDC) crosslinker (Cornwell K G, et al., Biomed Mater Res A. 2007 February; 80(2):362-71). Detailed protcols of how the procollagen of the present invention may be incorporated into collagen matrices are provided in Example 2, herein below.

The procollagen of the invention may be included in biodegradable acellular matrix components. An acellular matrix component generally fulfils a structural role. For example, it may fill in a defect, hole, space or cavity in tissue and provide an environment in which injected or implanted cells can adhere to the matrix or surrounding tissue and grow and produce other factors (e.g., chemotactic factors) resulting from the growth of new tissue. In many instances, the gap-filling function of the matrix is temporary and only lasts until the implanted and/or host cells migrate into the area and form new tissue. Preferably, the acellular matrix is biodegradable. The matrix is preferably a solid or semi-solid substance that is insoluble under physiological conditions. Such compositions are suitable for injection or implantation into a subject to repair tissue that has degenerated.

The term "biodegradable" as used herein refers to a composition that is not biologically harmful and can be chemically degraded or decomposed by natural effectors (e.g., weather, soil bacteria, plants, or animals). Examples of matrices that can be used in the present invention include, without limitation, acellular matrices containing autologous and non-autologous proteins, and acellular matrices containing biodegradable polymers.

The procollagen of the present invention may be incorporated into any of a number of biodegradable acellular matrices containing non-autologous proteins. Examples of biodegradable acellular matrices include matrices containing any type of collagen (e.g., bovine, porcine, human, or bio-engineered collagen), or any type of collagen with glycosaminoglycans (GAG) cross-linked with, for example, glutaraldehyde. Matrices containing collagen include, without limitation, absorbable collagen sponges, collagen membranes and bone spongiosa. Useful types of collagen include, for example, bovine collagen, porcine collagen, marine collagen, human cadaver collagen bioengineered collagen, and autologous human collagen.

Absorbable collagen sponges can be purchased from, for example, Sulzer Calcitek, Inc. (Carlsbad, Calif.). These collagen sponge dressings, sold under the names COLLATAPE™, COLLACOTE™ and COLLAPLUG™ are made from cross-linked collagen extracted from bovine deep flexor (Achilles) tendon, and GAG. These products are soft, pliable, nonfriable, and non-pyrogenic. Greater than 90% of a collagen sponge typically consists of open pores.

The biodegradable acellular matrices to which procollagen may be incorporated may contain collagen (e.g., bovine or porcine collagen type I) formed into, for example, a thin membrane. One such membrane is manufactured by Sulzer Calcitek and is marketed as BIOMEND™. Another such membranous matrix is marketed as BIO-GIDE™ by Geistlich Sohne AG (Wolhusen, Switzerland), and is made of porcine type I and type III collagen. BIO-GIDE™ has a bilayer structure, with one surface that is porous and allows the ingrowth of cells, and a second surface that is dense and prevents the ingrowth of fibrous tissue.

Other suitable matrices containing collagen to which the procollagen of the present invention may be incorporated include COLLAGRAFT™ manufactured by NeuCell, Inc. (Campbell, Calif.), and OSTEOSET™ calcium sulfate alpha hemi-hydrate pellets sold by Wright Medical Technology (Arlington, Tenn.).

Biodegradable acellular matrices to which the procollagen of the present invention may be incorporated also can be made from bone spongiosa formed into granules or blocks. This material consists of animal (e.g., human, non-human primate, bovine, sheep, pig, or goat) bone from which substantially all organic material (e.g., proteins, lipids, nucleic acids, carbohydrates, and small organic molecules such as vitamins and non-protein hormones) has been removed. This type of matrix is referred to herein as an "anorganic matrix". One such matrix, which is marketed as BIO-OSS™ spongiosa granules and BIO-OSS™ blocks, is manufactured by Geistlich Sohne AG. This company also manufactures a block-type matrix (BIO-OSS™ collagen) that contains anorganic bone and additionally contains approximately 10% collagen fibers by weight.

Demineralized bone can be combined with the procollagen of the present invention to produce a matrix in the form of a sponge, block, or membrane. An exemplary matrix made from demineralized human bone, for example, is formed into small blocks and marketed as DYNAGRAFT™ by GenSci Regeneration Laboratories, Inc. (Toronto, Ontario, Canada), TUTOPLAST™ by Tutogen Medical, Inc. (Clifton, N.J.), or GRAFTON™ Demineralized Bone Matrix by Osteotech, Inc. (Eatontown, N.J.). Other useful biodegradable acellular matrices to which the procollagen may be incorporated are those which contain gelatin, cat gut, anorganic bone, coral, glycosaminoglycans such as mucopolysaccharide or hyaluronic acid or hydroxyapatite, or mixtures of these substances.

In addition, synthetic polymers made from one or more monomers can be used to make biodegradable acellular matrices to which the procollagen of the present invention may be incorporated. Such synthetic polymers include, for example poly(glycolic acid), poly(lactic acid), and poly(glycolicacid)-poly(lactic acid). Synthetic polymers also can be combined with any of the above-mentioned substances to form matrices. Different polymers forming a single matrix can be in separate compartments or layers. For example, W. L. Gore & Associates, Inc. (Flagstaff, Ariz.) manufactures a porous biodegradable acellular matrix (GORE RESOLUT XT Regenerative Material). This matrix is composed of a synthetic bioabsorbable glycolide and trimethylene carbonate copolymer fiber into which cells can migrate, attached to an occlusive membrane that is composed of a synthetic bioabsorbable glycolide and lactide copolymer that does not permit ingrowth of cells. Other examples of suitable biodegradable matrices can be found in U.S. Pat. No. 5,885,829, for example.

It will be appreciated that the matrices to which the procollagen of the present invention is incorporated may be coated with one or more attachment molecule known in the art so as to enhance the ability of cells to attach to the biodegradable acellular matrices. These attachment molecules include natural molecules (e.g., extracellular matrix factors such as laminin and fibronectin) and synthetic molecules (e.g., peptides containing the binding sites of fibronectin and/or laminin). Example of useful agents are, without limitation, basement membrane components, gelatin, gum Arabic, collagen types I XII, fibronectin, laminin, thrombospondin, entactin, proteoglycans, glycosaminoglycans, and mixtures thereof. Other appropriate attachment molecules include simple carbohydrates, complex carbohydrates, asialoglycoproteins, lectins, growth factors, low density lipoproteins, heparin, poly-lysine, poly-ornithine, thrombin, vitronectin, and fibrinogen. Use of attachment molecules and methods for linking them to biodegradable acellular matrices are described in U.S. Pat. No. 6,095,148.

The procollagen of the invention may also be included in biodegradable acellular filler materials (i.e., bulking agents). Such compositions may be suitable for injection into a subject in order to repair tissue that has degenerated. A filler material generally fulfils a structural function. For example, it may fill in a defect, hole, space or cavity in tissue and provide an environment in which injected cells can adhere to the surrounding tissue and grow and produce other factors (e.g., chemotactic factors) resulting from the growth of new tissue. In many instances, the gap-filling function of the filler is temporary and only lasts until the implanted and/or host cells migrate into the area and form new tissue. Preferably the filler is biodegradable. Fillers are typically provided and used as a viscous solution or suspension.

According to one embodiment, the filler to which the procollagen is incorporated is a dermal filler.

As used herein, the term "dermal filler" refers to a type of tissue augmentation material which is generally used in the dermis area, such as below the epidermis or above the hypodermis, and as such may be injected subcutaneously, hypodermically or intradermally, or some combination.

Numerous types of biodegradable, acellular injectable fillers can be used together with the procollagen of the present invention. The filler can consist of autologous proteins, including any type of collagen obtained from a subject. An example of such a filler is AUTOLOGEN™, formerly produced by Collagenesis Corp. (Beverly, Mass.). AUTOLOGEN™ is a dispersion of autologous dermal collagen fibers from a subject, and therefore does not elicit even a minimal immune response when readministered to the subject. In order to obtain AUTOLOGEN™, a specimen of tissue (e.g., dermis, placenta, or umbilical cord) is obtained from a subject and forwarded to Collagenesis Corp., where it is processed into a collagen-rich dispersion. Approximately one and a half square inches of dermal tissue can yield one cubic centimeter (cc) of AUTOLOGEN™. The concentration of AUTOLOGEN™ can be adjusted depending upon the amount required to correct defects or augment tissue within the subject. The concentration of AUTOLOGEN™ in the dispersion can be, for example, at least about 25 mg/L (e.g., at least about 30 mg/L, at least about 40 mg/L, at least about 50 mg/L, or at least about 100 mg/L).

An acellular injectable filler material can also contain non-autologous proteins, including any type of collagen, such as those described herein below.

An exemplary dermal filler matrix to which the procollagen may be incorporated is that manufactured by Johnson &

Johnson (EVOLENCE™) which includes a porcine-derived collagen, as disclosed in U.S. Pat. No. 6,682,760.

Other exemplary dermal filler matrices to which the procollagen may be incorporated are those manufactured by Allergan Medical. These include the dermal fillers named ZYDERM™ (Collagen Corp., Palo Alto, Calif.) and ZYPLAST™ which are injectable formulations of bovine collagen and Cosmoderm and Cosmoplast, which are composed of human collagen. ZYDERM™ is prepared from bovine skin and is composed of reconstituted atelopeptide collagen in saline with a small amount of local anesthetic. ZYDERM™ is described in U.S. Pat. No. 3,949,073. ZYPLAST™ is a lightly crosslinked preparation of bovine collagen and is processed by cross-linking with 0.25% glutaraldehyde, followed by filtration and mechanical shearing through fine mesh. The methodologies involved in the preparation and clinical utilization of this material are disclosed in U.S. Pat. No. 4,582,640 and U.S. Pat. No. 4,642,117.

COSMODERM™ and COSMOPLAST™ are dermal fillers approved for the correction of facial wrinkles, acne scars and other soft tissue contour deficiencies, as well as for the restoration of the lip border. The collagen in COSMODERM™ and COSMOPLAST™ is purified from human dermal tissue that is grown under controlled conditions.

The present invention also conceives incorporating the procollagen of the present invention to microsphere-based dermal fillers such as ARTEFILL1™. ARTEFILL™ is a unique combination of precision filtered synthetic microspheres (20%) evenly suspended in Ultra-Purified Collagen™ (80%). After ARTEFILL™ is injected, the microscopic spheres stimulate the body's own natural collagen production to replace the purified collagen. The microsphere-based technology of this product is disclosed in U.S. Pat. No. 5,344,452.

ISOLAGEN™ is another dermal filler product to which it may be useful to incorporate the procollagen of the present invention. ISOLAGEN™ (manufactured by Isolagen Inc.) comprises cultured autologous fibroblasts. This dermal filler is disclosed in U.S. Pat. Nos. 5,591,444 and 6,432,710.

HUMALLAGEN™, manufactured by Albiorex International is a human collagen derived from the placenta for dermal fill injections to correct facial wrinkles. This dermal filler is disclosed in U.S. Pat. No. 5,002,071.

The procollagen of the present invention may also be incorporated into DERMALOGEN™ (Angiotech Pharmaceuticals). This product is an injectable collagen matrix derived from human skin after removal of the non-collagenous proteins and is used as an off-the-shelf allogeneic implant material.

The procollagen of the present invention may also be incorporated into FASCIAN™ (Fascian Biosystems). This is an injectable human implant material made from fascia.

Other examples of useful filler materials to which the procollagen of the present invention may be incorporated include, but are not limited to, solubilized gelatin, polyglycolic acid (e.g., solubilized polyglycolic acid or particles of polyglycolic acid), or cat gut sutures. A particular gelatin matrix implant, for example, is sold under the mark FIBRIL™. This filler contains equal volumes of (1) a mixture of porcine gelatin powder and o-aminocaproic acid dispersed in a 0.9% (by volume) sodium chloride solution, and (2) an aliquot of plasma from the subject. Other substances useful as fillers include hyaluron, hyaluronic acid, restalyn, and parleane.

According to another embodiment, the procollagen of the present invention can be incoporated into a matrix for use in a spinal fusion procedure. Spinal fusion procedures are indicated in the management of spinal degenerative disc disease, a common cause of low back pain.

Thus, for example the procollagen of the present invention may be incorporated into a sponge such as INFUSE™ (a sponge made from bovine Type 1 collagen), manufactured by Medtronic. For the spinal fusion procedure, the sponges are soaked in recombinant human Bone Morphogenetic Protein (rhBMP-2) and then inserted into cage devices (INTER FIX and/or INTER FIX RP Threaded Fusion Devices), prior to implantation between the vertebrae.

Another scaffold used for spinal fusion procedures to which the procollagen of the present invention may be incorporated is that named OP-1™, manufactured by Stryker. This scaffold consists of rh-BMP-7 and bovine collagen, which is reconstituted with saline to form a paste.

Other matices for spinal fusion to which the procollagen of the present invention may be incorporated are those taught in U.S. Pat. Nos. 5,645,084, 5,776,193, 5,910,315, 6,187,047, 6,425,920, 6,613,091, 7,041,309 and U.S. Pat. Application Nos. 2004/0192658, 2002/0082697 and 2005/0037978.

According to yet another embodiment, the procollagen of the present invention may be incorporated into a collagen-comprising matrix for use in bone grafts. Accordingly, the procollagen of the present invention can be incorporated into matrices disclosed in U.S. Pat. Nos. 4,789,663, 5,171,574, 5,866,113, 6,077,988, 6,166,184, 6,630,153, 7,172,629 and U.S. Pat. Appl. Nos. 2002/0082694, 2007/0254042 and 2006/0233853.

The matrix may be embedded with ceramic granules such as MASTERGRAFT™ Matrix and MASTERGRAFT™ putty, both manufactured by Medtronics, and COLLAGRAFT™ (manufactured by Angiotech Pharmaceuticals and distributed by Zimmer). This latter product essentially consists of a mixture of porous beads composed of 60% hydroxyapatite and 40% tricalcium phosphate ceramic and fibrillar collagen. Another porous scaffold contemplated for incorporation with procollagen is the Integra OS™ scaffold which is made of highly purified type-I collagen and tricalcium phosphate. A similar product is BI-OSTETIC FOAM™ manufactured by Berkeley Advanced Biomaterials. It is a sterile bone graft composed of highly purified fibrillar Type I bovine collagen and BI-OSTETICT™ resorbable 60% hydroxyapatite and 40% tricalcium phosphate granules.

The matrix may be malleable or non-malleable. U.S. Pat. Appl. 20070178130 teaches an exemplary malleable matrix to which the procollagen of the present invention may be incorporated.

Examples of malleable matrices to which the procollagen of the present invention may be incorporated for bone grafting include the MASTERGRAFT™ putty, mentioned herein above; MOZAIC™ putty, manufactured by Integra; Integra OS™ putty, manufactured by Integra, DBX™ bone putty manufactured by Synthes and GENEX™ putty, manufactured by Biocomposites and GENEX™ paste, manufactured by Biocomposites. GENEX™ is a resorbable bone graft material manufactured through a proprietary process that confers the product with a reproducible negative surface charge. Another paste contemplated by the present invention is BIOSET™ RT Allograft Paste. This is a mouldable demineralized bone matix paste mixed with uniformly sized cortical bone chips, manufactured by RTI biologics.

According to one embodiment, the collagen matrix for use in bone grafts to which the procollagen may be incorporated is in the form of flexible strips, such as MOZAIC™ strips, manufactured by Integra, HEALOS™, manufactured by Johnson and Johnson and VITOSS™ manufactured by Orthovita.

It will be appreciated that the collagen matrix for use in bone grafts may also be moulded into blocks and other shapes such as some of the VITOSS™ products manufactured by Orthovita. The VITOSS™ products are covered by U.S. Pat. No. 5,939,039.

The present invention also contemplates adding procollagen to the scaffolds of Osteotech including for example MAGNIFUSE™. MAGNIFUSE™ is a combination of allograft bone within a polymer mesh that provides targeted and contained delivery. The polymer mesh is made from a biodegradable suture material and is designed for effective cellular in-growth and complete resorption within three to six months, while not interfering with bone regeneration.

In addition, the present invention contemplates adding procollagen to the scaffolds of Pioneer Surgical such as FOR-TROSS™, which is a combination of NANOSS™ hydroxyapatite and a bone growth promotion of E-MATRIX™ scaffold and the Bioset RTI™.

According to yet another embodiment, the procollagen of the present invention may be incorporated into bone cements such as those manufactured by Biomet.

A number of collagen-based and non-collagen products are commercially available for skin replacement to which the procollagen of the present invention may be incorporated. For example, the procollagen of the present invention may be incorporated into artificial skin coverings. Artificial skin coverings can be used as a temporary covering in third degree burn patients, avoiding the risk of infectious disease associated with human cadaver allografts (HCA). Accordingly, the present invention contemplates incorporation of the procollagen of the present invention into skin products taught in U.S. Pat. Nos. 4,882,162, 5,273,900, 5,460,939, 6,040,493, 4,837,379, 5,830,507, 5,536,656, 4,060,081, 5,032,508, 5,443,950, 5,837,278, 5,256,418, 6,497,875, 5,266,480, 5,591,444, 586,398, 5,489,304, 5,660,850, 6,855,860 and International Patent No. WO/1997/006837.

One example of an artificial skin covering is TRANSCYTE™, also known as DERMAGRAFT™. This is a synthetic epidermal layer that is biocompatible and protects the wound surface from infection. It is semi-permeable, allowing fluid and gas exchange. The inner layer of TRANSCYTE™ is created by culturing human newborn foreskin-derived fibroblasts onto a silicon and nylon net. Freezing procedures destroy the fibroblasts leaving a solid product of growth factors behind, including essential human structural and provisional matrix proteins, glycosaminoglycans and growth factors known to facilitate healing. The inner layer, containing the dermal components known to promote healing of the burn, adheres quickly to the wound surface. The patient's epithelial cells proliferate and migrate across the wound resulting in rapid wound healing.

BIOBRANE™ (Smith and Nephew, Netherlands) is a biosynthetic bandaging product consisting of nylon fabric partially embedded in silicon film. Collagen is chemically bound to the complex three-dimensional structure of the tri-filament thread. Blood or sera clots in the nylon matrix, which adheres the dressing to the wound until epithelialization occurs or until autografting is possible.

INTEGRA™ (Integra Artificial Skin Dermal Regeneration Template; Integra LifeSciences Corp, New Jersey, USA) is a two-layer membrane consisting of a synthetic polysiloxane epidermal layer and a dermal layer consisting of a porous lattice of cross-linked collagen fibres. The dermal layer is a biodegradable template where blood and lymph vessels, fibroblasts and other cells migrate into the lattice from surrounding healthy tissue. The fibroblasts degrade the template and recreate a collagen matrix. Seven to fourteen days after the artificial skin has been applied, the synthetic epidermal layer is removed and skin can be grafted over the wound.

ALLODERM™ manufactured by BioHorizons is a non-living, immunologically inert allogeneic acellular dermal matrix with an intact basement membrane complex. It prepares the wound bed for grafting, allowing improved cultured allograft 'take' and provides an intact basement membrane.

Another living skin equivalent, composite cultured skin (ORCEL™, Ortec), consists of allogeneic fibroblasts and keratinocytes seeded on opposite sides of bilayered matrix of bovine collagen.

The present invention also contemplates incoroporation of the procollagen of the present invention into dressing material derived from pigs: porcine small intestinal submucosa acellular collagen matrix (OASIS™) and an acellular xenogeneic collagen matrix (E-Z-DERM™).

Tissue Sciences (Covington, Ga.) markets a product known as PERMACOL™, which is comprised of cross-linked porcine dermis. DePuy (Warsaw, Ind.) markets the RESTORE PATCH™ which is fabricated from porcine small intestine submucosa. Biomet (Warsaw, Ind.) markets a product known as CUFFPATCH™ another porcine small intestine product. The CUFFPATCH™ and the RESTORE PATCH™ products provide biocompatible scaffolds for wound repair and may also be incorporated with the procollagen of the present invention. Fabrication of such patches from porcine small intestine submucosa is described in U.S. Pat. No. 4,902,508 Badylak et al. and U.S. Pat. No. 5,573,784 Badylak et al.

To repair large tears of the skin or chronic skin wounds (e.g. the feet of diabetics), it is desirable to use a scaffold or graft material to help support the damaged tissue and guide its repair.

Accordingly, the present invention envisages incorporation of the procollagen of the present invention into scaffolds such as those taught in U.S. Pat. Nos. 5,336,616; 5,024,830; 4,865, 871.

Several types of materials have been used for such procedures. Wright Medical (Memphis, Tenn.) markets a product known as GRAFTJACKET™, which is manufactured by Lifecell Corporation (Branchburg, N.J.) from human cadaver skin. The skin undergoes a process that removes the epidermis and dermal cells. This process allows the body to accept the matrix and reduces the rejection response. The processing steps that yield the GRAFTJACKET™ Matrix sufficiently preserve the human dermal tissue, including its native protein, collagen structure, blood vessel channels and essential biochemical composition, to allow cellular repopulation and revascularization through the body's natural healing process.

After implantation, the body's natural repair process revascularizes and repopulates the GRAFTJACKET™ Matrix with cells and allows the body to convert the GRAFT-JACKET™ Matrix into living tissue, e.g., skin. This means that the body can use GRAFTJACKET® Matrix as it repairs itself. Accordingly, the present invention envisages incorporating the procollagen of the present invention into the GRAFTJACKET™ scaffold.

Another matrix for treatment of deep wounds to which the procollagen of the present invention may be incorporated is the INTEGRA Flowable Wound Matrix™ produced by Integra Lifesciences, which is an advanced wound care matrix comprised of a granulated cross-linked bovine tendon collagen and glycosaminoglycan. The granulated collagen-glycosaminoglycan is hydrated with saline and applied in difficult to access wound sites and tunneled wounds. It provides a scaffold for cellular invasion and capillary growth.

The present invention also contemplates incorporating the procollagen of the present invention into collagen-comprising hemostasis sealant products such as those disclosed in U.S. Pat. Nos. 4,016,877, 4,578,067, 4,606,910, 5,951,583, 6,096,309, 6,596,304 and U.S. Patent Application Nos. 2004/0076647.

VITAGEL™ Surgical Hemostat, produced by Orthovita is a sprayable liquid hemostatic product composed of bovine thrombin and bovine collagen that is mixed with autologous blood-derived plasma. Vitagel works by combining the thrombin/collagen suspension with the patient's own plasma to form a fibrin/collagen clot. Joined syringes, one holding plasma (human) from the patient, and the other an aqueous mixture of bovine thrombin and collagen, mix these components for spraying onto bleeding wounds.

AVITENE Ultrafoam™ collagen sponge, produced by Bard, is another collagen hemostat indicated to stop bleeding during surgical procedures by accelerating blood clot formation.

INSTAT™ Collagen Absorbable Hemostat, from Johnson & Johnson is another exemplary hemostat that may be incorporated with the procollagen of the present invention. It is available in pad as well as in powder form. INSTAT™ Collagen Absorbable Hemostat is made of a purified and lyophilized bovine dermal collagen. The material, when prepared as a sponge-like pad, is lightly cross-linked, sterile, non-pyrogenic, and absorbable.

Urethral bulking to treat urinary incontinence involves injecting material around the urethra. This may be done to close a hole in the urethra through which urine leaks out or to build up the thickness of the wall of the urethra so it seals tightly when you hold back urine. Most bulking materials are injected around the urethra just outside the muscle of the urethra at the bladder outlet. Injecting the bulking material may be done through the skin, through the urethra or, in women, through the vagina. Needle placement is guided by the use of a cystoscope inserted into the urethra. Materials used for urethral bulking typically include polytetrafluoroethylene (PTFE), bovine collagen (glutaraldehyde cross-linked bovine collagen) and durasphere. Accordingly, the present invention contemplates incorporating the procollagen of the present invention into the collagen matrix used for urethral bulking.

Thus, the procollagen of the present invention may be incorporated into the collagen implant named Contigen-Bard™ manufactured by Bard or the implants disclosed in U.S. Pat. Nos. 4,773,393, 5,385,561, 5,989,180 and 6328687.

Large open wounds offer a point of entry for Hospital Acquired Infection (HAI). Wounds become infected not only as a result of medical procedures but also from circulating hospital air and from skin microbes. The wounds need to be kept clean and free from bacterial contamination, or the bacterial population within a wound should be reduced by application of appropriate antiseptics. Various types of dressings attempt to address the needs of bioburden reduction. They include dry dressings, moist dressings, alginate dressings, hydrocolloid and hydrogel dressings as well as collagen-based dressings and gauze dressings. Such dressings may be incorporated with the procollagen of the present invention.

Exemplary collagen comprising wound dressings that may be incorporated with the procollagen of the present invention include those disclosed in U.S. Pat. Nos. 4,950,699, 5,196,185, 5,676,967, 5,735,812, 5,836,970, 5,888,987, 6,087,549, 7,041,868 and U.S. Pat. Applications 20040001878, 20050260251, 20060188486, 20070250177, 20070255192, 20070154530 and 20080213344.

Thus, for instance, the procollagen of the present invention can be incorporated into the wound dressings of Integra, including HELISTAT™ and HELITENE™. to HELISTAT™ is made from an absorbable collagen hemostatic sponge whereas HELITENE™ is made from a fibrillar form of absorbable collagen. In both products the collagen is processed from bovine deep flexor tendon.

INTEGRA Bilayer Matrix Wound Dressing™ is an advanced wound care device comprised of a porous matrix of cross-linked bovine tendon collagen and glycosaminoglycan and a semi-permeable polysiloxane (silicone) layer. The semi-permeable silicone membrane controls water vapor loss, provides a flexible adherent covering for the wound surface and adds increased tear strength to the device. The collagen-glycosaminoglycan biodegradable matrix provides a scaffold for cellular invasion and capillary growth.

Johnson and Johnson produce a number of wound dressings, all of which are contemplated for the present invention. Exemplary wound dressings include NU-GEL™, FIBRACOLL PLUS™, Instat™ and PROMOGRAN MATRIX™.

NU-GEL™ is a sterile hydrogel formulation of preserved polyvinyl pyrrolidone in water. The gel is supported by a fusible fiber fabric scrim and protected on both sides by polyethylene film. NU-GEL™ dressing promotes natural autolysis by rehydrating and softening necrotic tissue while providing a moist wound environment. It protects against dehydration, bacterial contamination and absorbs exudates from the wound.

It will be appreciated that the wound dressing may be comprised of a composite material such as cellulose and collagen or alginate and collagen.

PROMOGRAN MATRIX™ is an exemplary dressing that combines oxidized regenerated cellulose and collagen.

FIBRACOLL PLUS™ is a dressing made up of 90% collagen and 10% alginate. This combination maintains a moist wound environment which is conducive to granulation tissue formation and epithelialization that enables healing to proceed optimally.

Organogenesis also produces a variety of wound dressings which are contemplated for incorporation by the present invention.

Thus, for example the present invention contemplates incorporation of procollagen into FORTADERM™. This wound dressing consists of a single-layer of fenestrated sheet of porcine intestinal collagen.

ColActive™ and ColActive Ag™ are collagen-based wound dressings produced by Covalon Technologies. ColActive™ is produced from USP grade denatured porcine collagen. ColActive™ can also be impregnated with silver salts to create an antiseptic collagen-based wound dressing—ColActive Ag™.

BioCore Medical Technologies produces wound dressings such as MEDIFIL™, SKINTEMP™ and COLLATEK™. MEDIFIL™ particles comprise bovine type I collagen and are for draining, undermined, tunneled, infected or contaminated deep cavity wounds. MEDIFIL™ pads are for deep cavity draining wounds. SKINTEMP™ is comprised of porous collagen sheets attached to a nonadherent backing and is indicated for dry, superficial draining wounds. COLLATEK™ comprises type I bovine collagen.

Southwest Technologies produces a product named STIMULEN™ which is a sterile primary single-use dressing comprised of a soluble modified bovine collagen base. The STIMULEN™ collagen is soluble in the wound fluid and supplied as a powder or gel or sheet.

Healthpoint offers a sterile wound covering named OASIS™ to support tissue regeneration in partial thickness wounds. It provides a tissue-engineered collagen matrix derived from porcine small intestine submucosa (SIS). OASIS™ has a one-year shelf life and is available in single thickness, fenestrated sheets.

PURACOL™, produced by Medline is yet another collagen-based wound dressing to which the procollagen of the present invention may be incorporated. This product comprises 100% pure bovine-derived collagen in it's native, triple-helix form.

TENOGLIDE™ Tendon Protector Sheet from Integra is an absorbable implant (device) that provides a non-constricting, protective encasement for injured tendons. Such a product is also envisaged to be incorporated with the procollagen of the present invention. TENOGLIDE™ is comprised of a porous matrix of cross-linked bovine Type I collagen and glycosaminoglycan (GAG). TenoGlide Tendon Protector is designed to serve as an interface between the tendon and the surrounding tissues. TenoGlide Tendon Protector is an easy to handle, conformable, porous collagen-GAG sheet designed for easy placement under, around or over an injured tendon.

GRAFTJACKET™ regenerative tissue matrix may also be used to protect tendons. This product has been described herein above.

Surgical closure of the dura, or duraplasty, is an essential part of any open neurosurgical procedure. Traumatic injuries to the head and spine often result in dural tears and lacerations that require surgical repair. The dura is a tough fibrous connective tissue sheet that forms the outer protective membrane encasing the brain and spinal cord. The dura is the first tissue of the brain encountered in any neurosurgical procedure. The neurosurgeon has to cut through the dura to allow access to the brain. At the end of a neurosurgical procedure a "water tight" repair of the dura must be achieved to prevent loss of the supporting cerebrospinal fluid (CSF) from the tissues of the brain and spinal cord. Accordingly, the present invention contemplates incorporating the procollagen of the present invention into the matrices used for duraplasty.

Such collagen-based matrices for duraplasty are disclosed in U.S. Pat. Application No. US 20070161109 and 20030204270. An exemplary product that may be incorporated with the procollagen of the present invention is DURAGEN™ by Integra Lifesciences which comprises a Type I collagen matrix.

As a result of the high incidence of neurological injuries, nerve regeneration and repair, a subfield of neural tissue engineering, is a rapidly growing field dedicated to the discovery of new ways to recover nerve functionality after injury. The present invention envisages incorporation of the procollagen of the present invention into collagen-based matrices designed to aid in the regeneration of nerves.

Nerve wraps are disclosed in U.S. Pat. Application Nos. 2004/0048796, and 2003/0072749.

Collagen Matrix Inc. produces a nerve wrap named Collagen Nerve Wrap™, which is a resorbable collagen matrix that provides a non-constricting encasement for injured peripheral nerves for protection of the neural environment, and is designed to be an interface between the nerve and the surrounding tissue.

NeuraWrap™ produced by Integra is another nerve protector, which is an absorbable collagen implant that provides a non-constricting encasement for injured peripheral nerves for protection of the neural environment. The wall of the conduit has a longitudinal slit that allows NeuraWrap™ to be spread open for easy placement over the injured nerve. The resilience of the collagen conduit allows NeuraWrap to recover and maintain closure once the device is placed around the nerve.

It is expected that during the life of a patent maturing from this application many relevant compositions, matrices and carriers will be developed and the scope of the terms provided herein is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", an and the include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1, 2, 317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Expression of Procollagen in Tobacco Plants

Constructs—All of the coding sequences were optimized for expression in the tobacco plant. FIGS. 1A-D shows the synthetic genes coding for Col1 (human collagen type I α1 chain, accession number P02452, ER signal deleted; FIG. 1A), Col2 (human collagen type I $\alpha_2$ chain, accession number P08123, ER signal deleted; FIG. 1B), P4Hα (human prolyl 4-hydroxylase alpha subunit, accession number P13674, ER signal deleted; FIG. 1C), P4Hβ (human prolyl 4-hydroxylase beta subunit, accession number P07237, ER signal and C' terminal KDEL signal deleted) and LH3 (human lysyl hydroxylase isoform 3, accession number 060568, ER signal deleted; FIG. 1D). All the genes were N' terminally fused to a vacuolar transit signal MAHARVLLLALAV-LATAAVAVASSSSFADSNPIRPVTDRAASTLA (SEQ ID NO: 14). This sequence originates from the targeting signal within the sequence encoding a plant vacuolar thiol protease (accession number P05167, GI:113603). Vacuolar-signal-fused collagen type I α1 chain and collagen type I $\alpha_2$ chain were cloned in expression cassettes composed of a Chrysanthemum rbcS1 promoter and 5' UTR together with a Chrysanthemum rbcS1 3'UTR and terminator (Outchkourov et al., 2003). The complete expression cassettes were cloned in a multiple cloning site of the pBINPLUS plant transformation vector (van Engelen et al., 1995, Transgenic Res. 4: 288-290). The synthetic genes coding for human P4Hβ and human P4Hα fused to the vacuole-targeting signal were cloned in expression cassettes composed of the CaMV 35S promoter, TMV omega sequence and Agrobacterium Nopaline synthetase (NOS) terminator carried by the vector pJD330 (Galin et al., 1987, Nucleic Acids Res 15: 3257-3273). The complete expression cassettes were cloned in a multiple cloning site of the pBINPLUS. The synthetic gene coding for LH3 with flanking Strawberry vein banding virus (SVBV) promoter (NCBI accession AF331666 REGION: 623.950 version AF331666.1 GI: 13345788) and terminated by the Agrobacterium octopin synthase (OCS) terminator (NCBI accession Z37515 REGION: 1344.1538 version Z37515.1 GI: 886843) fused to the vacuole-targeting signal was cloned in a multiple cloning site of the pBINPLUS vector carrying the P4Hβ expression cassettes.

Transformations—All four expression constructs were transformed to Agrobacterium tumefaciens (EHA 105) by electroporation. Col1- and Col2-containing Agrobacterium were used to coinoculate a Samsun NN Nicotiana tabacum plant strain, thereby creating a Col1/Col2 parent line. In parallel, Agrobacterium containing P4Hα and P4Hβ+LH3 expression cassettes were used to coinoculate a separate line of the Samsun NN tobacco plant strain, thereby generating a P4Hα/P4Hβ+LH3 parent line. PCR and western blot analyses were used to validate gene insertion and protein expression in the two parent lines. The parent plants were then crossed by positioning the anthers of Col1/Col2 on the stigma of P4Hα/P4Hβ+LH3 flowers following removal anthers of the latter plants. The progenitors of this breeding process were screened by PCR-based validation of genome-integrated genes using gene-specific primers. In addition, Southern blot analyses of the parent plants and a progenitor plant containing all genes were performed to define copy number of each gene (See Table 1 below). LH3 copy number was assumed to be identical to that of P4Hβ, as they were expressed under a single promoter. Lastly, western blot analyses were carried out to verify and quantify protein expression.

TABLE 1

Southern blot analysis of parental lines 2-372, 20-279 and the breeding progenitor plants A3-29 and C2-15

|      | A3-29        | C2-15        | 2-372        | 20-279       |
|------|--------------|--------------|--------------|--------------|
| P4Hα | 2 insertions | 3 insertions |              | 3 insertions |
| P4Hβ | 2 insertions | 2 insertions |              | 2 insertions |
| COL1 | 3 insertions | 3 insertions | 3 insertions |              |
| COL2 | 2 insertions | 2 insertions | 2 insertions |              |

Western Blots—Plants were screened for Col1 and Col2 expression using AB745 (rabbit polyclonal, anti-human placenta type I Collagen, Millipore) and goat anti-rabbit alkaline phosphatase (polyclonal, AP132A, Millipore) as primary and secondary antibodies, respectively. Plants were screened for P4Hα expression using an anti-human P4Hα antibody (#63-163 from ICN Biomedicals Inc.) and for P4Hβ expression with anti-human P4Hβ antibody (#MAB2701 from Millipore). Alkaline phosphatase-conjugated goat anti-mouse antibodies (#A3688 from Sigma) were used as secondary antibodies for both P4Hα and P4Hβ detection.

Plantlets were produced by tissue culture or by cuttings from the parent line. The plants were grown in a controlled environment in a greenhouse.

Extraction and purification of procollagen from transgenic plants—Grinding of transgenic tobacco leaves was performed with an inline IKA Labor Pilot homogenizer. Briefly, 4 L of cold extraction buffer were placed in the homogenizer reservoir which was then operated at about 8000 rpm for approximately 1 minute. Crushed leaves (1 kg) were added to the reservoir. Homogenizer speed was then increased to 13789 rpm for about 2 minutes and then reduced to about 8000 rpm. The lower valve was opened to remove the solution from the reservoir. The extract was centrifuged at 3800 g, at 5° C., for 20 minutes. Finally, the supernatant was filtered through 4 layers of cotton gauze (Sample A, FIGS. 2A-B).

For further concentration, 6.68 g charcoal and 16.67 g of polyvinylpyrrolidone (PVPP) were added to the extract while stirring for 20 minutes (5° C., 50% scraper speed or alternatively, stirred with an overhead stirrer set at 1200 rpm (5° C., 20 minutes). The solution was then saturated to 15% ammonium sulfate (AMS) (w/v) with stirring for 1 hour at 5° C. This was followed by centrifugation at 6880 rpm-8000 g (5° C., 20 minutes) or alternatively, centrifugation with a Cepa Z41 centrifuge at 26000 rpm (4° C., 20 L/h). The supernatant (Sample B, FIGS. 2A-B) was then further saturated to 25% AMS (w/v) and stirred for 1 hour (5° C.). The solution was then recentrifuged at 6880 rpm, 5° C., 30 minutes) or alternatively, centrifuged (26000 rpm, 20 L/h, 4° C.) with a Cepa Z41 centrifuge (Sample C, FIGS. 2A-B).

All subsequent steps were done in an ice-cold environment with pre-cooled solutions. The pellet thus formed was resuspended in buffer (100 mM sodium phosphate pH 7.65) at a ratio of 20 ml buffer per gr AMS-saturated pellet. The resuspended pellets were centrifuged (13000 rpm, 10 minutes, 5° C.) and the procollagen-containing supernatants were collected and filtered through a 12 layer gauze to eliminate large particle debris. Thereafter, the gauze-filtered supernatant was diluted five fold with 25 mM sodium phosphate (pH 7.65) and loaded onto an anion exchange column (XK 26/20 GE Healthcare) containing 20 ml of CaptoQ resin (GE Healthcare), and later eluted with an NaCl gradient (20 column volumes, 0-50% NaCl, flow rate 20 ml/min). Procollagen eluted primarily in the 170-250 mM NaCl fractions. The eluted procollagen-containing fractions (FIGS. 3A-B, fractions 14-20) were pooled and then further purified via one of the two techniques described below. The pooled anion exchange fractions were concentrated with a 100 kDa cut-off centricone (Vivaspin, Vivascience). The concentrate was loaded thereafter onto a Supredex 200 GL 10/300 gel filtration column (GE healthcare). Procollagen was eluted between 8.4-9.6 ml (FIGS. 4-6A-B), while the remaining proteins eluted later (FIG. 4). In this manner the intact procollagen was isolated with a high degree of purity as is evident from FIGS. 7A-B. Alternatively, the pooled anion exchange fractions were precipitated with 25% ammonium sulfate and centrifuged (8000 g, 30 minutes, 5° C.). The pellet was resuspended in 100 mM sodium phosphate (pH 7.65) to ⅟₁₅ of the volume of the precentrifugation pooled fraction volume. This solution was then diluted 10 times with 100% precooled ethanol and incubated (−20° C., 3 hours). Following centrifugation (14000 g, 30 minutes 5° C.), the pellet was resuspended in 100 mM sodium phosphate (pH 7.65) to ⅟₁₅ the volume of the precentrifugation pooled fraction volume, dialyzed against the same buffer, centrifuged (20200 g, 10 minutes, 5° C.) and filtered through a 0.2 μm filter (FIG. 8).

Results

Expression of procollagen is demonstrated in CP A3-29 plant lines (lot #CP C-18) by the presence of two prominent bands at molecular weights >170 kDa and approximately 150 kDa, as detected with anti-human placenta type I collagen antibodies (arrows in FIGS. 2A-B). Similar bands were evident in the crude extract (FIG. 2, lanes A) and supernatant post-centrifugation in 15% AMS (FIG. 2, lanes B), but were not detected in supernatants post-centrifugation in 25% AMS (FIG. 2, lanes C). Procollagen enrichment was clearly achieved in precipitates of the 25% AMS treatment (FIG. 2, lanes D), as further confirmed by SDS PAGE Instant Blue staining. Increased corresponding band intensity was demonstrated, as well as a reduction of the noncollagen, native tobacco-related bands especially those with molecular weights below 105 kDa. Thus, this added AMS-based precipitation step enriches procollagen sample purity.

Anion exchange chromatography showed that the bulk of procollagen eluted in fractions 14-24 (FIGS. 3A-B), equivalent to 170-250 mM NaCl, as measured by sample conductivity. The procollagen-containing fractions were pooled and concentrated in a 100 kDa cut-off centricone (Vivaspin, Vivascience) and loaded onto a gel filtration column. The gel filtration chromatogram (FIG. 4) showed a resolution-defined peak eluting between 7.5-9.1 ml, before elution of the remainder of the proteins (elution peaks: 10-18 ml). Silver staining (FIGS. 5A-B) and Western blot analyses (FIG. 6A-B) demonstrated significant procollagen elution in fractions 3 and 4. The <1 ml discrepancy in definition of the elution volume at which the procollagen peaked, as determined by the absorbance curves vs. gel analysis, is a standard result of the tubing volume between the detector and collecting tube. Fractions 3 and 4 were then concentrated 10-fold in a 30 kDa cut-off centricone (Vivaspin, Vivascience) and analyzed by SDS-PAGE, which clearly confirmed procollagen isolation at a high degree of purity (FIGS. 7A-B).

FIG. 8 illustrates an AMS-based precipitation of anion exchange eluate-pooled fractions as an alternative method of procollagen purification, as described in detail above. The ethanol precipitation step in this protocol enables the removal of green pigmentation from the sample. The resulting protein is stable and soluble following incubation in 4° C., freeze and thaw cycles and lyophilization, as determined by SDS PAGE analysis (FIG. 8).

Example 2

Incorporation of Procollagen into Collagen-Based Matrices

Collagen is often the material of choice to act as a depot for the release of therapeutically active compounds such as bone morphogenic proteins, growth factors, antibiotics etc. [Meaney Murray M., Rice K., Wright R J, Spector M. The effect of selected growth factors on human anterior cruciate ligament cell interactions with a three-dimensional collagen-GAG scaffold. J Orthop Res (2003) 21(2):238-44, Qian Y., Yao G., Lin Z., Chen J., Fan Y., Davey T., Xu J., Zheng M. (2009) Natural bone collagen scaffold combined with OP-1 for bone formation induction in vivo. J Biomed Mater Res B Appl Biomater Epub., Adhirajan N., Shanmugasundaram N., Shanmuganathan S., Babu M. Eur J Pharm Sci (2009) 36(2-3):235-45. Functionally modified gelatin microspheres impregnated collagen scaffold as novel wound dressing to attenuate the proteases and bacterial growth]. Collagen may be formed into sheets, films, membranes, sponges and gels, all of which can be used to release the active compound at the wound site to broaden its therapeutic application capacities and its pharmokinetic release profiles.

Procollagen can be passively absorbed into collagen matrices or alternatively, actively crosslinked to such constructs by exposure to ultraviolet radiation, dehydrothermal (DHT) techniques or via chemical reagents such as the zero-length 1-ethyl-3-(3-dimethylaminopropyl) carbodiimide hydrochloride (EDC) crosslinker (Cornwell K G, Lei P, Andreadis S T, Pins G D. J Crosslinking of discrete self-assembled collagen threads: Effects on mechanical strength and cell-matrix interactions. Biomed Mater Res A. 2007 February; 80(2):362-71).

The present example describes three protocols that may be used to incorporate procollagen into a collagen matrix.

Protocol No. 1

Soluble recombinant or animal-derived collagen suspended in 10 mM HCl is assembled to fibrils by mixing it (9:1 v/v) with 200 mM $Na_2HPO_4$, pH 11.2, followed by incubation (4-16 hr, 25-37° C.). The formed hydrogel is concentrated to 10-20 mg/ml by centrifugation and cast into an aluminum mold. The mold is incubated (2 hr, −30° C.) and transferred to −80° C. for an additional 30 minutes, followed by a 24 hour lyophilization step. The collagen matrix is then immersed (2-6 hr, 28° C.) in a crosslinking solution containing 10-50 mM EDC prepared in 90% ethanol. Unbound EDC is washed away three times with DDW. Access to single-bound EDC molecules is quenched with a 10 mM aspartic acid solution. Following extensive washings, the sample is incubated (2 hr, −30° C.) and then transferred to −80° C. for an additional 30 minutes, followed by a 24 hour lyophilization step. The collagen matrix is sterilized by ethylene oxide (ETO) or gamma irradiation. Half an hour prior to matrix implantation, the matrix is immersed in a recombinant procollagen solution to allow for its absorption into the matrix. The procollagen-enriched matrix is then affixed to the wound site.

Protocol No. 2

A fibrillar matrix is assembled by mixing soluble recombinant or animal-derived collagen suspended in 10 mM HCl with recombinant procollagen at ratios (w/w) ranging from 95:5 to 80:20 and incubation (4-16 hrs, 25-37° C., pH 7.4). The formed hydrogel is concentrated to 10-20 mg/ml by centrifugation and cast into an aluminum mold. The mold is incubated (2 hrs, −30° C.) and transferred to −80° C. for an additional 30 minutes, followed by a 24 hour lyophilization step. The procollagen-containing collagen matrix is then immersed in a crosslinking solution containing 10-50 mM EDC prepared in 90% ethanol (2-6 hrs, 28° C.). Unbound EDC is washed away three times with DDW. Access of single-bound EDC molecules are quenched with a 10 mM aspartic acid solution. Following extensive washing, the sample is incubated (2 hrs, −30° C.) and transferred to −80° C. for an additional 30 minutes, followed by a 24 hour lyophilization step. The resultant procollagen-collagen hybrid matrix is sterilized by ETO or gamma irradiation.

Protocol No. 3

Soluble recombinant or animal-derived collagen suspended in 10 mM HCl is assembled to fibrils by mixing it (9:1, v/v) with 200 mM $Na_2HPO_4$ pH 11.2, followed by incubation (4-16 hours, 25-37° C.). The formed hydrogel is concentrated to 10-20 mg/ml by centrifugation and cast into an aluminum mold. The mold is incubated (2 hrs, −30° C.), and then transferred to −80° C. for an additional 30 minutes followed by a 24 hour lyophilization step. The powdered matrix is then immersed in a recombinant procollagen-containing solution to allow for its absorption into the matrix, which is then allowed to dry at room temperature. The procollagen-collagen matrix is then immersed in a crosslinking solution of 10-50 mM EDC prepared in 90% ethanol (2-6 hours, 28° C.). Unbound EDC is washed away three times with DDW. Excess of single-bound EDC molecules are quenched with a 10 mM aspartic acid solution. Following extensive washings, the sample is incubated (2 hours, −30° C.) and transferred to −80° C. for an additional 30 minutes, followed by a 24 hour lyophilization step. The procollagen-collagen hybrid matrix is then sterilized by ETO or gamma irradiation.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of promoting wound healing, treating fibrosis and/or promoting angiogenesis comprising administering to a subject in need thereof a therapeutically effective amount of a human type I procollagen wherein the α1 chain of said procollagen comprises the collagen N propeptide having the sequence of the N propeptide of collagen type I α1 chain as set forth in SEQ ID NO: 15 and wherein the α2 chain of said procollagen comprises the collagen N propeptide having the sequence of the N propeptide of collagen type I α2 chain as set forth in SEQ ID NO: 16; wherein the α1 chain of said procollagen comprises the collagen C propeptide having the sequence of the C propeptide of said collagen type I α1 chain and wherein the α2 of said procollagen comprises the collagen C propeptide having the sequence of the C propeptide of said collagen type I α2 chain, thereby promoting wound healing, treating fibrosis and/or promoting angiogenesis.

2. The method of claim 1, wherein said administering is effected into a tissue area which comprises said wound or a fibrotic tissue.

3. The method of claim 1, wherein said administering is effected prior to fibroblast recruitment to the wound.

4. The method of claim 1, wherein said procollagen is produced in plant cells.

5. The method of claim 1, wherein said procollagen is degradable by collagenase.

6. The method of claim 1, wherein said wound is related to a fibrotic condition selected from the group consisting of systemic or localized scleroderma, liver fibrosis, alcoholic cirrhosis, biliary cirrhosis, hepatitis, veno-occlusive disease, idiopathic interstitial fibrosis, idiopathic pulmonary fibrosis, interstitial pulmonary fibrosis, acute pulmonary fibrosis, acute respiratory distress syndrome, perimuscular fibrosis, pericentral fibrosis, dermatofibroma, kidney fibrosis, diabetic nephropathy, glomerulonephritis, keloids, hypertrophic scars, joint adhesions, arthrosis, myelofibrosis, corneal scaring, cystic fibrosis, muscular fibrosis, Duchenne's muscular dystrophy, esophageal stricture, retroabdominal scaring, Crohn's disease, ulcerative colitis, atherosclerotic alterations, pulmonary hypertension, angiopathy of the arteries and veins, aneurysms of large vessels or are induced or initiated by scar revisions, plastic surgeries, glaucoma, cataract fibrosis, corneal scaring, graft vs. host disease, tendon surgery, nerve entrapment, Dupuytren's contracture, OB/GYN adhesions, pelvic adhesions, peridural fibrosis, diseases of the thyroid gland or the parathyroids, metastatic bone disease, multiple myeloma and restenosis.

7. The method claim 1, wherein said wound is inflicted by diabetes.

8. The method claim 1, wherein said wound is selected from the group consisting of an ulcer, a burn and a surgical wound.

9. The method of claim 1, wherein said procollagen comprises monomeric procollagen.

* * * * *